(12) United States Patent
Istvan et al.

(10) Patent No.: US 8,255,041 B2
(45) Date of Patent: *Aug. 28, 2012

(54) WIRELESS ECG SYSTEM

(75) Inventors: Rud Istvan, Fort Lauderdale, FL (US); Bill Gregory, Fort Lauderdale, FL (US); Kenneth Solovay, Weston, FL (US); David Paul Chastain, Acton, MA (US); John David Gundlach, Acton, MA (US); Nicholas C. Hopman, Lake Zurich, IL (US); Daniel L. Williams, Norwell, MA (US); Franco Lodato, Weston, FL (US); Michael Salem, Ft. Lauderdale, FL (US)

(73) Assignee: LifeSync Corporation, Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/020,284

(22) Filed: Feb. 3, 2011

(65) Prior Publication Data

US 2011/0160604 A1    Jun. 30, 2011

Related U.S. Application Data

(63) Continuation of application No. 10/439,356, filed on May 16, 2003, now Pat. No. 7,933,642, which is a continuation-in-part of application No. 09/998,733, filed on Nov. 30, 2001, now Pat. No. 7,197,357, which is a continuation-in-part of application No. 09/908,509, filed on Jul. 17, 2001, now Pat. No. 6,611,705.

(60) Provisional application No. 60/392,882, filed on Jul. 1, 2002.

(51) Int. Cl.
*A61B 5/04* (2006.01)

(52) U.S. Cl. ......................................................... 600/509

(58) Field of Classification Search .................. 600/509
See application file for complete search history.

(56) References Cited

U.S. PATENT DOCUMENTS

| | | |
|---|---|---|
| 2,958,781 A | 11/1960 | Marchal et al. |
| 3,199,508 A | 4/1962 | Roth |
| 3,495,584 A | 2/1970 | Schwalm |
| 3,602,215 A | 8/1971 | Parnell |
| 3,603,881 A | 9/1971 | Thornton |
| 3,639,907 A | 2/1972 | Greatbatch |
| 3,727,190 A | 4/1973 | Vogelman |
| 3,729,708 A | 4/1973 | Wolfer |
| 3,757,778 A | 9/1973 | Graham |
| 3,774,594 A | 11/1973 | Huszar |
| 3,810,102 A | 5/1974 | Parks, III |
| 3,830,228 A | 8/1974 | Foner |
| 3,834,373 A | 9/1974 | Sato |

(Continued)

OTHER PUBLICATIONS

Neukomm, Peter A., A Radio-Controlled Monitoring System for Multichannel Telemetry, Biotelemetry, 1974, pp. 251-263, vol. 1.

(Continued)

*Primary Examiner* — George Manuel
(74) *Attorney, Agent, or Firm* — Dykema Gossett PLLC

(57) ABSTRACT

A wireless monitoring system and, more particularly, a wireless monitoring system for detecting and transmitting physiological data. The present invention detects physiological data relating to a patient's cardiac activity and respiration rate and transmits the data to a remote base station via telemetry. The base station processes the data so that the data can be display by an ECG monitor.

20 Claims, 34 Drawing Sheets

U.S. PATENT DOCUMENTS

| | | |
|---|---|---|
| 3,905,364 A | 9/1975 | Cudahy |
| 3,910,260 A | 10/1975 | Sarnoff |
| 3,925,762 A | 12/1975 | Heitlinger |
| 3,943,918 A | 3/1976 | Lewis |
| 3,970,996 A | 7/1976 | Yasaka |
| 3,986,498 A | 10/1976 | Lewis |
| 3,998,213 A | 12/1976 | Price |
| 4,027,663 A | 6/1977 | Fischler |
| 4,042,906 A | 8/1977 | Ezell |
| 4,051,522 A | 9/1977 | Healy |
| 4,074,228 A | 2/1978 | Jonscher |
| 4,121,573 A | 10/1978 | Crovella et al. |
| 4,124,894 A | 11/1978 | Vick |
| 4,141,351 A | 2/1979 | James et al. |
| 4,150,284 A | 4/1979 | Trenkler et al. |
| 4,156,867 A | 5/1979 | Bench |
| 4,173,221 A | 11/1979 | McLaughlin |
| 4,173,971 A | 11/1979 | Karz |
| 4,186,749 A | 2/1980 | Fryer |
| 4,216,462 A | 8/1980 | McGrath |
| 4,233,241 A | 11/1980 | Kalopissis |
| 4,237,900 A | 12/1980 | Schulman et al. |
| 4,260,951 A | 4/1981 | Lewyn |
| 4,262,632 A | 4/1981 | Hanton |
| 4,281,664 A | 8/1981 | Duggan |
| 4,321,993 A | 3/1982 | Baessler |
| 4,328,814 A | 5/1982 | Arkans |
| 4,353,372 A | 10/1982 | Ayer |
| 4,396,906 A | 8/1983 | Weaver |
| 4,425,921 A | 1/1984 | Fujisaki |
| 4,441,498 A | 4/1984 | Nordling |
| 4,449,536 A | 5/1984 | Weaver |
| 4,471,786 A | 9/1984 | Inagaki et al. |
| 4,475,208 A | 10/1984 | Ricketts |
| 4,494,552 A | 1/1985 | Heath |
| 4,510,495 A | 4/1985 | Sigrimis |
| 4,521,918 A | 6/1985 | Challen |
| 4,531,526 A | 7/1985 | Genest |
| 4,539,995 A | 9/1985 | Segawa |
| 4,556,061 A | 12/1985 | Barreras et al. |
| 4,556,063 A | 12/1985 | Thompson et al. |
| 4,562,840 A | 1/1986 | Batina et al. |
| 4,573,026 A | 2/1986 | Curtis |
| 4,583,548 A | 4/1986 | Schmid |
| 4,583,549 A | 4/1986 | Manoli |
| 4,585,004 A | 4/1986 | Brownlee |
| 4,586,508 A | 5/1986 | Batina et al. |
| 4,598,281 A | 7/1986 | Maas |
| 4,599,723 A | 7/1986 | Eck |
| 4,601,043 A | 7/1986 | Hardt |
| 4,606,352 A | 8/1986 | Geddes |
| 4,608,987 A | 9/1986 | Mills |
| 4,618,861 A | 10/1986 | Gettens |
| 4,625,733 A | 12/1986 | Saynajakangas |
| RE32,361 E | 2/1987 | Duggan |
| 4,653,068 A | 3/1987 | Kadin |
| 4,681,118 A | 7/1987 | Asai et al. |
| 4,709,704 A | 12/1987 | Lukasiewicz |
| 4,724,435 A | 2/1988 | Moses |
| 4,747,413 A | 5/1988 | Bloch |
| 4,754,483 A | 6/1988 | Weaver |
| 4,783,844 A | 11/1988 | Higashiyama |
| 4,784,162 A | 11/1988 | Ricks et al. |
| 4,791,933 A | 12/1988 | Asai et al. |
| 4,794,532 A | 12/1988 | Leckband |
| 4,799,059 A | 1/1989 | Grindahl |
| 4,802,222 A | 1/1989 | Weaver |
| 4,803,625 A | 2/1989 | Fu et al. |
| 4,805,631 A | 2/1989 | Roi du Maroc, II. |
| 4,835,372 A | 5/1989 | Gombrich |
| 4,839,806 A | 6/1989 | Goldfischer |
| 4,850,009 A | 7/1989 | Zook |
| 4,852,572 A | 8/1989 | Nakahashi et al. |
| 4,860,759 A | 8/1989 | Kahn et al. |
| 4,865,044 A | 9/1989 | Wallace |
| 4,883,064 A | 11/1989 | Olson |
| 4,889,131 A | 12/1989 | Salem et al. |
| 4,889,132 A | 12/1989 | Hutcheson |
| 4,909,260 A | 3/1990 | Salem et al. |
| 4,916,441 A | 4/1990 | Gombrich |
| 4,928,187 A | 5/1990 | Rees |
| 4,955,075 A | 9/1990 | Anderson |
| 4,957,109 A | 9/1990 | Groeger et al. |
| 4,958,645 A | 9/1990 | Cadell et al. |
| 4,966,154 A | 10/1990 | Cooper et al. |
| 4,974,607 A | 12/1990 | Miwa |
| 4,981,141 A | 1/1991 | Segalowitz |
| 5,012,411 A | 4/1991 | Policastro et al. |
| 5,025,452 A | 6/1991 | Sohner |
| 5,025,808 A | 6/1991 | Hafner |
| 5,036,462 A | 7/1991 | Kaufman |
| 5,036,869 A | 8/1991 | Inahara |
| 5,042,498 A | 8/1991 | Dukes |
| 5,051,799 A | 9/1991 | Paul |
| 5,072,383 A | 12/1991 | Brimm |
| 5,077,753 A | 12/1991 | Grau |
| 5,078,134 A | 1/1992 | Heilman |
| 5,085,224 A | 2/1992 | Galen |
| 5,109,845 A | 5/1992 | Yuuchi et al. |
| 5,113,869 A | 5/1992 | Nappholz et al. |
| 5,127,404 A | 7/1992 | Wyborny |
| 5,131,399 A | 7/1992 | Sciarra |
| 5,137,022 A | 8/1992 | Henry |
| 5,153,584 A | 10/1992 | Engira |
| 5,157,604 A | 10/1992 | Axford |
| 5,168,874 A | 12/1992 | Segalowitz |
| 5,171,977 A | 12/1992 | Morrison |
| 5,177,765 A | 1/1993 | Holland |
| 5,177,766 A | 1/1993 | Holland |
| 5,179,569 A | 1/1993 | Sawyer |
| 5,179,571 A | 1/1993 | Schilling |
| 5,181,519 A | 1/1993 | Bible |
| 5,184,620 A | 2/1993 | Cudahy |
| 5,191,886 A | 3/1993 | Paeth et al. |
| 5,192,949 A | 3/1993 | Suzuki |
| 5,205,294 A | 4/1993 | Flach et al. |
| 5,212,476 A | 5/1993 | Maloney |
| 5,212,715 A | 5/1993 | Pickert |
| 5,224,479 A | 7/1993 | Sekine |
| 5,224,485 A | 7/1993 | Powers |
| 5,226,431 A | 7/1993 | Bible |
| 5,238,001 A | 8/1993 | Gallant et al. |
| 5,270,811 A | 12/1993 | Ishibashi |
| 5,272,477 A | 12/1993 | Tashima |
| 5,292,343 A | 3/1994 | Blanchette |
| 5,305,202 A | 4/1994 | Gallant |
| 5,305,353 A | 4/1994 | Weerackody |
| 5,307,372 A | 4/1994 | Sawyer |
| 5,307,817 A | 5/1994 | Guggenbuhl |
| 5,307,818 A | 5/1994 | Segalowitz |
| 5,309,920 A | 5/1994 | Gallant et al. |
| 5,314,450 A | 5/1994 | Thompson |
| 5,319,363 A | 6/1994 | Welch et al. |
| 5,327,888 A | 7/1994 | Imran |
| 5,335,664 A | 8/1994 | Nagashima |
| 5,339,824 A | 8/1994 | Engira |
| 5,341,806 A | 8/1994 | Gadsby et al. |
| 5,342,408 A | 8/1994 | deCoriolis |
| 5,343,869 A | 9/1994 | Pross |
| 5,343,870 A | 9/1994 | Gallant et al. |
| 5,348,008 A | 9/1994 | Bomn et al. |
| 5,353,791 A | 10/1994 | Tamura |
| 5,353,793 A | 10/1994 | Bornn |
| 5,354,319 A | 10/1994 | Wyborny |
| 5,359,641 A | 10/1994 | Schull |
| 5,365,530 A | 11/1994 | Yoshida |
| 5,375,604 A | 12/1994 | Kelly |
| 5,377,222 A | 12/1994 | Sanderford |
| 5,381,798 A | 1/1995 | Burrows |
| 5,392,771 A | 2/1995 | Mock |
| 5,394,879 A | 3/1995 | Gorman |
| 5,394,882 A | 3/1995 | Mawhinney |
| 5,400,794 A | 3/1995 | Gorman |
| 5,417,222 A | 5/1995 | Dempsey |
| 5,438,607 A | 8/1995 | Pzygoda, Jr. |
| 5,441,047 A | 8/1995 | David |
| 5,444,719 A | 8/1995 | Cox |

| Patent | Date | Name |
|---|---|---|
| 5,458,122 A | 10/1995 | Hethuin |
| 5,458,123 A | 10/1995 | Unger |
| 5,458,124 A | 10/1995 | Stanko et al. |
| 5,464,021 A | 11/1995 | Birnbaum |
| 5,485,848 A | 1/1996 | Jackson et al. |
| 5,491,474 A | 2/1996 | Suni et al. |
| 5,507,035 A | 4/1996 | Bantz |
| 5,511,553 A | 4/1996 | Segalowitz |
| 5,522,396 A | 6/1996 | Langer et al. |
| 5,524,637 A | 6/1996 | Erickson |
| 5,538,007 A | 7/1996 | Gorman |
| 5,544,649 A | 8/1996 | David et al. |
| 5,544,661 A | 8/1996 | Davis et al. |
| 5,546,950 A | 8/1996 | Schoeckert et al. |
| 5,549,113 A | 8/1996 | Halleck et al. |
| 5,564,429 A | 10/1996 | Bornn |
| 5,568,814 A | 10/1996 | Gallant et al. |
| 5,575,284 A | 11/1996 | Athan et al. |
| 5,576,952 A | 11/1996 | Stutman |
| 5,579,001 A | 11/1996 | Dempsey |
| 5,579,378 A | 11/1996 | Arlinghaus, Jr. |
| 5,579,775 A | 12/1996 | Dempsey |
| 5,579,781 A | 12/1996 | Cooke |
| 5,582,180 A | 12/1996 | Manset |
| 5,586,552 A | 12/1996 | Sakai |
| 5,617,871 A | 4/1997 | Burrows |
| 5,623,925 A | 4/1997 | Swenson |
| 5,628,324 A | 5/1997 | Sarbach |
| 5,628,326 A | 5/1997 | Arand et al. |
| 5,634,468 A | 6/1997 | Platt et al. |
| 5,640,953 A | 6/1997 | Bishop |
| 5,645,059 A | 7/1997 | Fein et al. |
| 5,645,571 A | 7/1997 | Olson et al. |
| 5,646,701 A | 7/1997 | Duckworth |
| 5,664,270 A | 9/1997 | Bell |
| 5,669,391 A | 9/1997 | Williams |
| 5,678,545 A | 10/1997 | Stratbucker |
| 5,678,562 A | 10/1997 | Sellers |
| 5,685,303 A | 11/1997 | Rollman |
| 5,690,119 A | 11/1997 | Rytky et al. |
| 5,694,940 A | 12/1997 | Unger et al. |
| 5,704,351 A | 1/1998 | Mortara et al. |
| 5,718,234 A | 2/1998 | Warden et al. |
| 5,720,771 A | 2/1998 | Snell |
| 5,738,102 A | 4/1998 | Lemelson |
| 5,746,207 A | 5/1998 | McLaughlin et al. |
| 5,748,103 A | 5/1998 | Flach et al. |
| 5,749,365 A | 5/1998 | Magill |
| 5,755,230 A | 5/1998 | Schmidt et al. |
| 5,759,199 A | 6/1998 | Snell et al. |
| 5,767,791 A | 6/1998 | Stoop et al. |
| 5,776,057 A | 7/1998 | Swenson |
| 5,779,630 A | 7/1998 | Fein |
| 5,782,238 A | 7/1998 | Beitler |
| 5,788,633 A | 8/1998 | Mahoney |
| 5,800,204 A | 9/1998 | Nitsu |
| 5,813,404 A | 9/1998 | Devlin |
| 5,819,740 A | 10/1998 | Muhlenberg |
| 5,820,567 A | 10/1998 | Mackie |
| 5,827,179 A | 10/1998 | Lichter |
| 5,855,550 A | 1/1999 | Lai |
| 5,862,803 A | 1/1999 | Besson et al. |
| 5,865,733 A | 2/1999 | Malinouskas et al. |
| 5,865,741 A | 2/1999 | Kelly et al. |
| 5,868,671 A | 2/1999 | Mahoney |
| 5,871,451 A | 2/1999 | Kolnsberg et al. |
| 5,873,369 A | 2/1999 | Laniado |
| 5,873,821 A | 2/1999 | Chance et al. |
| 5,882,300 A | 3/1999 | Malinouskas et al. |
| 5,899,928 A | 5/1999 | Sholder et al. |
| 5,899,931 A | 5/1999 | Deschamp et al. |
| 5,907,291 A | 5/1999 | Chen et al. |
| 5,913,827 A | 6/1999 | Gorman |
| 5,916,159 A | 6/1999 | Kelly et al. |
| 5,917,414 A | 6/1999 | Oppelt |
| 5,919,141 A | 7/1999 | Money et al. |
| 5,919,214 A | 7/1999 | Ciciarelli et al. |
| 5,931,791 A | 8/1999 | Saltzstein |
| 5,935,078 A | 8/1999 | Feierbach |
| 5,938,597 A | 8/1999 | Stratbucker |
| 5,944,659 A | 8/1999 | Flach et al. |
| 5,949,352 A | 9/1999 | Ferrari |
| 5,954,536 A | 9/1999 | Fuerst et al. |
| 5,954,719 A | 9/1999 | Chen et al. |
| 5,957,854 A | 9/1999 | Besson et al. |
| 5,959,529 A | 9/1999 | Kail, IV |
| 5,961,448 A | 10/1999 | Swenson |
| 5,963,650 A | 10/1999 | Simionescu et al. |
| 5,964,701 A | 10/1999 | Asada et al. |
| 5,966,692 A | 10/1999 | Langer et al. |
| 5,970,105 A | 10/1999 | Dacus |
| 5,999,857 A | 12/1999 | Weijand et al. |
| 6,009,350 A | 12/1999 | Renken |
| 6,010,359 A | 1/2000 | Etters et al. |
| 6,027,363 A | 2/2000 | Watt et al. |
| 6,039,600 A | 3/2000 | Etters et al. |
| 6,047,201 A | 4/2000 | Jackson, III |
| 6,053,887 A | 4/2000 | Levitas |
| 6,055,448 A | 4/2000 | Anderson et al. |
| 6,055,506 A * | 4/2000 | Frasca, Jr. .................. 705/3 |
| 6,057,758 A | 5/2000 | Dempsey et al. |
| 6,066,093 A | 5/2000 | Kelly |
| 6,073,046 A | 6/2000 | Patel et al. |
| 6,074,345 A | 6/2000 | vanOostrom |
| 6,076,003 A | 6/2000 | Rogel |
| 6,077,124 A | 6/2000 | Etters et al. |
| 6,083,248 A | 7/2000 | Thompson |
| 6,086,412 A | 7/2000 | Watt et al. |
| 6,093,146 A | 7/2000 | Filangeri |
| 6,102,856 A | 8/2000 | Groff et al. |
| 6,115,622 A | 9/2000 | Minoz |
| 6,117,076 A | 9/2000 | Cassidy |
| 6,119,029 A | 9/2000 | Williams |
| 6,139,495 A | 10/2000 | De La Huerga |
| 6,141,575 A | 10/2000 | Price |
| 6,146,190 A | 11/2000 | Fuerst et al. |
| 6,147,618 A | 11/2000 | Halleck |
| 6,149,602 A | 11/2000 | Arcelus |
| 6,150,951 A | 11/2000 | Olejniczak |
| 6,154,676 A | 11/2000 | Levine |
| 6,157,851 A | 12/2000 | Kelly et al. |
| 6,198,394 B1 | 3/2001 | Jacobsen |
| 6,206,837 B1 | 3/2001 | Brugnoli |
| 6,208,889 B1 | 3/2001 | Gorman |
| 6,213,942 B1 | 4/2001 | Flach et al. |
| 6,219,568 B1 | 4/2001 | Kelly et al. |
| 6,219,569 B1 | 4/2001 | Kelly et al. |
| 6,225,901 B1 | 5/2001 | Kail |
| 6,236,874 B1 | 5/2001 | Devlin |
| 6,238,338 B1 | 5/2001 | DeLuca et al. |
| 6,244,890 B1 | 6/2001 | Fuerst et al. |
| 6,246,902 B1 | 6/2001 | Naylor et al. |
| 6,259,939 B1 | 7/2001 | Rogel |
| 6,267,723 B1 | 7/2001 | Matsumura |
| 6,287,252 B1 | 9/2001 | Lugo |
| 6,289,238 B1 | 9/2001 | Besson et al. |
| 6,292,687 B1 | 9/2001 | Lowell et al. |
| 6,295,466 B1 | 9/2001 | Ishikawa et al. |
| 6,304,774 B1 | 10/2001 | Gorman |
| 6,319,200 B1 | 11/2001 | Lai |
| 6,332,094 B1 | 12/2001 | Gorman |
| 6,364,834 B1 | 4/2002 | Reuss |
| 6,381,492 B1 | 4/2002 | Rockwell et al. |
| 6,385,473 B1 | 5/2002 | Haines et al. |
| 6,389,308 B1 | 5/2002 | Shusterman |
| 6,408,200 B1 | 6/2002 | Takashina |
| 6,415,169 B1 | 7/2002 | Kornrumpf et al. |
| 6,416,471 B1 | 7/2002 | Kumar |
| 6,440,067 B1 | 8/2002 | DeLuca |
| 6,441,747 B1 | 8/2002 | Khair |
| 6,443,890 B1 | 9/2002 | Schulze et al. |
| 6,450,953 B1 | 9/2002 | Place |
| 6,453,186 B1 | 9/2002 | Lovejoy et al. |
| 6,454,708 B1 | 9/2002 | Ferguson et al. |
| 6,470,893 B1 | 10/2002 | Boesen |
| 6,480,733 B1 | 11/2002 | Turcott |
| 6,496,705 B1 | 12/2002 | Ng et al. |
| 6,532,379 B2 | 3/2003 | Stratbucker |

| | | | |
|---|---|---|---|
| 6,544,173 B2 | 4/2003 | West et al. |
| 6,544,174 B2 | 4/2003 | West et al. |
| 6,560,473 B2 | 5/2003 | Dominguez |
| 6,602,191 B2 | 8/2003 | Quy |
| 6,602,201 B1 | 8/2003 | Hepp et al. |
| 6,611,705 B2 | 8/2003 | Hopman et al. |
| 6,616,606 B1 | 9/2003 | Petersen et al. |
| 6,654,631 B1 | 11/2003 | Sahai |
| 6,694,180 B1 | 2/2004 | Boesen |
| 6,970,737 B1 | 11/2005 | Brodnick et al. |
| 7,197,357 B2 | 3/2007 | Istvan et al. |
| 7,382,247 B2 | 6/2008 | Welch et al. |
| 7,481,772 B2 | 1/2009 | Banet |
| 7,614,742 B2 | 11/2009 | Geiger |
| 7,801,626 B2 | 9/2010 | Moser |
| 7,899,526 B2 | 3/2011 | Benditt et al. |
| 2002/0038094 A1 | 3/2002 | Gorman |
| 2005/0228299 A1 | 10/2005 | Banet |
| 2005/0228300 A1 | 10/2005 | Jaime et al. |
| 2005/0277841 A1 | 12/2005 | Shennib |
| 2006/0047214 A1 | 3/2006 | Fraden |
| 2006/0047447 A1 | 3/2006 | Brady et al. |
| 2006/0142648 A1 | 6/2006 | Banet et al. |
| 2006/0155173 A1 | 7/2006 | Anttila et al. |
| 2006/0178617 A1 | 8/2006 | Adams et al. |

OTHER PUBLICATIONS

Kimmich, H.P. and Vos, J.A., Telemetry of Respiratory Air Flow, Biotelemetry International Symposium, May 5-8, 1971, pp. 111-120, Meander N. V., Netherlands.

Kimmich, H.P. and Vos, J.A., Single to Seven Channel Lightweight Biotelemetry System, Biotelemetry International Symposium, May 5-8, 1971, pp. 57-64, Meander N. V., Netherlands.

Kimmich, H.P. and Ijsenbrandt, H.J.B., Personal PDM/PCM Biotelemetry System, Biotelemetry II Second International Symposium, May 20-24, 1974, pp. 2-4, S. Karger, Basel.

Kimmich, H.P., Clinical Telemetry and Patient Monitoring, Biotelemetry II Second International Symposium, May 20-24, 1974, pp. 190-195, S. Karger, Basel.

Kimmich, H.P. and Kreuzer, F., Trends in Biomedical Telemetry and Patient Monitoring, date unknown, pp. E2-7(1)-(2).

Kimmich, H.P., Biotelemetry, Encyclopedia of Medical Devices and Instrumentation, 1988, pp. 409-425, vol. 1., John Wiley & Sons, USA.

Kimmich, H.P., Modern Patient Care Using Biotelemetry: It's Potential and Technical Realization at Present and in the Future, Medical Progress Through Technology, 1982, pp. 85-93, vol. 9, No. 2/3, Springer-Verlag.

Skutt, H.R., Fell, R.B. and Hagstrom, E.C., The Use of Telemetry to Obtain Physiological Data During Exercise, Biotelemetry International Symposium, May 5-8, 1971, pp. 21-29, Meander N. V., Netherlands.

Ivison, J.M., Hoare D.W. and Qazi, S., A Time-Division Multiplexed Telemetry System Using Delta-Modulation, Biotelemetry International Symposium, May 5-8, 1971, pp. 39-48.

Zerzawy, R. and Bachmann, K., A Programmable Four Channel System for Long-Term Radio Telemetry of Biomedical Parameters, Biotelemetry International Symposium, 1971, pp. 49-56.

Ijsenbrandt, H.J.B., Kimmich, H.P. and Van Den Akker, A.J., Single to Seven Channel Lightweight Biotelemetry System, Biotelemetry International Symposium, 1971, pp. 57-64.

Klein, M., Milhaud, C. and Rebelle, J., Development an Adjustment of a Multi-Channel Miniaturized FM/AM Telemetering System Adapted to Primates, Biotelemetry International Symposium, May 5-8, 1971, pp. 83-88.

Kocnar, K. and Vichr, R., Mobile Telemetric Equipment for the Transmission of ECG and Respiratory Frequency with Automatic Data Recording, Biotelemetry International Symposium, May 5-8, 1971, pp. 95-98.

Kimmich, H.P., Oxygen Consumption Measurements During Exercise by Means of Radiotelemetry, Biotelemetry International Symposium, May 5-8, 1971, pp. 130-136.

Gachmann, K. and Zerzawy, R., Radiotelemetry of Direct Blood Pressure Movements in Aorta, Pulmonary Artery and Heart, Biotelemetry International Symposium, 1971, p. 183, 186-7.

Kurukawa, T. Tsuchida, Y., Matsumoto, G. and Shigezumi, M., Technical Improvements in Radiotelemetering of the Electrocardiogram, Biotelemetry International Symposium, May 5-8, 1971m, pp. 202-215.

Wilson-Davies, C.C., Multi-Channel Telemetry of Cardiovascular Data, Biotelemetry International Symposium, May 5-8, 1971, pp. 234-236.

Castelfiori, S. and Dubini, S., Radiotelemetry System for Fetal Monitoring, Biotelemetry International Symposium, May 5-8, 1971, pp. 237-245.

Kozinski, E., Estimation of the Intensity of Physical Exercises in Children and Adolescents Based on Telemetric Studies of Circulatory System, Biotelemetry International Symposium, May 5-8, 1971, pp. 251-255.

Rous, J. and Kocnar, K., Telemetrical Measurements During Sport Performance on Sportsmen with Cardiac Arrhythmias, Biotelemetry International Symposium, 1971, pp. 256-263.

Vos, J.A. and Kimmich, H.P., Telemetry of Biomechanical Forces During Exercise, Biotelemetry International Symposium, May 5-8, 1971, pp. 279-288.

Kristan, L., Dvorak, M., Zacek, I. and Pokorny, F., Experience with the Application of Biotelemetry (ECG, EMG) Under Strenuous Working Conditions in Various Operational Environments, Biotelemetry International Symposium, May 5-8, 1971, pp. 289-297.

Wagner, G., Hrynczuk, J.R. and Nielsen, J.F., EMG from Smooth Musculature (Uterus, Ureter, Gut) in Unrestrained Animals Monitored by Telemetry, Biotelemetry International Symposium, May 5-8, 1971, pp. 298-304.

Stalberg, E. and Kaiser, E., Long-Term EEG Telemetry, Biotelemetry International Symposium, May 5-8, 1971, pp. 307-316.

Currie, J.C.M., Riddle, H.C. and Watson, B.W., The Use of Telemetry to Study the Physiological and Clinical Variations of Intracranial Pressure in Man, Biotelemetry International Symposium, May 5-8, 1971, pp. 326-331.

Sandler, H., Fryer, T.B. and Westbrook, R.M., Single and Multichannel Implanted Telemetry Systems, Biotelemetry International Symposium, May 5-8, 1971, pp. 345-352.

Evans, B.T., A Remotely Operated ECG Telemeter for Chronic Implantation in Rats, Biotelemetry International Symposium, May 5-8, 1971, pp. 353-359.

Nielsen, J.F. and Wagner, G., Implantable FM-Telemetry Transmitters for Registration of Biopotentials, Biotelemetry International Symposium, May 5-8, 1971, pp. 360-364.

Voegeli, F. and Kraft, W., Multichannel Telemetry of Physiological Parameters (Body Temperature, ECG, EEG) in the Rat: 1. Design and Methods, Biotelemetry International Symposium, May 5-8, 1971, pp. 371-380.

Borbely, A.A., Baumann, I. and Waser, N. M., Multichannel Telemetry of Physiological Parameters (Body Temperature, EKG, EEG) in the Rat: II. Applications in Neuropharmacology, Biotelemetry International Symposium, May 5-8, 1971, pp. 381-388.

Pircher, L.A., Telemetry of Cardiovascular Parameters on Fighter Aircraft Flying Pilots, Biotelemetry Internationals Symposium, May 5-8, 1971, pp. 406-411.

Cook, T., Fernald, K.W., Miller, T.K. and Paulos, J.J., A Custom Microprocessor for Implantable Telemetry Systems, Third Annual IEEE Symposium on Computer-Based Medical Systems, Jun. 3-6, 1990, pp. 412-417.

Fernald, K.W., Stackhouse, B.A., Paulos, J.J. and Miller, T.K., A System Architecture for Intelligent Implantable Biotelemetry Instruments, Proceedings of the Annual International Conference of the IEEE Engineering in Medicine and Biology Society, Nov. 9-12, 1989, vol. 11, pp. 1411-1412.

Fernald, K.W., Cook, T.A., Miller III, T.K. and Paulos, J.J., A Microprocessor-Based Implantable Telemetry System, Computer, Mar. 1991, pp. 23-30.

Stackhouse, B.A., Thesis: A Transmitter Circuit Design for an Implantable Biomedical Chip Set, North Carolina State University, 1989.

Powers, C.C., Thesis: A Base Station Receiver for Biomedical Telemetry, North Carolina State University, 1991.

Fernald, K.W., Thesis: A Microprocessor-Based System for the Fast Prototyping of Implantable Instruments for Biomedical Research Applications, North Carolina State University, 1991.

Newell, D.C., "ECG Standard Patient Belt," IBM Technical Disclosure Bulletin, Jul. 1984, USA, vol. 24, No. 2, pp. 1144-1145. ISSN: 0018-8689.

Kimmich, H.P., "Clinical Telemetry and Patient Monitoring," Biotelemetry II: Proceedings of the Second International Symposium on Biotelemetry, 1974, pp. 190-195, Switzerland.

Zerzawy, R., "Simultaneous Wireless Telemetry for Several Biologic Measurements. Technics and Application of a New 4-Channel Telemetry," periodical—Z Kreislaufforsch, Feb. 1971, pp. 162-169, vol. 60, Part 2.

Retzke, F., "Experiences with a Mobile Monitoring System for Fetal and Neonatal Cardiotachometry," periodical—Zentraibl Gynakol, 1984, pp. 545-549, vol. 106.

Van Rijn, A.C.M., "Modeling of Biopotential Recordings and It's Implications for Instrumentation Design," doctoral thesis—available from the National Technical Information Services, Springfield, VA, Nov. 8, 1993, 153 pages.

Niitani, H., "Telemetry with Special Reference to Wireless Transmission of Electrocardiogram," periodical—Nippon Rinsho, Dec. 1969, pp. 2873-2882, vol. 27, Part 12.

Kimmich, H.P., "Biotelemetry in Anesthesia and Intensive Care," periodical—Anesth Analg (Paris), 1979, pp. 383-387, vol. 36, Part 9-10.

Henne, B., "Comparison Between Wilson's Thoracic Leads and the Telemetrically Transmitted Lead CM6 in Patients with Heart Diseases During Exertion," periodical—Z Kardiol, Mar. 1975, pp. 274-280, vol. 64, Part 3.

Baumgarten, K., "Wireless Transmission of the Fetal Electrocardiogram and Fetal Heart Beat During Pregnancy and Labor," periodical—Arch Gynakol, 1967, pp. 267-268, vol. 204, Part 2.

Muller, S., "Multifrequency Selective RF Pulses for Multislice MR Imaging," periodical—Magnetic Resonancy in Medicine, 1988, pp. 364-372, vol. 6, Part 3.

Harlow, H.J., "Adrenal Responsiveness in Domestic Sheep (Ovis aries) to Acute and Chronic Stressors as Predicted by Remote Monitoring of Cardiac Frequency," periodical—Canadian Journal of Zoology, 1987, pp. 2021-2027, vol. 65, Part 8.

Spraggins, T.A., "Wireless Retrospective Gating: Application to Cine Cardiac Imaging," periodical—Magnetic Resonance Imaging, 1990, pp. 675-681, vol. 8, Part 6.

White, R.D., "Electrocardiograph—Independent, "Wireless" Cardiovascular Cine MR Imaging," periodical—Magnetic Resonance Imaging, May-Jun. 1991, pp. 347-355, vol. 1, Part 3.

Watkinson, W.P., "Improved Technique for Monitoring Electrocardiograms During Exposure to Radio-Frequency Radiation," periodical—AM J Physiological Society, 1986, pp. H320-H324, vol. 250, Part 2.

Annovazzi-Lodi, Valerio, "Optoelectronic Telemetry of Electrophysiological Signals," periodical—Proceedings of SPIE, 1990, pp. 113-119, vol. 1355.

Schulze, H.J., "The Telemetric Emergency Electrocardiography—Practical Use and Methodologic Effectiveness," periodical—Z Gesamete Inn Med, Dec. 15, 1986, pp. 685-689, vol. 41, Part 24.

Jones, J.W., "Remote Monitoring of Free Flaps with Telephonic Transmission of Photoplethysmograph Waveforms," periodical—Journal of Reconstructive Microsurgery, Apr. 1989, pp. 141-144, vol. 5, Part 2.

Bashein, G., "Anesthesia and Remote Monitoring for Intraoperative Radiation Therapy," periodical—Anesthesiology, Jun. 1986, pp. 804-807, vol. 64, Part 6.

Athan, Stephan, "Benefits of Spread Spectrum Technology in Present and Future Health Care Applications," conference—15th Annual International Conference IEEE Eng in Med & Bio Soc, San Diego, CA, 1993, pp. 1045-1046, vol. 15, Part 2.

Hanley, J., "Telemetry in Health Care," periodical—Biomedical Engineering, Aug. 1976, pp. 269-272, vol. 11, Part 8.

Office Action mailed Sep. 22, 2011 in U.S. Appl. No. 12/955,490.

* cited by examiner

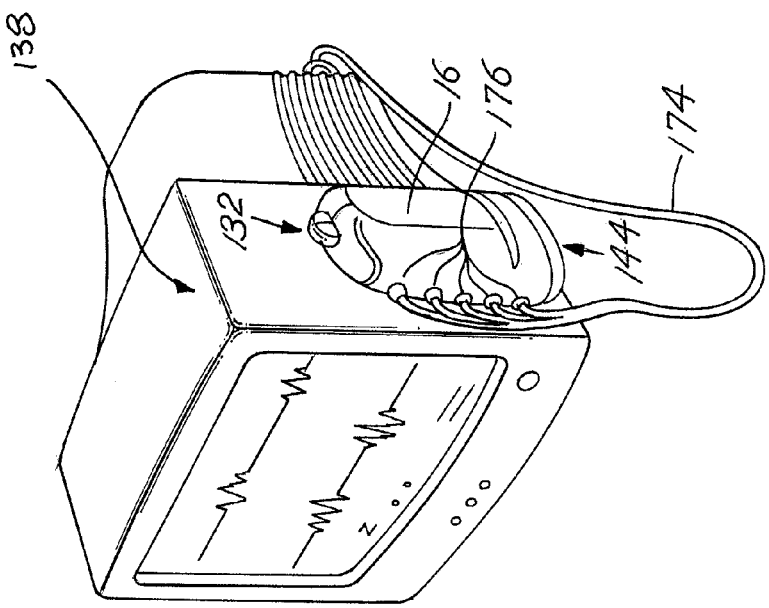
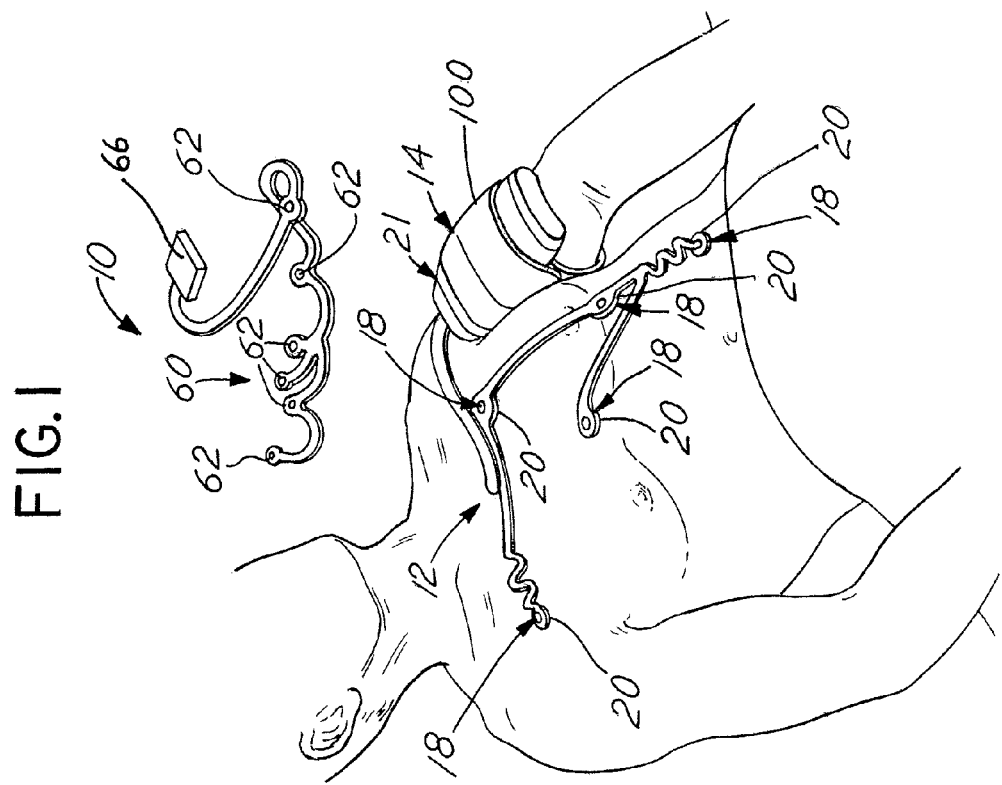
FIG. 1

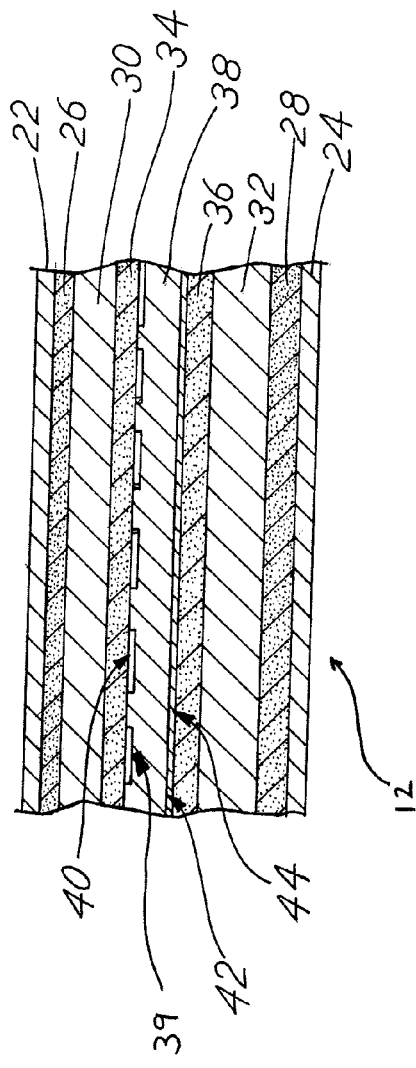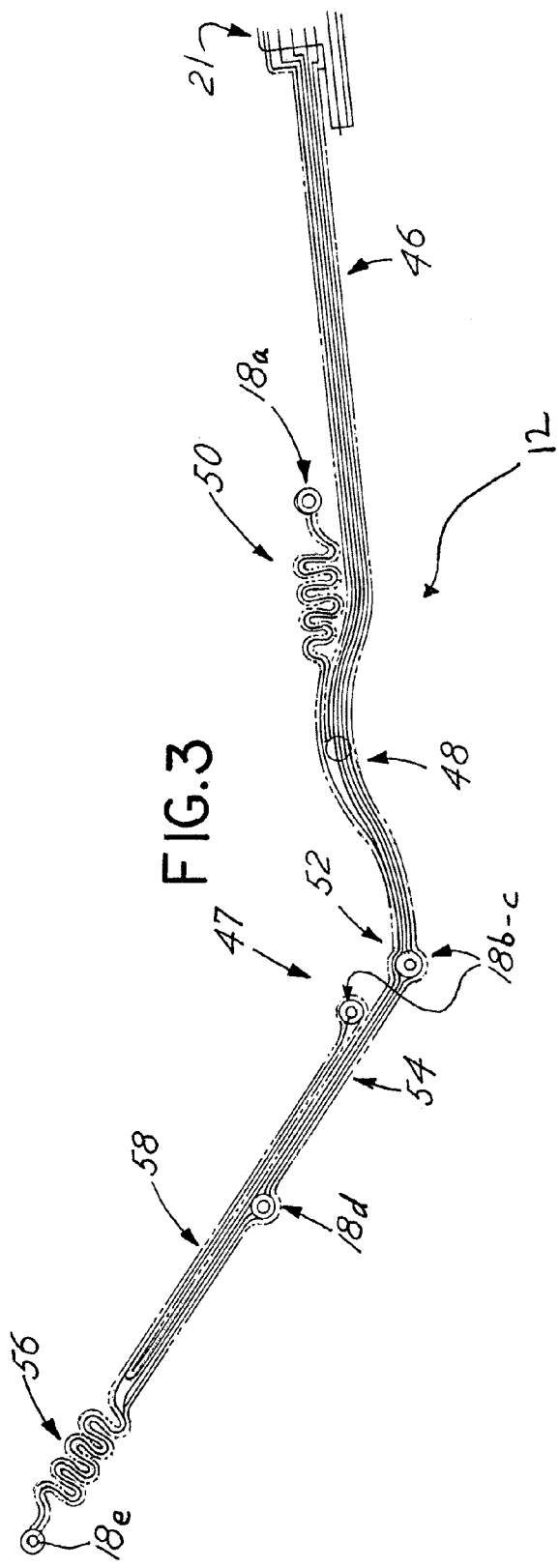

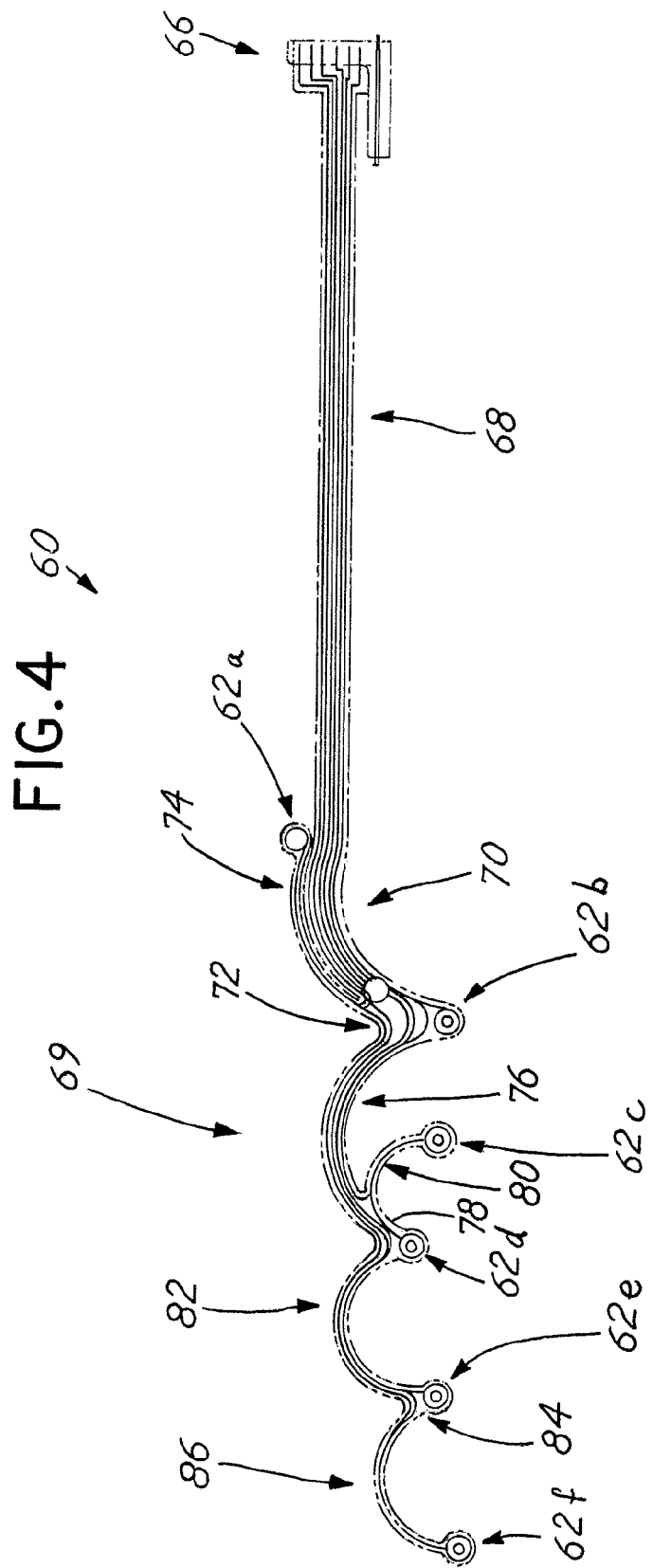

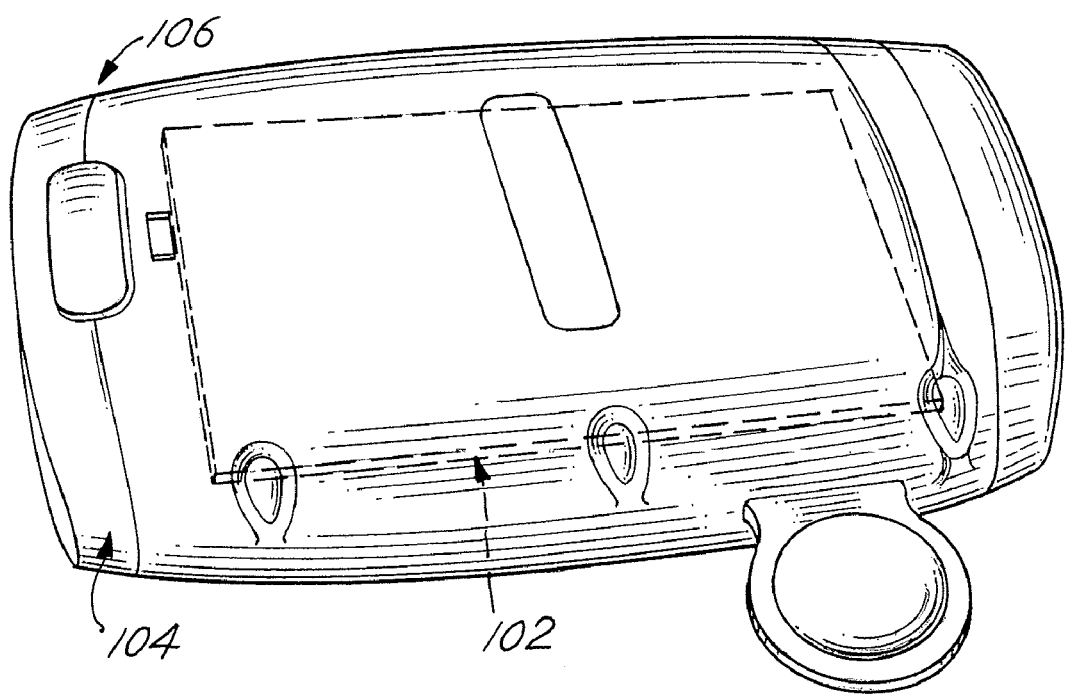

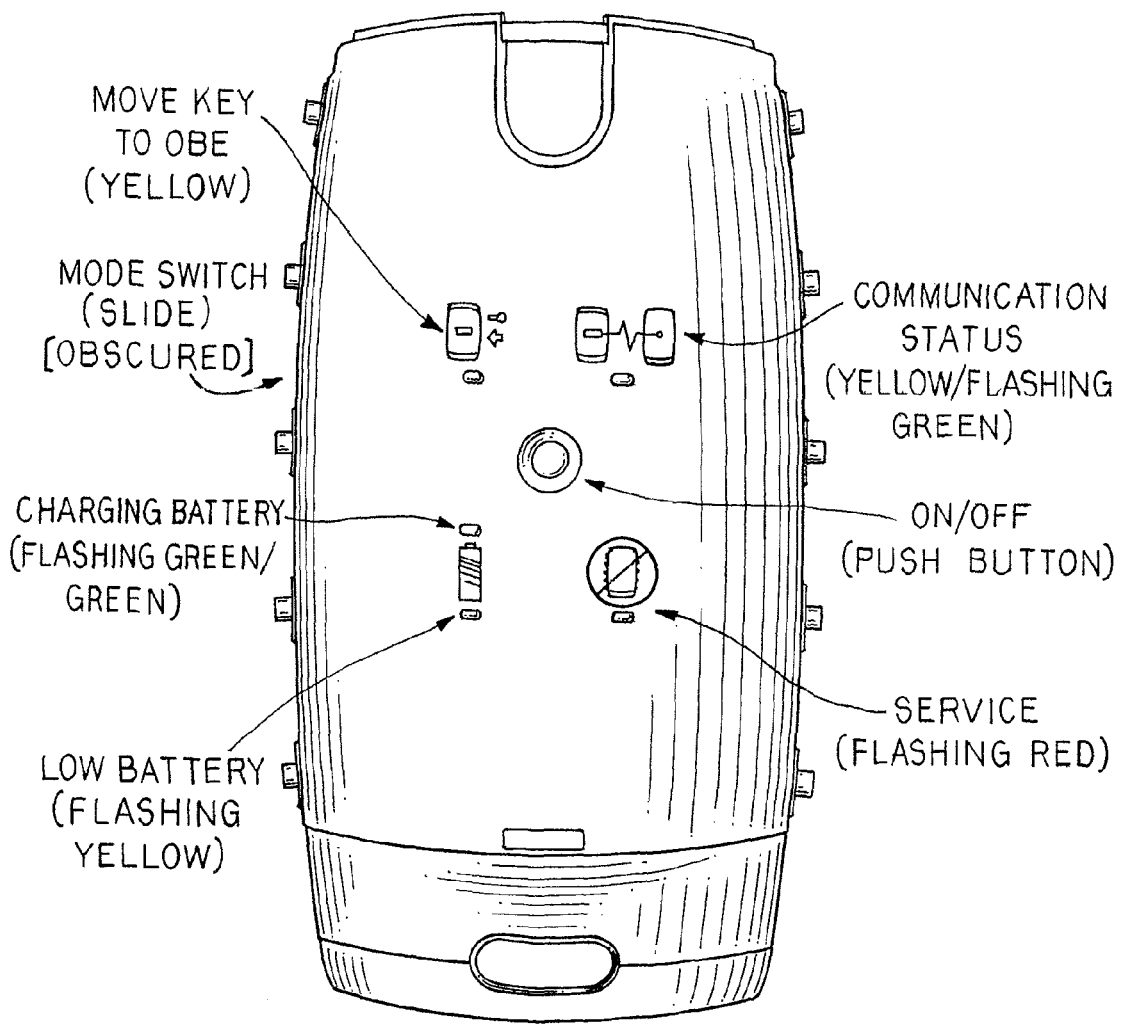

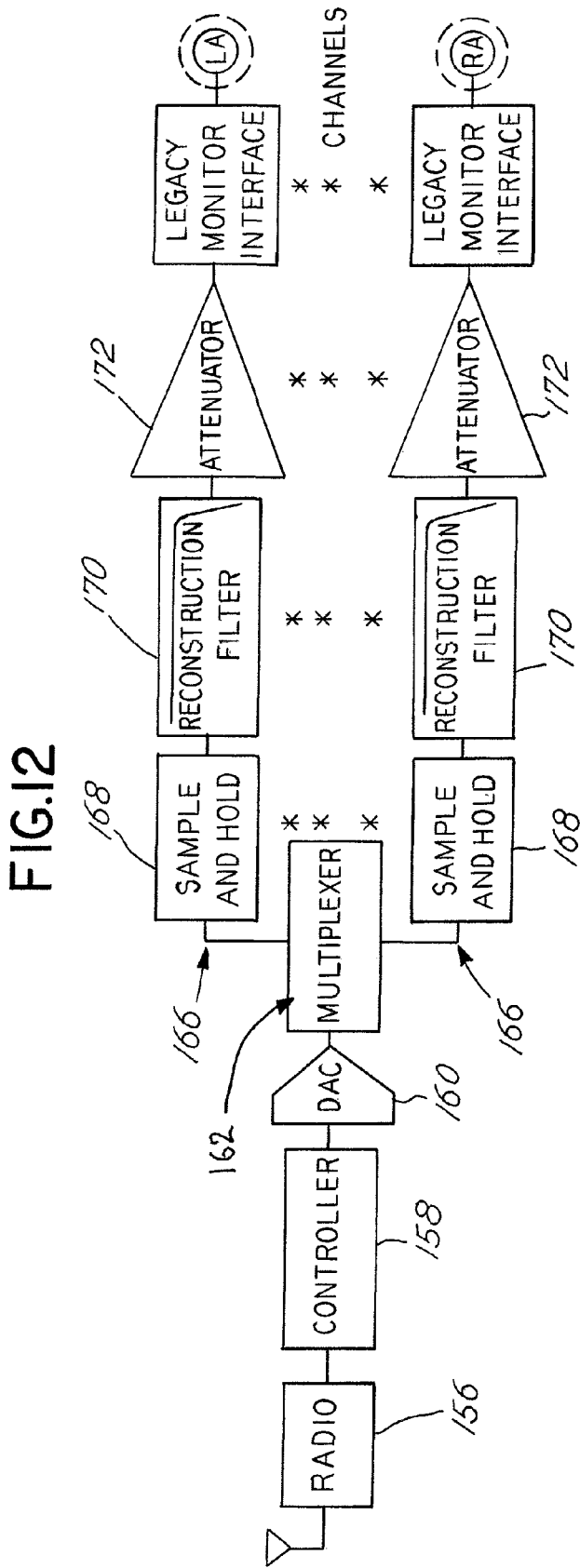

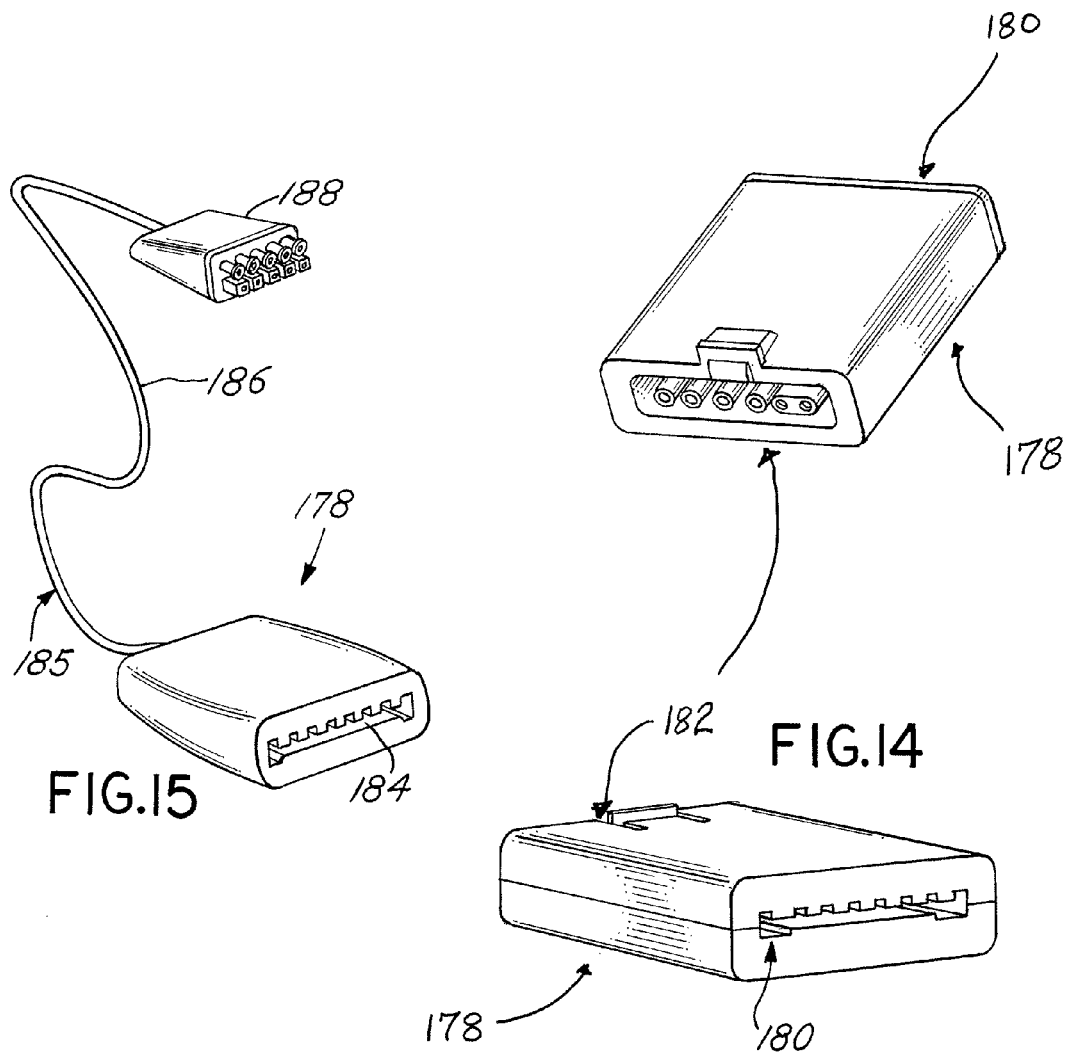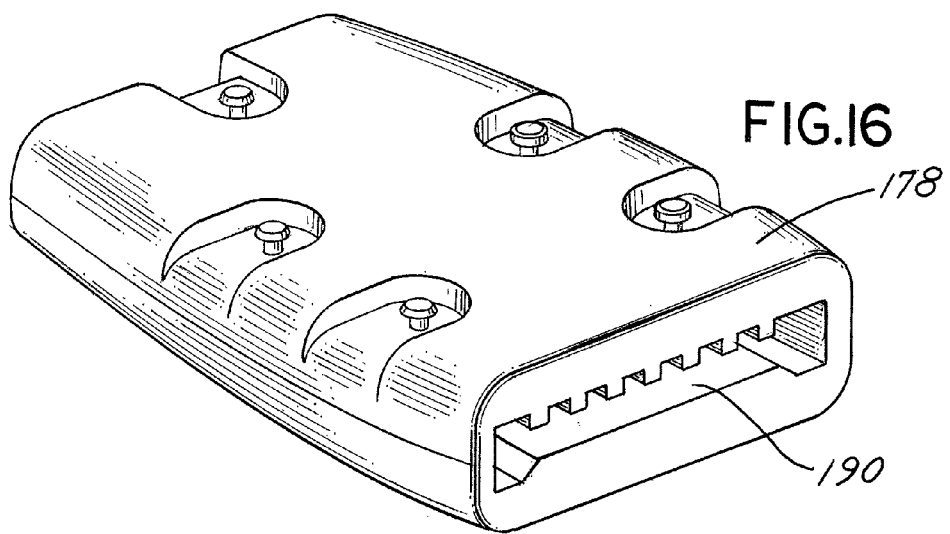

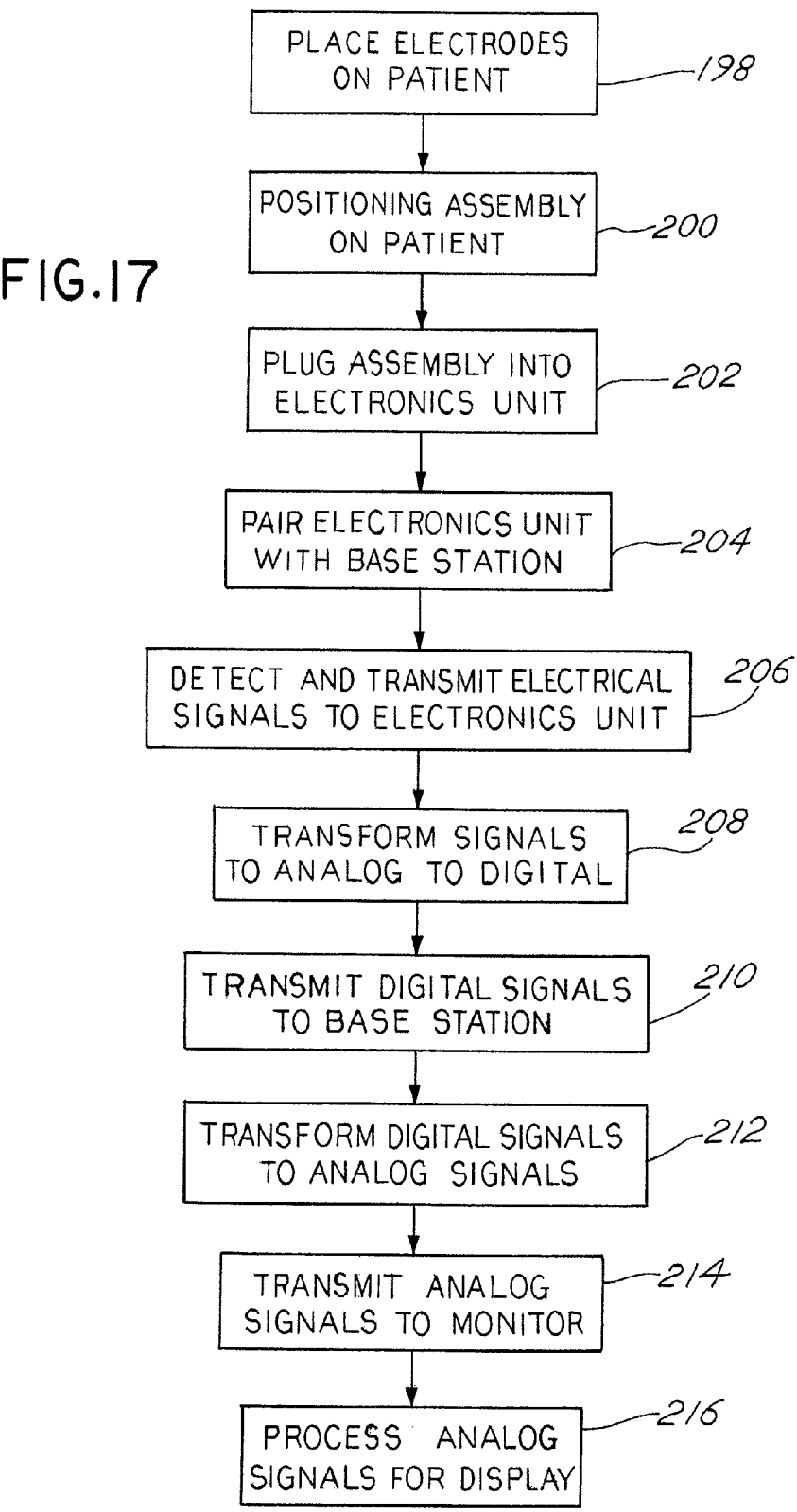

ECG Data Packet for 9 channel ECG data (112 bytes total, describing 12 msec worth of data)

| ECG Pkt Identifier | Num of Chan 9 | ECG ID | ECG Data (Decimated Dataset #0) | ■■■ | ECG Data (Decimated Dataset #5) |
|---|---|---|---|---|---|
| 1 byte | 1 byte | 2 bytes | | | |

1 sample for each of 9 channels
(LA, RA, LL, V1, V2, V3, V4, V5, V6)
(16 bits each, MSByte, LSByte))

ECG Data Packet for 4 channel ECG data (52 bytes total, describing 12 msec worth of data)

| ECG Pkt Identifier | Num of Chan 4 | ECG ID | ECG Data (Decimated Dataset #0) | ■■■ | ECG Data (Decimated Dataset #5) |
|---|---|---|---|---|---|
| 1 byte | 1 byte | 2 bytes | | | |

1 sample for each of 4 channels
(LA, RA, LL, C)
(16 bits each, MSByte, LSByte)

Snapshot Data Packet (196 bytes total, describing 2 msec worth of high-resolution data)

| Snapshot Pkt Identifier | ECG ID this is associated with | Offset (Which Dataset) | Snapshot Data (hi-res LA) | Snapshot Data (hi-res RA) | Snapshot Data (hi-res LL) |
|---|---|---|---|---|---|
| 1 byte | 2 byte | 1 bytes | 32 samples of high-resolution data for channel LA (16 bits each, MSByte, LSByte) | 32 samples of high-resolution data for channel RA (16 bits each, MSByte, LSByte) | 32 samples of high-resolution data for channel LL (16 bits each, MSByte, LSByte) |

FIG 22

WIRELESS ECG SYSTEM

CROSS-REFERENCE TO RELATED APPLICATIONS

This application is a continuation of and claims the benefit of the filing date pursuant to 35 U.S.C. §120 of application Ser. No. 10/439,356 for a WIRELESS ECG SYSTEM, filed May 16, 2003 and currently pending, which, in turn, claims the benefit of the filing date pursuant to 35 U.S.C. §120 of Application Ser. No. 60/392,882 for a FASTENER ASSEMBLY, filed Jul. 1, 2002. Application Ser. No. 10/439,356 is also a continuation-in-part of and claims the benefit of the filing date pursuant to 35 U.S.C. §120 of application Ser. No. 09/998,733 for a WIRELESS ECG SYSTEM, filed Nov. 30, 2001 and now patented, which, in turn, is a continuation-in-part of and claims the benefit of the filing date pursuant to 35 U.S.C. §120 of application Ser. No. 09/908,509 for a WIRELESS ELECTROCARDIOGRAPH SYSTEM AND METHOD, filed Jul. 17, 2001 and now patented. The disclosures and content of each of the above identified application are hereby incorporated by reference in their entireties.

FIELD OF THE INVENTION

The present invention relates to a wireless monitoring system and, more particularly, to a wireless monitoring system for monitoring physiological data.

BACKGROUND OF THE INVENTION

An electrocardiograph (ECG) system monitors heart electrical activity in a patient. Conventional ECG systems utilize electrodes or sensors placed on a patient in specific locations to detect electrical impulses generated by the heart during each beat. Typically, these electrical impulses or signals are detected by and directly transferred from the sensors or electrodes to a stationary ECG monitor via multiple cables or wires. The ECG monitor performs various signal processing and computational operations to convert the raw electrical signals into meaningful information that can be displayed on a monitor or printed out for review by a physician.

Doctors have used ECG systems to monitor heart activity for decades. Currently, there are several different systems that use ECG signals to monitor heart activity. These systems, however, are generally stationary and are not developed or suitable for portable use. While portable telemetry systems exist, they are not a direct replacement for stationary ECG monitors. Moreover, because conventional systems use multiple cables or wires, and are cumbersome and uncomfortable for the patient, and require a significant amount of set up time. Thus, a need exists for a wireless ECG system that solves the aforementioned problems. The present invention fills this need.

Furthermore, in both traditional wired systems and wireless systems, portions of the conventional electrodes or sensors that connect to the cables, wires, or chest assemblies are not standardized. In other words, the metal snap pieces or metal tabs that connect to the female portions of the cables, wires, or chest assemblies come in various sizes, shapes and configurations. Accordingly, many of the conventional electrodes or sensors are not compatible for use with many of the wires, leads, or chest assemblies used in physiological data collections systems.

To solve this problem, many conventional wired systems utilize spring loaded, female snap pieces, which are compatible with many different electrodes or sensors having male snap pieces or metal tabs. Those spring loaded, female snap pieces, however, are substantially more expensive than other conventional female snap pieces. Nevertheless, because the increased cost of the spring loaded, female snap pieces can be amortized over the life of the cable or lead set, the increased costs of those snap pieces are not a major consideration for conventional wired systems.

However, the increased costs of those female snap pieces cannot be amortized over the life of a chest assembly used in a typical wireless or telemetry system since the chest assemblies used in such systems are generally discarded after each patient use. Accordingly, the increased cost of those spring loaded, female snap pieces make them unsuitable for use with chest assemblies used in a wireless or telemetry system.

To avoid the incompatibility problems with conventional electrodes or sensors and the increased cost associated with spring loaded, female snap pieces, some wireless or telemetry systems use chest assemblies having integrated electrodes or sensors. A major disadvantage to such chest assemblies, however, is that those chest assemblies must be hermetically packaged to preserve the integrity of the aqueous silver chloride gel on the electrodes integrally connected to those chest assemblies. As a result, the cost of such chest assemblies is significant. Because those chest assemblies are designed to be disposed of after each patient use, the increased cost of those chest assemblies make them cost inefficient.

In addition, the spring loaded, female snap pieces and the metal snaps typically used with conventional electrodes or sensors are typically constructed of metal and are not radiolucent. Consequently, those snap pieces and metal snaps show up clearly on x-rays and other imaging procedures. Transparency to hospital imaging systems such as x-ray or fluoroscopes is desirable in many medical procedures such as are carried out in cardiac catheterization labs where conventional electrocardiograph electrodes and wires may obscure the view of internal blood vessels. Radiolucent electrodes are known in the art and are sold by companies such as Kendle and 3M. Non-disposable radiolucent electrode leads exist but cost in excess of a thousand dollars per radiolucent lead set.

Accordingly, there exists a need for a fastener assembly that is capable of connecting a disposable chest assembly to any conventional electrode or sensor, cost efficient, radiolucent and easy to use. The present invention fills this need.

BRIEF SUMMARY OF THE INVENTION

The present invention relates to a wireless ECG system that is universally compatible with existing or conventional ECG monitors. The ECG system generally comprises a chest assembly, a body electronics unit, and a base station. The chest assembly connects to electrodes specifically located on a patient's body for detecting electrical signals from the patient's heart. The electrical signals are detected by the chest assembly—thus, providing up to a "7 lead" analysis of the heart. Alternatively, the chest assembly can be augmented with a precordial assembly that connects to electrodes specifically located on the patient's body—thus, providing a "12 lead" analysis of the heart.

The electrical signals are transmitted through the chest assembly and/or the precordial assembly to the body electronics unit, which removably secures to the patient via an armband. The body electronics unit transmits the electrical signals to the base station via radio transmission. The base station contains terminals configured to attach to standard lead wires or cable. The base station transmits the electrical signals to a conventional ECG monitor via the standard lead wires or cables. In turn, the ECG monitor processes or transforms the electrical signals into meaningful information that can be displayed on the ECG monitor for review by a physician.

The ECG system eliminates the wires that ordinarily tether an ECG patent to an ECG monitor by replacing conventional wires with a radio link. The present invention is lightweight and portable—thereby providing increased comfort and mobility to the patient. In addition, the present invention requires decreased setup times and is more convenient for health practitioners to use than conventional ECG systems. In addition to collecting and transmitting ECG signals, the present invention is capable of collecting and transmitting other physiological data. For example, the body electronics unit is capable of transmitting and the base station is capable of receiving and processing physiological data pertaining to a patient's pulse, respiration rate, heart rate, temperature, blood pressure, EEG signals, and pulse oximeter signals, or the like.

In addition, the present invention relates to a fastener assembly for connecting a conventional electrode or sensor to a system for collecting physiological data from a patient. More particularly, the fastener assembly electrically connects the conventional electrode or sensor to an electrically conductive element or trace within the lead assembly. The electrically conductive element may be silver epoxy or any other suitable electrically conductive adhesive. The fastener assembly connects the electrodes or sensors to the electrically conductive element or trace at an electrode connection point. At the electrode connection point, the lead assembly has an aperture therethrough formed from a star cut pattern. The star cut pattern could be die cut, punched, laser cut or formed by other known means. The star cut pattern defines flaps that mechanically hold the electrode or sensor in the aperture and provide an electrical connection between the electrically conductive element or trace and the electrode or sensor upon insertion of the electrode or sensor in the aperture. Further, at each electrode connection point, the fastener assembly includes an electrode housing secured to the non-patient side of the lead assembly. The electrode housing is constructed of an elastomeric material bonded to the back surface of the lead assembly and contains a female void for receiving and removably securing a male portion of the electrode or sensor. In addition, at each electrode connection point, the chest assembly may optionally include an electrically conductive, adhesive layer for removably securing the electrode or sensor to the chest assembly and providing enhanced electrical connection between the electrically conductive element or trace and the electrode or sensor upon insertion of the electrode or sensor though the aperture.

In operation, the male portion of the electrode or sensor is inserted through the aperture starting at the patient side of the lead assembly. The flaps fanned by the aperture are deflected as the male portion of the electrode or sensor is inserted into the aperture. The resilience of the flaps cause the flaps to wipe against the male portion and mechanically hold the electrode or sensor in the aperture defined between the flaps. After passing though the aperture, the male portion is inserted into the female void contained in the electrode housing. The female void receives the male portion of the electrode or sensor and removably secures the electrode or sensor to the chest assembly. The elastomeric property of the electrode housing allows the female void to receive and secure electrodes or sensors having different shapes and sizes. The electrode or sensor is inserted into the aperture until the contact portion of the electrode or sensor (such as a male snap post) abuts or contacts the electrically conductive element in the lead assembly. The electrically conductive element in the lead assembly makes contact with the electrode or sensor and creates an electrical link between the electrode or sensor and the electrically conductive element or trace in the lead assembly. Optionally, electrically conductive adhesives may be added to either the lead assembly or the electrode housing to enhance the electrical connection. The fastener assembly of the present invention may be used to connect conventional electrodes or sensors to both traditional wired systems and wireless systems for collecting physiological data from a patient.

These as well as other novel advantages, details, embodiments, features, and objects of the present invention will be apparent to those skilled in the art from the following detailed description of the invention, the attached claims and accompanying drawings, listed herein below which are useful in explaining the invention.

BRIEF DESCRIPTION OF THE DRAWINGS

The foregoing aspects and many of the advantages of the present invention will become readily appreciated by reference to the following detailed description of the preferred embodiment, when taken in conjunction with the accompanying drawings, wherein:

FIG. 1 is a perspective view of an exemplary embodiment of the ECG system;

FIG. 2 is a cross sectional view of the chest assembly and the precordial assembly;

FIG. 3 is a top view of an exemplary embodiment of the chest assembly;

FIG. 4 is a top view of an exemplary embodiment of the precordial assembly;

FIG. 7 is a perspective view of an exemplary embodiment of the body electronics unit;

FIG. 11A is an exemplary embodiment of the user interface of the base station;

FIG. 12 is a block diagram of an exemplary embodiment of the receiver;

FIG. 14 is an exemplary embodiment of the adaptor assembly;

FIG. 15 is another exemplary embodiment of the adaptor assembly;

FIG. 16 is another exemplary embodiment of the adaptor assembly;

FIG. 17 is a flow chart of an exemplary embodiment for operation of the ECG system;

FIG. 22 depicts the raw data set and the snapshot data set packaged into raw data packets and snapshot data packets;

DESCRIPTION OF THE PREFERRED EMBODIMENT

Figure 2A:
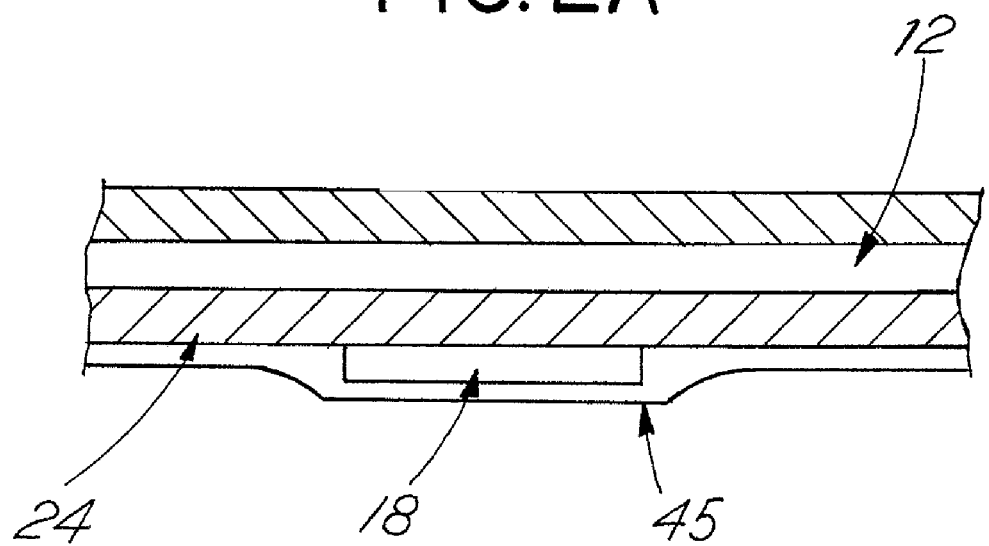
FIG. 2A is a cross sectional view of an exemplary embodiment of the chest assembly.

For a better understanding of the present invention, reference may be had to the following detailed description taken in conjunction with the appended claims and accompanying drawings. Briefly, the present invention relates to a wireless, portable ECG system. Referring to FIG. 1, the ECG system 10 comprises a chest assembly 12, a body electronics unit 14, and a base station 16.

The chest assembly 12 is a one-piece flexible circuit that connects a plurality of electrode connectors 18. The electrode connectors 18 are configured to connect to electrodes 20 or electrically conductive adhesives. Preferably, the electrode connectors 18 have snap terminals that connect to electrodes 20 having snap terminals. Each electrode connector 18 connects to an electrically conductive element or trace for transmitting electrical signals. The electrically conductive elements or traces run along the chest assembly 12 and connect to a chest assembly connector 21.

Alternatively, the chest assembly 12 may be constructed with electrode conductors, instead of electrode connectors. In such an embodiment, each electrode conductor will have a flat, conductive surface. Electrodes having flat conductive surfaces may be coupled to the electrode conductors via a suitable adhesive. Thus, electrodes can be attached to the chest assembly by "sticking" an electrode to each electrode conductor.

Referring to FIG. 2, the chest assembly 12 may have outer layers 22, 24 that are constructed of a lightweight and reasonably moisture resistant material, such as DuPont Sontara® or other suitable fabric. The chest assembly 12 may be constructed with only one outer layer or no outer layers without departing from the spirit and scope of the invention. Moreover, if the chest assembly is constructed with just one outer layer, that outer layer can be on either side of the chest assembly 12 without departing from the spirit and scope of the invention. Adhesive layers 26, 28 secure insulating layers 30, 32 to the outer layers 22, 24 respectively. Insulating layers 30, 32 may be constructed of Mylar® (polyester) film or other suitable insulating material. Adhesive layers 34, 36 secure the insulating layers 30, 32 to a base layer 38. The base layer 38 is preferably constructed of Mylar film and has a first side 40 and a second side 42. The electrically conductive elements or traces that connect to the electrode connectors 18 may be located on the first side 40 of the base layer 38. One such conductive element or trace is shown at 39. A shielding layer 44 for reducing any external inferences or radio frequency noise with the chest assembly 12 may be located on the second side 42 of the base layer 38. The shielding layer 44 may be constructed of single or multiple layers of dielectric, or electrically or magnetically conductive material. Of course, the chest assembly 12 may be constructed without a shielding layer 44 without departing from the spirit and scope of the invention. Typically, a shielding layer 44 will be necessary in "noisy" environments. The shielding layer preferably comprises an X-patterned grid. The back of the electrode connector 18 may also be covered with Mylar to further insulate the chest assembly 12 and prevent an externally applied electric potential from entering the ECG system.

Referring to FIG. 2A, the chest assembly 12 may be constructed with an adhesive sheet 45 that partially or completely covers the chest assembly 12. The electrode connectors 18 may be sandwiched between the adhesive sheet 45 and the outer layer 24 of the chest assembly 12. Alternatively, electrode conductors may be used instead of electrodes connectors 18. Preferably, the adhesive sheet 45 is constructed of polymers that have isotropic electrical conductive properties and/or anisotropic electrical conductive properties such that the regional specific impedance through the adhesive sheet 45 is less than in a laterally oriented dimension direction. The polymers are preferably hydropolymers, which are electrically conductive, relatively nonirritating to a patient's skin, and demonstrate excellent adhesive qualities. Suitable hydropolymer sheets for use with the present invention are available from Promeon of Boston, Mass., under the product designation RG-60 Series Hyrogels. In another exemplary embodiment, the adhesive having isotropic electrical conductive properties and/or anisotropic electrical conductive properties could be applied to the electrode connector 18 or the electrode conductor just prior to the attachment of the electrode 20 to the chest assembly 12. The adhesive could be applied between the electrode connector 18 (electrode conductor) and the electrode 20 or to the side of the electrode 20 that contacts or connects to the patient. In such an embodiment, the chest assembly 12 would not be manufactured with an adhesive sheet 45. Instead, the health care provider would apply the adhesive to the electrode connector 18 (electrode conductor) and/or electrode 20 just prior to attaching the chest assembly 12 to the patient.

Figure 28:
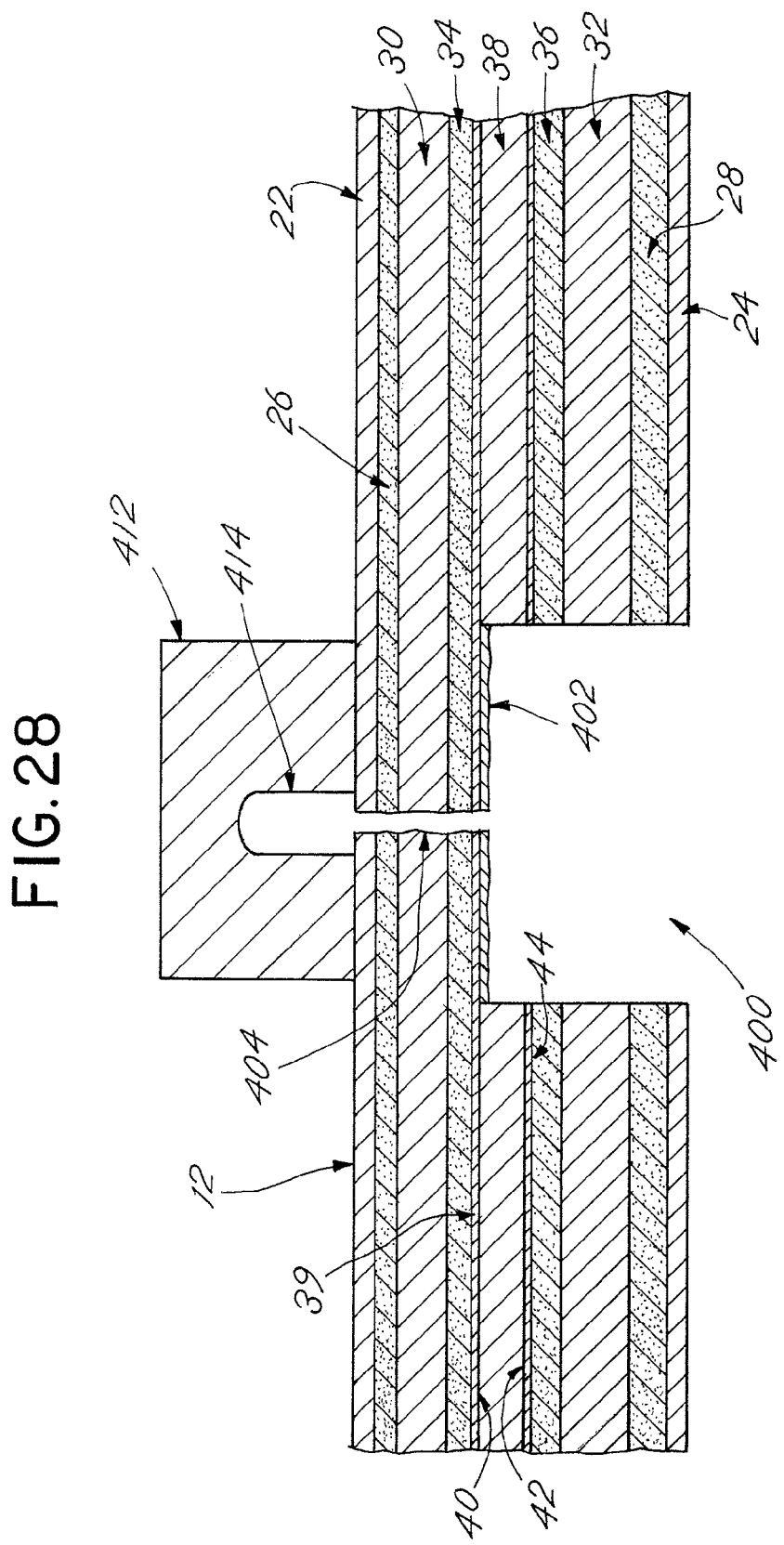
FIG. 28 is a cross sectional view of an exemplary embodiment of chest assembly having an electrode housing.
Figure 29:
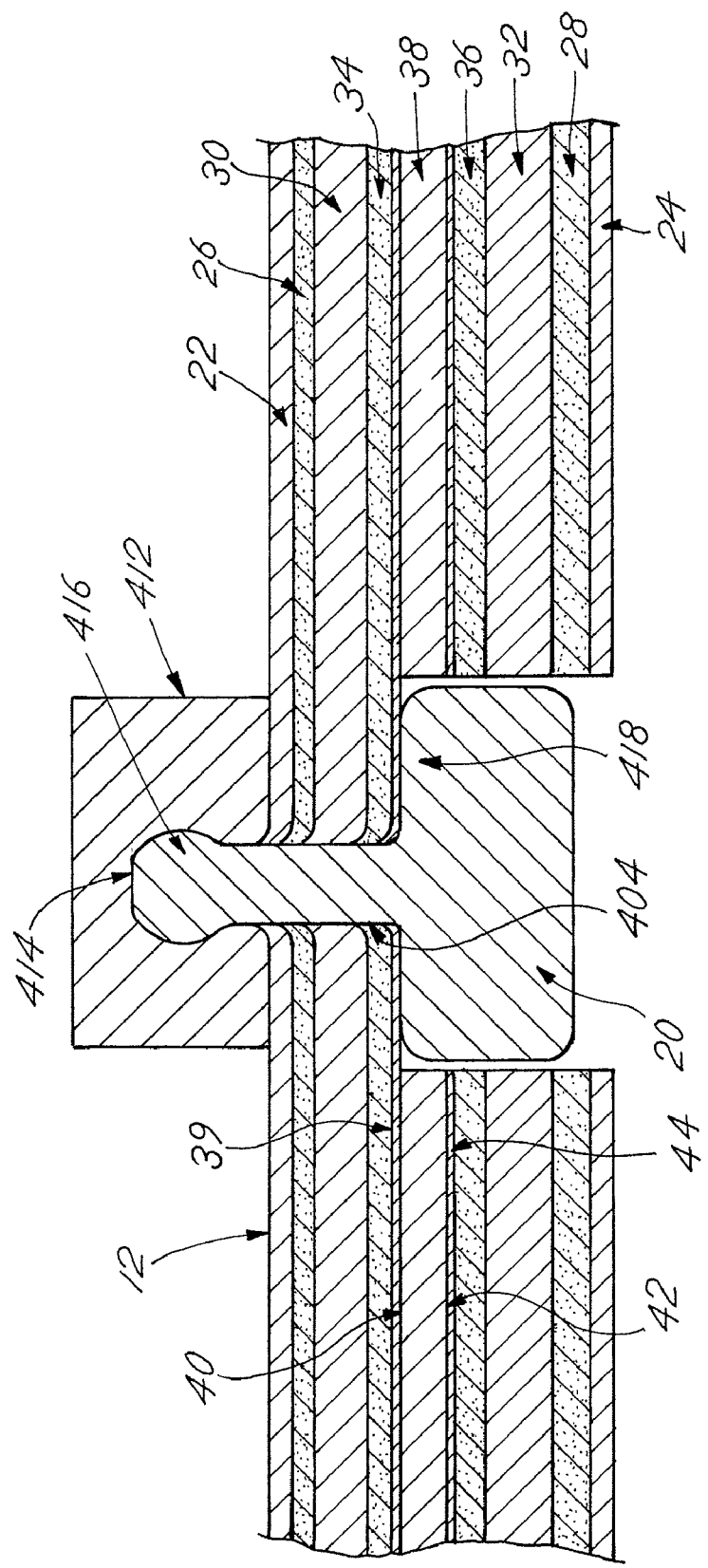
FIG. 29 is a cross sectional view of an exemplary embodiment of chest assembly having an electrode housing and coupled to an electrode.

In an alternative embodiment, the chest assembly 12 may be constructed to connect to any conventional electrode or sensor. More specifically, as shown in FIGS. 28-29, at each point (i.e., connection point 400) where an electrode or sensor connects to the chest assembly 12, portions of the layers of the chest assembly 12 that reside on the patient side are removed or are not applied during manufacture and the first side 40 of the base layer 38 containing the electrically conductive element or trace 39 is exposed. At each electrode or sensor connection point 400, the chest assembly 12 optionally includes an electrically conductive layer 402 adhered to the electrically conductive element or trace 39. The optional electrical adhesive layer 402 may be a layer of silver epoxy or other suitable electrically conductive, adhesive material capable of adhering or securing the electrode or sensor to the chest assembly 12 and providing an electrical link between the electrode or sensor with the electrically conductive element or trace 39.

Figure 32A:
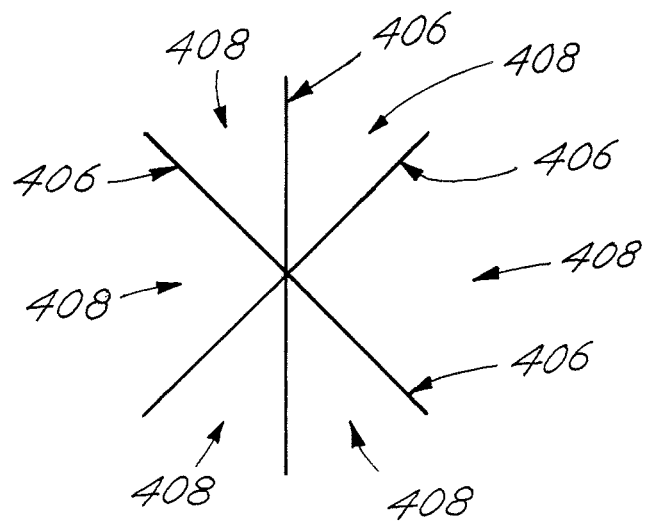
FIGS. 32A-E depict exemplary embodiments of an aperture formed in a chest assembly for receiving an electrode.
Figure 32B:
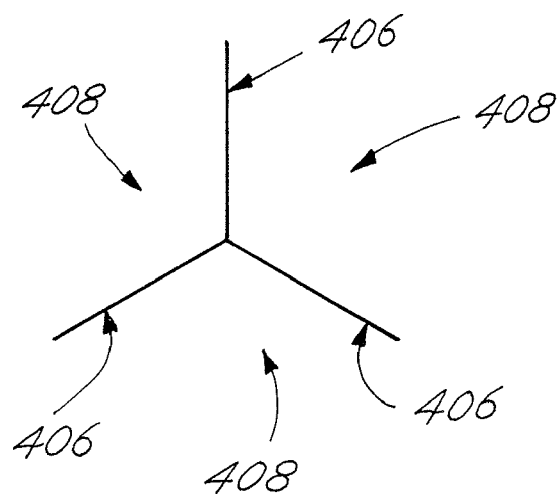
Figure 32C:
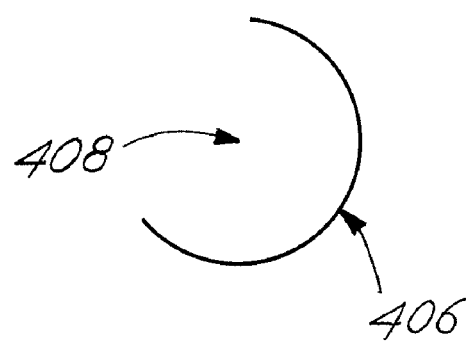
Figure 32D:
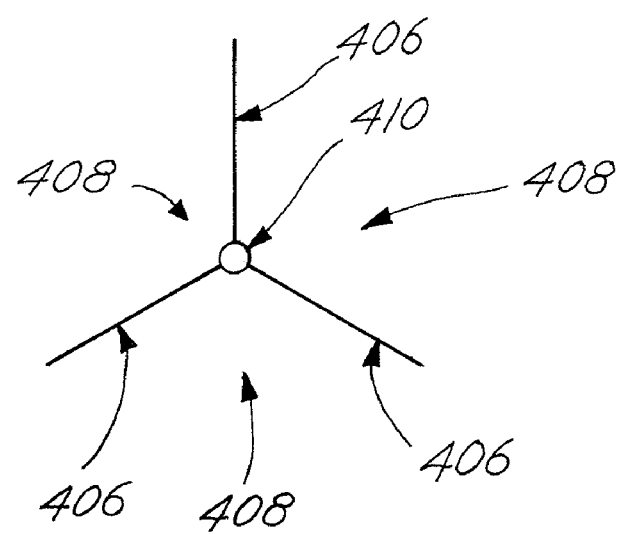
Figure 32E:
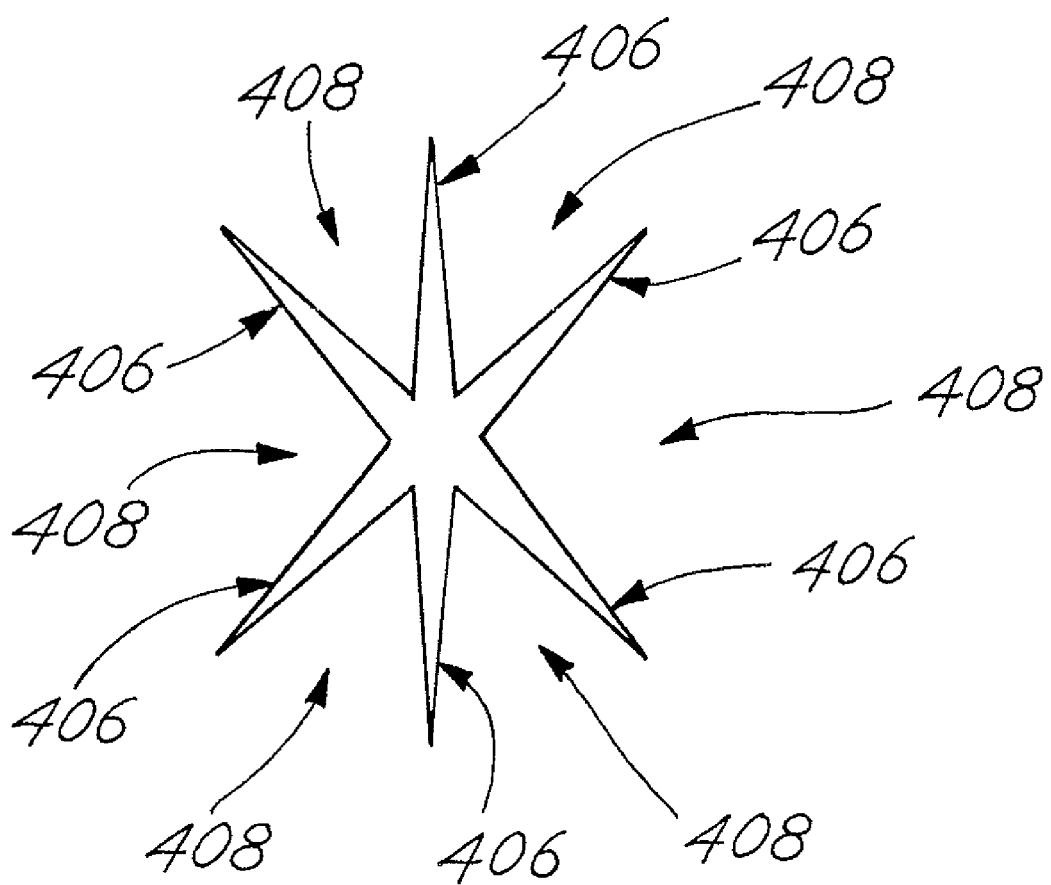

In addition, at each electrode or sensor connection point 400, the chest assembly 12 includes an aperture 404 formed therethrough. As shown in FIG. 32A, the aperture 404 may be defined by a star cut pattern in the form of an asterisk with six legs 406 cut through each layer of the lead assembly 12. Each corresponding adjacent legs 406 define a flap 408. The aperture 404 may be cut in various shapes and configurations without departing from the scope and spirit of the invention. For example, as shown in FIG. 32B, the aperture 404 formed may be defined by three flaps 408. Further, as shown in FIG. 32C, the aperture 404 may be defined by a semi-circular cut through the chest assembly 12, which forms one flap 408. In addition, as shown in FIG. 32D, the aperture 404 may be defined by three flaps 408 and an open passage 410 formed where the three flaps 408 contact each other. Moreover, as shown in FIG. 32E, the aperture 404 may be defined by a star cut pattern with spacing between adjacent flaps 408.

Referring back to FIGS. 28-29, at each electrode or sensor connection point 400, the chest assembly 12 includes an electrode housing 412 on the non-patient side of the chest assembly 16. The electrode housing 412 may be constructed from an elastomeric rubber, or any other suitable elastomeric or plastic material. The electrode housing 412 may be thermally bonded to the chest assembly 12 or adhered to the chest assembly 12 with any suitable adhesive. The electrode housing 412 contains an appropriately sized female void 414 for receiving the male portion 416 of any conventional electrode or sensor 20. The electrode housing 412 should be constructed from a suitable elastomeric material so that the female void 414 will conform to different male portions 416 of different shapes and sizes when such male portions 416 are inserted into the female void 414. Accordingly, upon insertion of the male portion 416, the female void 414 conforms such that the male portion 416 is removably secured in the female void 414. Because of the aforementioned design and configuration of the chest assembly, the chest assembly can be used with many different electrodes or sensors 20 that are used in the healthcare industry. In addition, to aid the health care provider in attaching the chest assembly 12 to the patient, each electrode housing 412 is preferably appropriately color coded and/or contains alphameric designations to correspond to the particular electrode or sensor 20 attached to that electrode housing 412. For example, the electrode housings 412 may be labeled RL, LA, LL, RA, or V when the chest assembly is intended for ECG use. In yet another embodiment the electrode housing 412 is not bonded to the chest assembly 20 but is provided separately. In such an embodiment, the technician or health care provider setting up the equipment would press on the separate electrode housings 412 when attaching the chest assembly 12 to the electrode or sensor 20.

To connect a conventional electrode or sensor 20, the male portion 416 of an electrode or sensor 20 is inserted or positioned through the aperture 404. As the electrode or sensor 20 is inserted through the aperture 404, the male portion 416 of the electrode or sensor 20 deflects the flaps 408. The resilience of the flaps 408 cause the flaps 408 to wipe against the male portion 416 and mechanically hold the electrode or sensor 20 in the aperture 404 defined between the flaps 408. The pattern of the aperture 404 allows for the deflection of the flaps 408 with minimal force applied during the insertion of the male portion 416 of the electrode or sensor 20. The male portion 416 of the electrode or sensor 20 causes deflection of the flaps 408 without placing undue stresses on the ends of the flaps 408 which could otherwise result in the flaps being torn or losing their resilient property. In addition, because the aperture 404 is formed through the electrically conductive element or trace 39, electrical conductivity is obtained when the electrode or sensor 20 contacts the flaps 408. Further, when the electrode or sensor 20 contacts electrically conductive elements or trace 39 via the flaps 408, the electrical signals corresponding to physiological data of the patient pass from the electrode or sensor 20 to the electrically conductive element or trace 39, which, in turn, conveys the data to the body electronics unit 14.

The electrode or sensor 20 is inserted or positioned through the aperture 404 so that a base portion 418 of the electrode or sensor 20 firmly abuts or contacts the electrically conductive elements or trace 39. Thus, the electrical signals corresponding to physiological data of the patient pass from the electrode or sensor 20 to the electrically conductive element or trace 39, which, in turn, conveys the data to the remote body electronics unit 14. Optionally an electrically layer or adhesive 402 may be used to enhance the mechanical and/or electrical connection.

Figure 30:
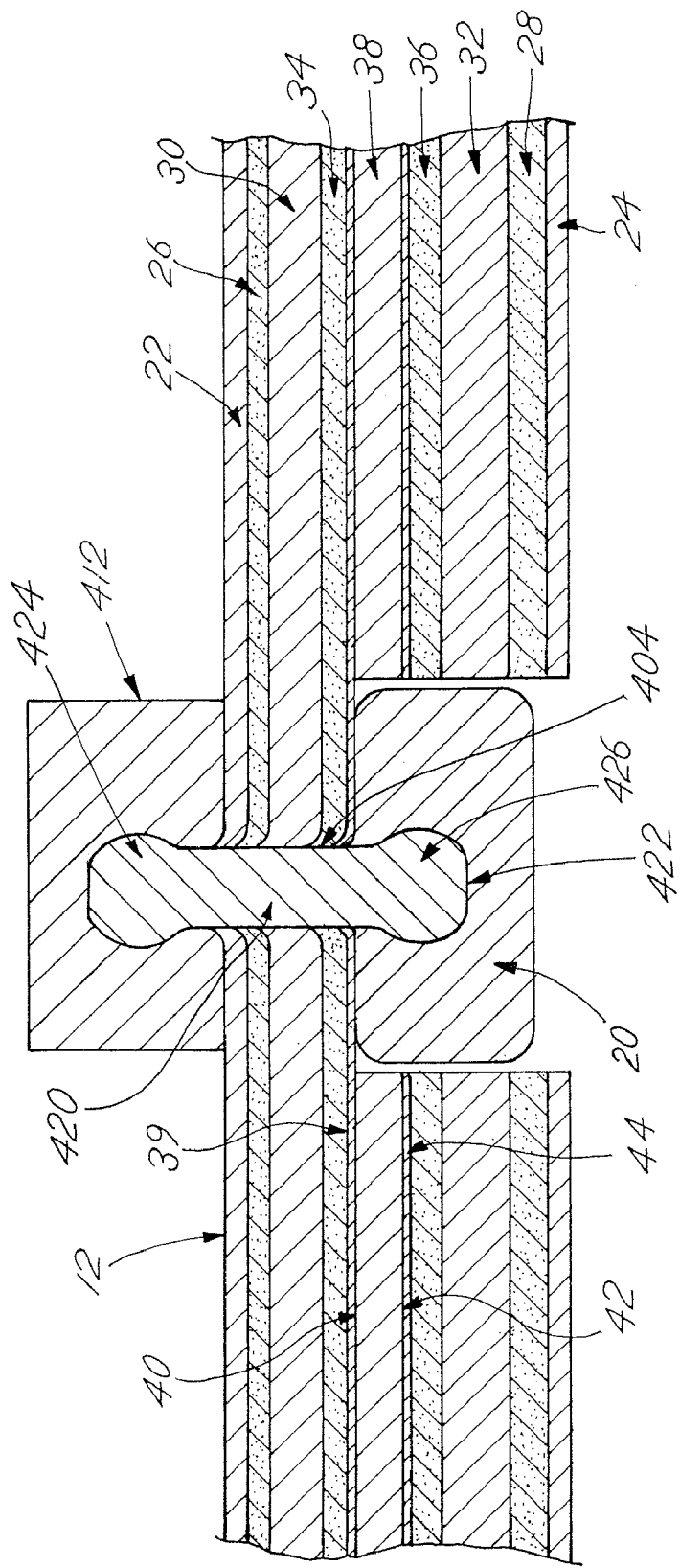
FIG. 30 is a cross sectional view of another exemplary embodiment of chest assembly having an electrode housing and coupled to an electrode.
Figure 31:
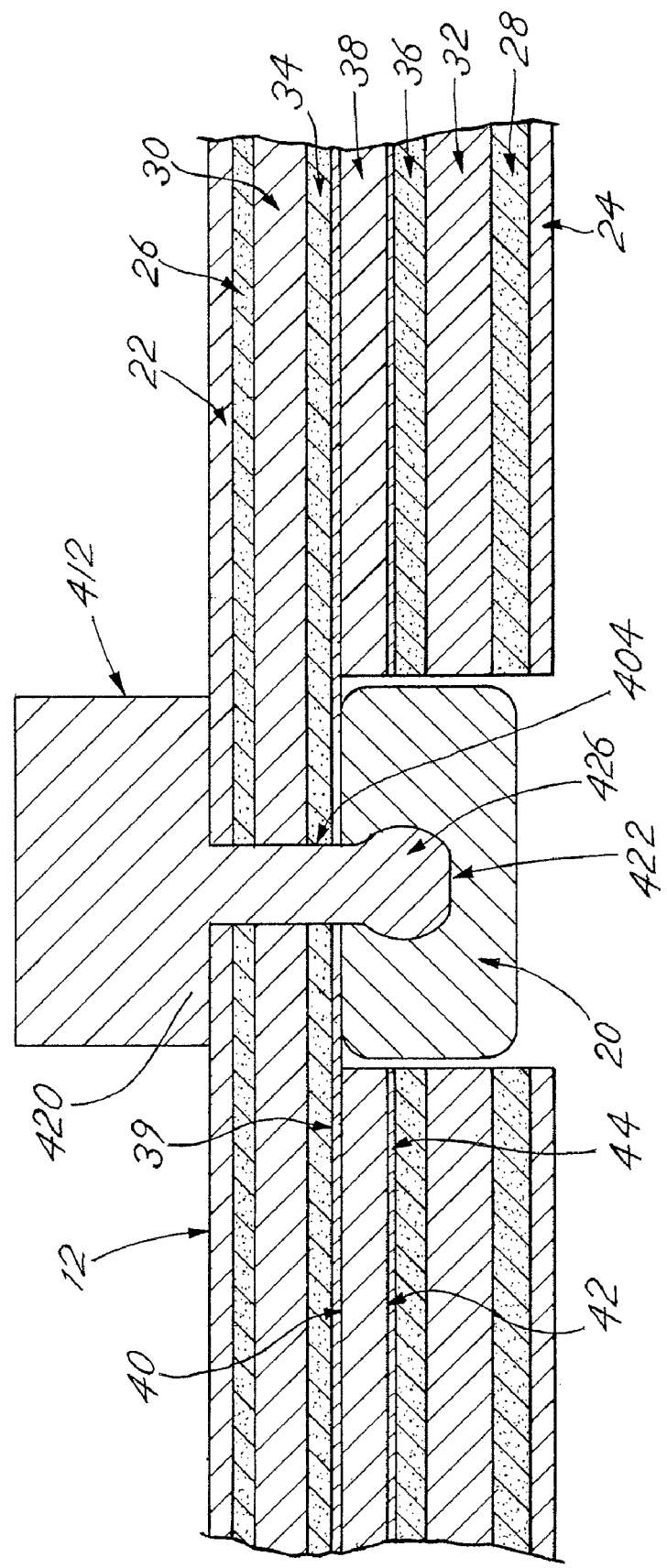
FIG. 31 is a cross sectional view of another exemplary embodiment of chest assembly having an electrode housing and coupled to an electrode.

In another embodiment, as shown in FIG. 30, the chest assembly 12 may be constructed such that a conductive male connector 420 to connect a conventional electrode or sensor 20 that has a female receptacle or void 422, instead of a male portion 416 (as shown in FIG. 29). To connect the conventional electrode or sensor 20 having the female receptacle or void 422, the conductive male connector 420 is inserted through the aperture 404 until a first male member 424 is removably secured in the electrode housing 412. The conductive male connector 420 contacts the electrically conductive element or trace 39 upon insertion. The electrode or sensor 20 having the female receptacle or void 422 is then removably connected to a second male member 426. Alternatively, as shown in FIG. 31, the male conductive connector 420 may be integrally connected or fixedly secured to the electrode housing 412. In such an embodiment, the electrode housing 412 would not be constructed of elastomeric material and would not contain the female void 424 (shown in FIGS. 28-30). In either case, the electrical signals corresponding to physiological data of the patient pass from the electrode or sensor 20 to the conductive male connector 420 and to the electrically conductive element or trace 39.

Preferably, the chest assembly 12 and the electrodes or sensor used with the chest assembly are constructed of radiolucent materials. Radiolucent electrodes are known in the art and are sold by companies such as Kendle and 3M. In addition, the chest assembly 12 is designed and configured to be used only a few times before being disposed. Accordingly, the chest assembly 12 is preferably constructed such that the electrodes or sensors 20 can be connected to and disconnected from the chest assembly 12 only a limited amount of times before the connection between the chest assembly 12 and the electrodes or sensor 20 becomes unusable and the chest assembly 12 must be discarded. For example, repeated use of the connection and disconnection of the electrodes or sensors 20 to and from the chest assembly 12 may cause the electrically conductive element or trace 39 to abrade or wear, the flaps 408 to lose their resilient property, or the elastomeric material defining the female void 414 to become overly stretched by the male portion 416. A disposable chest assembly 12 has many advantages. For example, disposable chest assemblies using the present invention offer hygienic advantages since such chest assemblies will be disposed of after each patient use—thus, reducing the spread of infection or disease. Further, lead assemblies of the present design may be made radiolucent by selection of appropriate materials thereby enabling their use in medical procedures where traditional snaps would interfere with imaging equipment. Further, the materials used to construct a disposable chest assembly, which uses the present invention are significantly less expensive than the materials used on other known disposable systems. Thus, the fastener assembly of the present invention makes a disposable chest assembly very cost effective compared to other known disposable systems.

Referring back to FIG. 1, the chest assembly 12 is capable of attaching to five electrodes 20 and provides a means for generally positioning the electrodes on the patient, thereby providing up to a "7 lead" analysis of the electrical activity of the heart. The electrode connectors 18 are preferably labeled and color-coded to ensure that the chest assembly 12 is properly positioned on the patient and connected to the appropriate electrodes 20. For instance, the electrode connectors are preferably labeled RL, LA, LL, RA, and V, respectively. The chest assembly 12 is constructed such that the RA electrode connector is connected to an electrode positioned on the right side of the patient's chest about level of the first and second intercostal space, the LA electrode connector is connected to an electrode positioned on the left side of the patient's chest about level of the first and second intercostal space, the RL and LL electrode connectors are connected to electrodes positioned on the left side of the patient's torso, and the V electrode connector is connected to an electrode positioned in the middle of the patient's chest about level of the fourth and fifth intercostal space. The chest assembly 12 is preferably designed such that it is centered on the chest below the patient's clavicle.

Referring to FIG. 3, the chest assembly 12 is configured to provide flexible positioning of the chest assembly 12 on the patient. FIG. 3 is for illustrative purposes only, and thus, the chest assembly 12, as depicted in FIG. 3, is not limited to any particular shape or configuration. The chest assembly 12 has a linear section or tail 46 extending from the chest assembly connector 21. The tail 46 flows into an electrode retaining section 47. The electrode retaining section 47 has an arcuate section 48. A first expandable arm 50 attaches to the arcuate section 48. The RA electrode connector 18a attaches to the first expandable arm 50. The arcuate section 48 flows into a transition section 52. The LA electrode connector 18b attaches to the transition section 52. The transition section 52 flows into a linear run 54. The RL electrode connector 18c attaches to the linear run 54. A second expandable arm 56 and an extension arm 58 attach to the linear run 54. The V electrode connector 18d attaches to the second extension arm 58 and the LL electrode connector 18e attaches to the second expandable arm 56.

The expandable arms 50, 56 are die cut in a serpentine pattern. The expandable arms 50, 56 comprise polypropylene or polyethylene fabric, Kapton, Mylar, or other flexible, memoryless material. The expandable arms 50, 56 expand, if necessary, by elongating the serpentine pattern. When expanded, a portion or all of the expandable arm is extended. Where only a portion of the expandable arm is extended, another portion remains folded. The expandable arms 50, 56 allow for extension as needed so that the chest assembly 12 can fit patients of various sizes and also allow for patient movement when the patient is wearing the chest assembly 12. The extension arm 58 allows for flexible positioning of the V electrode connector in the middle of the patient's chest such as placement at electrode position VI, V2 or V3. In some instances, the health care practitioner may desire not to utilize the extension arm 58 for taking electrocardiograph measurements. Thus, to keep the extension arm 58 secured to the linear run 58 and to ensure that the extension arm 58 will not interfere with the placement and positioning of the chest assembly 12, the extension arm 58 is die cut with a perforated seam that connects the extension arm 58 and the linear run 54 along the length of the extension arm 58. If the health care practitioner desires to use the extension arm 58, the perforated seam is unbroken so that the extension arm 58 can be selectively positioned on the patient's chest.

Figure 3A:
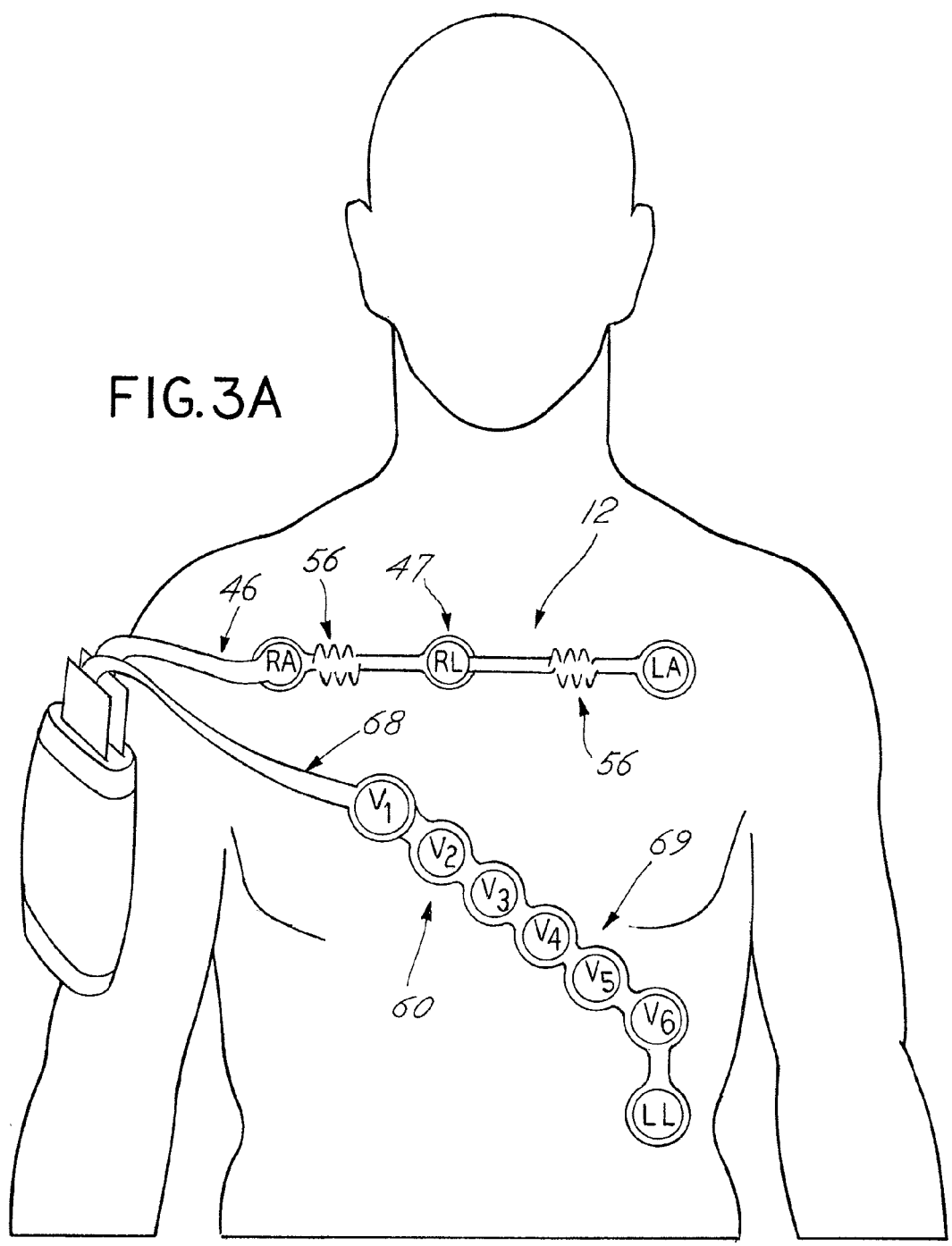
FIG. 3A depicts another exemplary embodiment of the chest assembly and the precordial assembly.

In another alternative embodiment shown in FIG. 3A, the chest assembly 12 may be configured such that the electrodes labeled RL, LA, and RA can be positioned straight across the patient's chest. Such an embodiment is preferably used on an "out-patient" basis. The chest assembly 12 shown in FIG. 3A has a tail 46 that flows into an electrode retaining section 47. The electrode retaining section may be configured to attach to three electrodes, namely the RL, LA, and RA electrodes. Preferably, the RL electrode is positioned between the LA and RA electrodes. Expandable arms 56 connect the LA and RA electrodes to the RL electrode and allow for extension as needed so that the chest assembly 12 can fit patients of various sizes and also allow for patient movement when the patient is wearing the chest assembly.

Referring to FIG. 1, the chest assembly 12 can be used with a precordial assembly 60 to provide a "12-lead" analysis of the electrical activity of the heart. Similar to the chest assembly 12, the precordial assembly 60 is a one-piece flexible circuit that connects a plurality of electrode connectors 62. The electrode connectors 62 have releasable connections that connect to electrodes. Preferably, the electrode connectors 62 have snap terminals that connect to electrodes having snap terminals. Each electrode connector 62 connects to an electrically conductive element or trace for transmitting electrical signals from a patient's heart. The electrically conductive elements or traces run along the precordial assembly 60 and connect to a precordial assembly connector 66. The precordial assembly 60 may be constructed similarly to the chest assembly 12 discussed above.

The precordial assembly 60 is capable of attaching to six electrodes selectively positioned on the abdomen and middle chest of the patient. The electrode connectors 62 of the precordial assembly 60 are preferably labeled and color-coded so as to prevent a health care provider from applying or positioning the precordial assembly onto the patient improperly. For instance, the electrode connectors 62 are preferably labeled VI, V2, V3, V4, V5, and V6, respectively. When the precordial assembly 60 is used, the V electrode connector on the chest assembly 12 is removed from its electrode and replaced with an electrode connector on the precordial assembly 60.

As shown in FIG. 4, the precordial assembly 60 is configured to provide flexible positioning of the precordial assembly 60 on the patient. FIG. 4 is for illustrative purposes only, and thus, the precordial assembly 60, as depicted in FIG. 4, is not limited to any particular shape or configuration. The precordial assembly has a linear section or tail 68 extending from the precordial assembly connector 66. The linear section or tail 68 flows into an electrode retaining section 69. The electrode retaining section 69 has a first arcuate section 70 having a first transition section 72. The V2 electrode connector 62b attaches to the first transition section 72. The VI electrode connector 62a attaches to a first extension arm 74 connected to the first transition section 72. A second arcuate section 76 extends from the first transition section 72. A second transition section 78 abuts the second arcuate section 76 and the V4 electrode connector 62d attaches to the second transition section 76. The V3 electrode connector 62c attaches to a second extension arm 80 connected to the second transition section 78. A third arcuate section 82 flows from the second transition section 78. The third arcuate section 82 abuts a third transition section 84. The V5 electrode connector 62e attaches to the third transition section 84. A fourth arcuate section 86 extends from the third transition section 84. The V6 electrode connector 62f attaches to the fourth arcuate section 86. The configuration of the precordial assembly 60 allows the health care provider or physician to flexibly position the electrode connectors 62 as needed to properly situate the precordial assembly 60 on the patient and to allow for patient movement when the patient is wearing the precordial assembly 60.

In another alternative embodiment shown in FIG. 3A, the precordial assembly 60 may be configured such that the electrodes labeled $V_1$-$V_6$ can be diagonally positioned in a row across the patient's chest. Such an embodiment is preferably used on an "out-patient" basis. The precordial assembly 60 shown in FIG. 3A has tail 68 that flows into an electrode retaining section 69. The electrode retaining section may be configured such that the LL electrode is located at the end of the diagonal line formed by the $V_1$-$V_6$ electrodes.

In operation, the chest assembly 12 and the precordial assembly 60 detect electrical signals generated by the heart during each beat and transfer these signals to the body electronics unit 14. When the system is operating in "7 lead" mode (i.e., when only the chest assembly 12 is being used) the body electronics unit 14 acquires signals from the RL, RA, LL, LA, and V electrodes. The body electronics unit 14 uses the RL electrode as a ground reference. When the system is operating in the "12 lead" mode (i.e., the chest assembly 12 and the precordial assembly 60 are being used) the body electronics unit 14 acquires signals from the RL, RA, LL, and LA electrodes via the chest assembly 12 and acquires signals from the VI, V2, V3, V4, V5, and V6 electrodes via the precordial assembly 60. Alternatively, a various number of electrodes may be monitored by the system. For example, the health care provider or physician may choose to use only two electrodes to monitor the heart, seven electrodes to monitor the heart, or the like. In other words, the present system is not limited to performing a "7 lead" and "12 lead" analysis of the heart. In addition to detecting electrical signals from the heart, the chest assembly 12 and the precordial assembly 60 may be constructed to detect other vital signs of the patient, for example, pulse, respiration rate, heart rate, temperature, blood pressure, EEG signals, and pulse oximeter signals.

Figure 5:
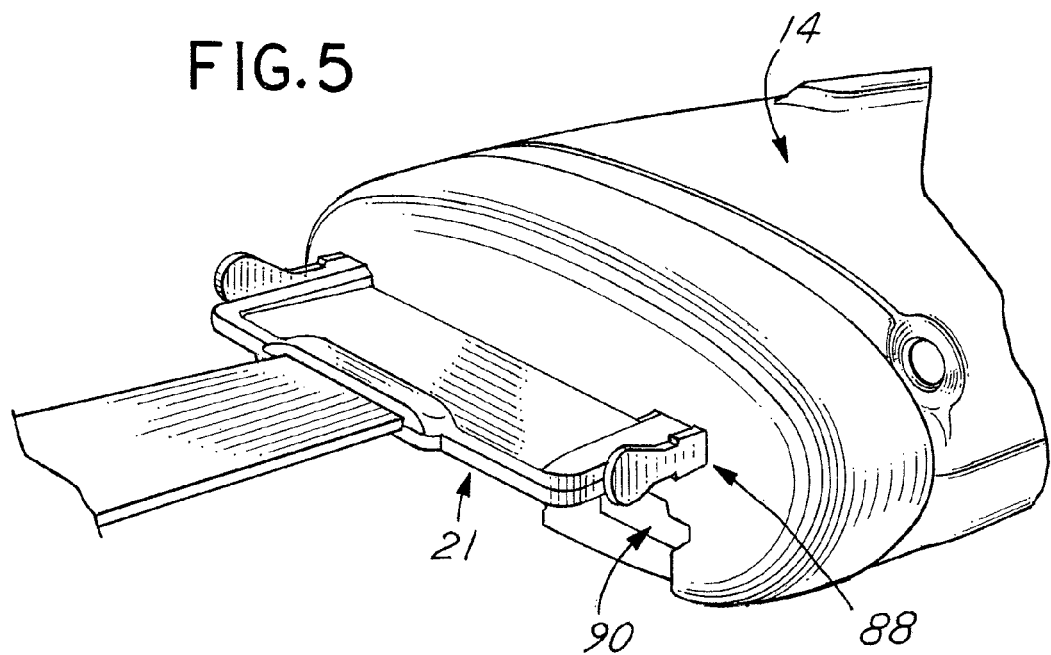
FIG. 5 is a perspective view of an exemplary embodiment of the body electronics unit.

Referring to FIG. 5, the chest assembly 12 connects to the body electronics unit 14 via a chest assembly connector 21. Specifically, the chest assembly connector 21 inserts into a chest assembly port 88 located in the body electronics unit 14. Similarly, the precordial assembly 60 (not shown) connects to the body electronics unit 14 via the precordial assembly connector 66 (not shown). Specifically, the precordial assembly connector 66 (not shown) inserts into a precordial assembly port 90. Resisters are connected to the chest assembly port 88 and the precordial assembly port 90 to prevent excessive electrical current from entering the body electronics unit 14—thereby ensuring that the body electronics unit 14 continues to operate properly in the presence a strong electrical current caused by a defibrillator (i.e., a 5 kV defibrillation excitation). The chest assembly connector 21 and the precordial assembly connector 66 are specifically keyed or configured to prevent the assembly connectors 21, 66 from being inserted into the assembly ports 88, 90 backwards, misaligned or otherwise improperly. Moreover, the chest assembly connector 21 is keyed or configured such that it is not compatible with the precordial assembly port 90. Likewise, the precordial assembly connector 66 is keyed or configured such that it is not compatible with the chest assembly port 88. Specifically, the chest assembly connector 21 has tongues specifically configured or arranged to fit into corresponding grooves of the chest assembly port 88. Accordingly, the chest assembly connector 21 can only be connected to the chest assembly port 88 in one orientation. For example, if the tongues are not aligned with the grooves, the chest assembly connector 21 will not couple to the chest assembly port 88. Likewise, the precordial assembly connector 66 has tongues specifically configured or arranged to fit into corresponding grooves of the precordial assembly port 90.

Figure 6:
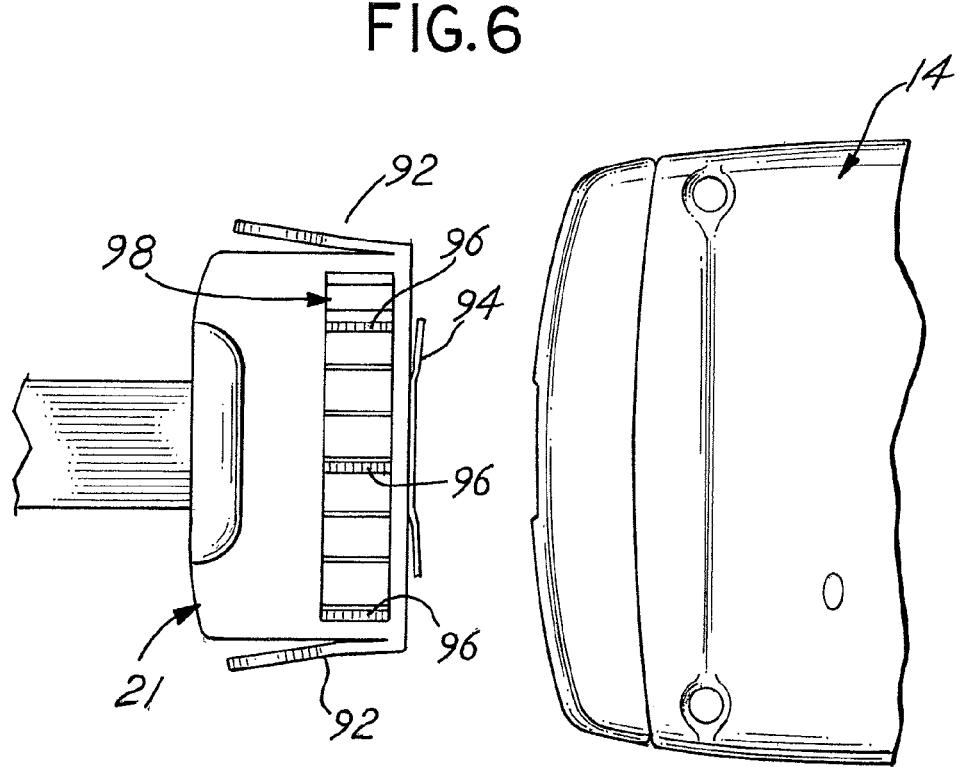
FIG. 6 is a top view of an exemplary embodiment of the assembly connectors.

As shown in FIG. 6, the chest assembly connector 21 and the precordial assembly connector 66 (not shown) have retaining clips or flanges 92 located on the sides of the connectors 21, 66 for removably securing the connectors 21, 66 into the assembly ports 88, 90. However, other means may be used to removably secure the connectors 21, 66 in the assembly ports 88, 90, such as screws, pins or the like. In addition, the assembly connectors 21, 66 may have spring flanges or clips 94 located at the tip of the connectors 21, 66 for providing a bias or tension against the assembly ports 88, 90. The spring flanges or clips 94 provide the connectors 21, 66 with a secure fit within the assembly ports 88, 90, thereby reducing any play or movement of the connectors 21, 66 within the assembly ports 88, 90. The electrically conductive elements or traces are specifically configured on the connectors 21, 66 so as to ensure that the electrical signals from the heart are properly transmitted to the body electronics unit 14. In other words, the electrically conductive elements or traces must be sufficiently spaced apart or otherwise isolated in some manner to prevent arcing across the electrically conductive elements. In addition, the spacing of the electrically conductive elements or traces permits the chest assembly and the precordial assembly to withstand defibrillation shock. Furthermore, the connectors 21, 66 have ribs 96 for preventing the electrically conductive elements or traces from coming into contact with metal objects or the like when the connectors 21, 66 are not inserted into the assembly ports 88, 90.

The chest assembly connector 21 may have a sensor pin or ground pin 98 that completes a circuit within the body electronics unit 14 when the chest assembly connector 21 is plugged into the chest assembly port 88, thereby activating the power and bringing the body electronic unit 14 out of "sleep mode." The sensor pin has specific tongue that corresponds and fits into a groove located in the chest assembly port 88. The sensor pin 98 serves as a means for the body electronics unit 14 to identify the chest assembly 12 and to prevent the use of other chest assemblies or electrocardiograph wearables that are not designed to be used with the on-body electronic unit 14. In other words, the power of the body electronics unit 14 will not activate unless the body electronics unit 14 identifies or recognizes the sensor pin 98 of the chest assembly 12. Likewise, the precordial assembly connector 66 may also have a sensor pin or ground pin 98. Alternatively, the body electronics unit 14 may have a power activation switch to turn the power "on" and "off" independent of any sensor pin configuration.

Figure 7A:
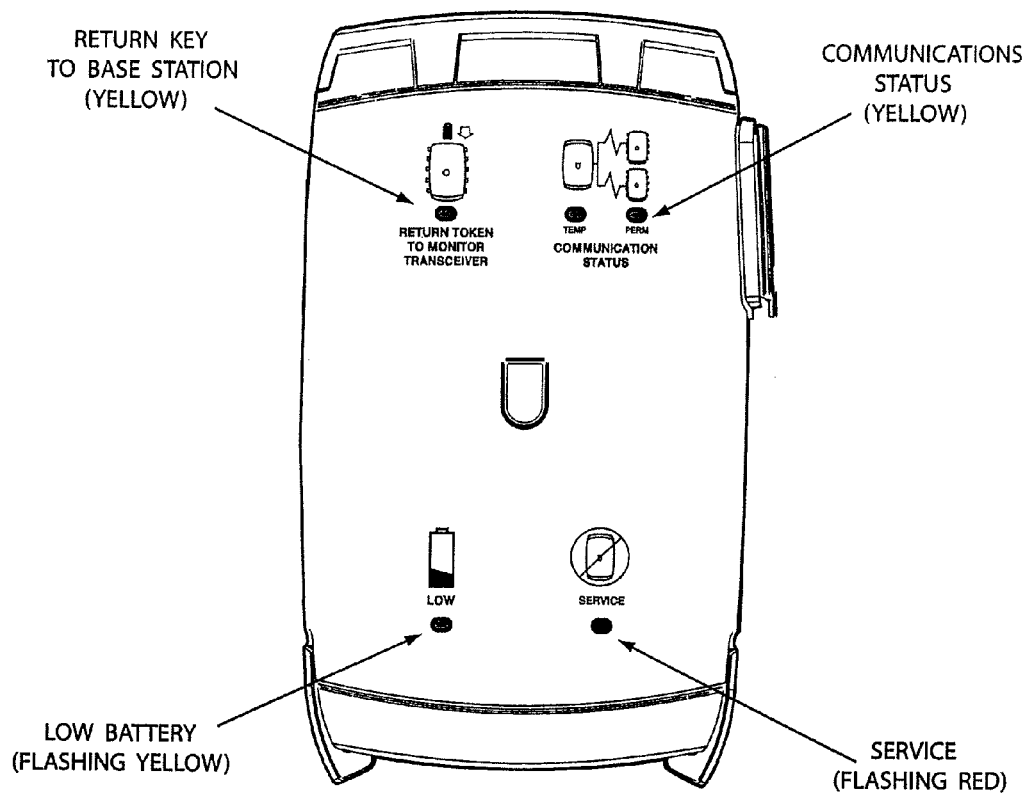
FIG. 7A is an exemplary embodiment of the user interface of the electronics body unit.

The outside casing of the body electronics unit 14 is constructed of lightweight, molded plastic, such as acrylonitrile-butadiene-styrene (ABS) or other suitable material. The shape and configuration of the body electronics 14 unit is not limited to any particular shape or configuration. As shown in FIG. 1, the body electronic unit 14 removably secures to the patient's arm via an armband 100, thus making the body electronics unit 14 readily accessibly to the patient. The armband 100 is capable of attaching to either the patient's right or left arm and attaches via Velcro or other suitable fastening means such as pins, snaps, or the like. Preferably, the body electronics unit 14 slides under a strap or pocket on the armband 100. Other means can be used to secure the body electronics unit to the patient without departing from the spirit and scope of the invention. For example, the body electronics unit 14 could be positioned in a pocket or pouch of patient gown, or a pendent or strap around a patient's neck. Alternatively, the body electronics unit 14 could also be secured to the bed or other bedside mounting kit. Referring to FIG. 7, the body electronic unit 14 has a user interface 102 and a battery 104. The user interface 102 provides information to the patient pertaining to the system's operating status or functionality. For example, an exemplary embodiment of the user interface 102 may provide information on whether the body electronics unit 14 is communicating or transmitting normally to the base station 16, whether the battery 104 of the body electronics unit 14 is charging or the battery 104 is low, whether the power of the body electronics unit 14 is activated, or whether the body electronics unit 14 or base station 16 is malfunctioning. In addition, the user interface 102 may provide instructions on the correct order or procedure for pairing or coupling the body electronics unit 14 with the base station 16. Such information may be communicated to the patient via the user interface 102 in various ways, for example, LEDs, LCD, text, audible tones, etc. An exemplary embodiment of the user interface is shown in FIG. 7A. The user interface 102 is readily accessible to the patient when the body electronics unit 14 is secured to the armband 100.

The battery 104 is inserted into a battery port 106 located in the bottom of the body electronics unit 14. The battery 104 is retained in the battery port 106 by latches or other suitable fastening means, such as clips, screws or the like. The battery 104 is preferably a 3.6 V Li-ion rechargeable battery. The battery is preferably constructed to have a charge indicator to indicate the amount of charge remaining in the battery. The battery 104 is readily accessible to the patient when the body electronics unit 14 is secured to the armband 100.

The body electronics unit 14 controls the acquisition of the ECG signals from the chest assembly 12 and the precordial assembly 60. A transmitter within the body electronics unit 14 receives or acquires ECG signals from the chest assembly 12 and the precordial assembly 60 preferably at 3 kbps. When the system is operating in "7 lead" mode (i.e., when only the chest assembly 12 is being used) the body electronics unit 14 acquires signals from the RL, RA, LL, LA, and V electrodes. When the system is operating in the "12 lead mode" (i.e., the chest assembly 12 and the precordial assembly 60 are being used) the body electronics unit 14 acquires signals from the RL, RA, LL, and LA electrodes via the chest assembly 12 and acquires signals from the VI thru V6 electrodes via the precordial assembly 60. In addition, other vital signs of the patient may be detected by the system and transmitted to the body electronics unit 14, for example pulse, respiration rate, heart rate, temperature, blood pressure, EEG signals and pulse oximeter signals.

The detection of the respiration rate may be achieved by obtaining a respiratory cycle or respirogram from an impedance pneumograph signal that is measured across two electrodes 20, for example the RA and LL electrodes. The respiratory impedance may be measured by applying a sinusoidal constant-current source between about 30 to 80 kHz across the electrodes 20, preferably 39 kHz. The resulting voltage amplitude across the electrodes at a given frequency is proportional to the transthoracic impedance (i.e., $Z=V/I$, where I is a constant amplitude). The electrodes that collect respiration rate data are also used to detect electrocardiograph signals. Thus, the current invention is capable of simultaneously measuring a patient's respiration rate and cardiac activity.

Figure 7B:
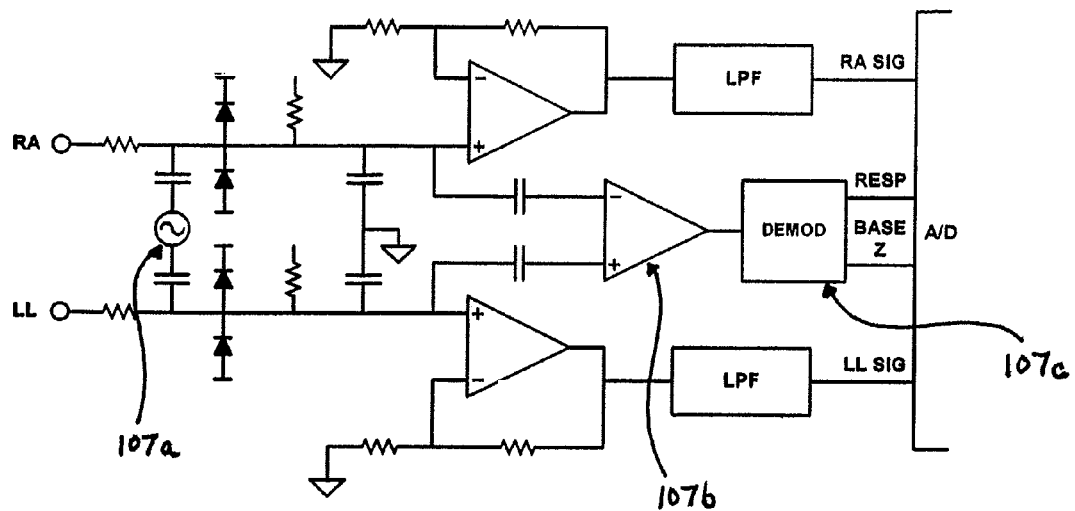
FIG. 7B is a block diagram of an exemplary of the respiration rate input circuit.
Figure 7C:
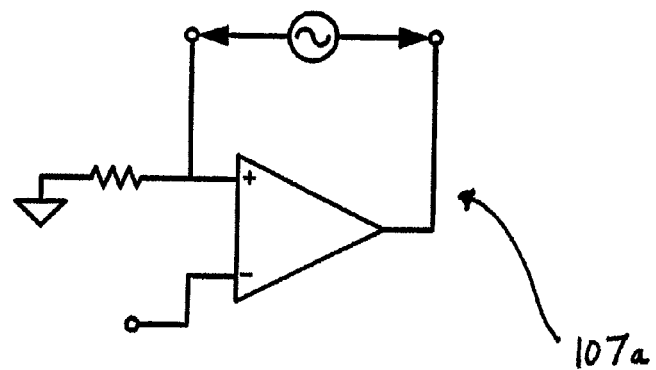
FIG. 7C is a block diagram of an exemplary embodiment of the current source circuit.

As shown in FIG. 7B, the body electronics unit 14 may include a current source 107A and a current source detection assembly that comprises a detection amplifier 107B, and a demodulator 107C to measure the respiratory impedance. In one embodiment, the current source 107 is capacitor-coupled to the RA and LL signals after the defibrillation resistors. The current source 107A outputs a sinusoidal signal, for example, a 68-μA sinusoidal signal, which passes through the RA electrode, through the patient, and back through the LL electrode. One of ordinary skill in the art will recognize that other electrodes, besides the RA and LL electrodes, may be used. An example circuit, using an operational amplifier to implement the current source 107A, is shown in FIG. 7c. By way of example, the maximum load impedance for the current source 107A is 13.1 Kohm, which is based on a maximum output voltage of 2.5 Vpp or 0.89 Vrms. When the maximum load impedance is 4 Kohm, the maximum value for the defibrillation resisters is 4.54 Kohm.

The detection amplifier 107B and the demodulator 107C process the current source signal. The detection amplifier 107B provides a high-impedance buffer and gain for the signal. The demodulator 107C converts the amplitude-modulated signal to a low-frequency base impedance (~1000 ohm) and an AC-coupled and amplified respiration impedance signal (~1 ohm pp). The respiratory impedance is split into a base impedance and a respiratory signal impedance to obtain more resolution for the respiratory signal impedance. By way of example, the base impedance signal may have a bandwidth of DC to 0.015 Hz while the respiration impedance signal has a bandwidth of 0.05 to 2.5 Hz. These signals may digitized at a sample rate of 10 Hz. The digitized impedance signals are then transmitted to the base station 16 for reconstruction.

Figure 8:
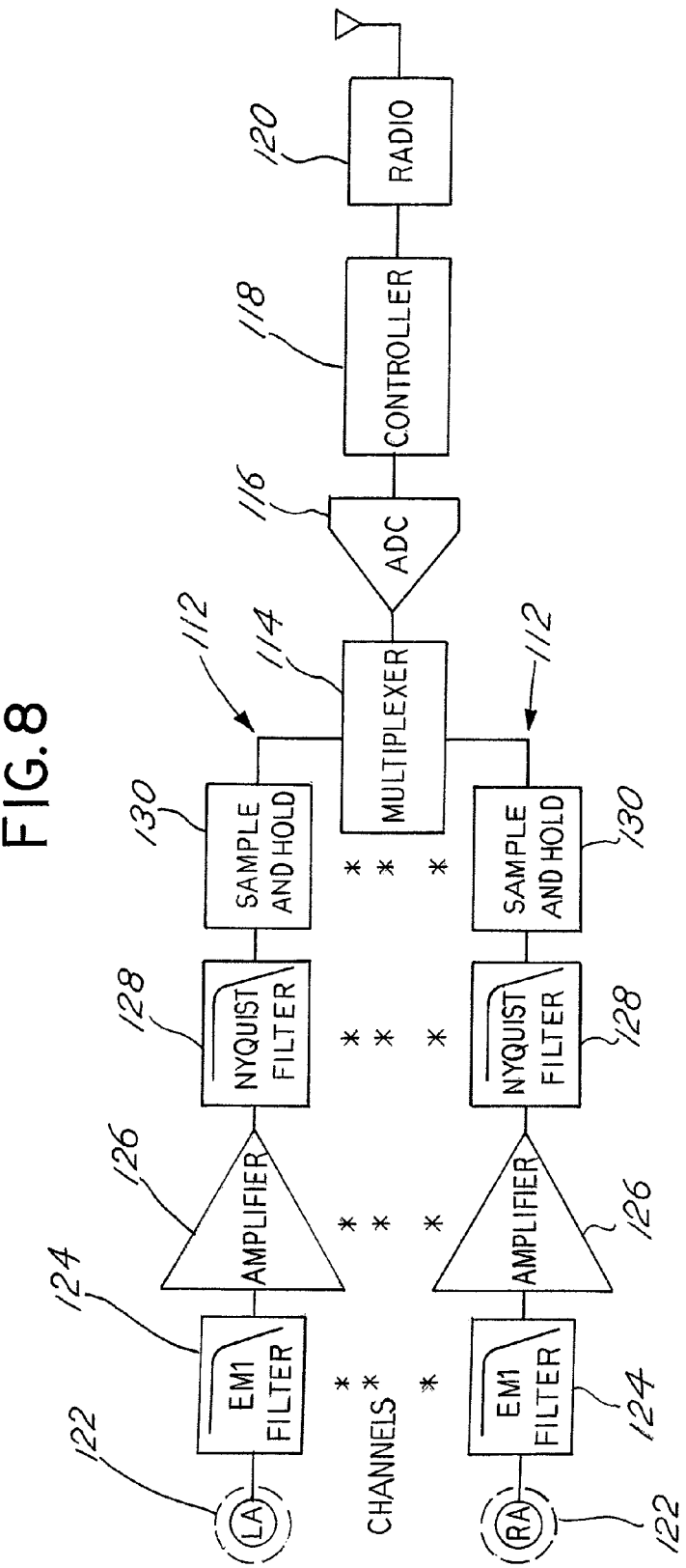
FIG. 8 is a block diagram of an exemplary embodiment of the transmitter.

As shown in FIG. 8, the transmitter may comprise an application specific integrated circuit, a processor or other circuit, a plurality of signal channels 112, a multiplexer 114, an analog-to-digital converter (ADC) 116, a controller 118, and a radio 120. Additionally, fewer or different components can be used. The body electronics unit 14 may have ten signal channels 112 corresponding to the eleven electrodes connected to the chest assembly 12 and the precordial assembly 60. The electrode channels 112 each comprise a connector 122, a filter 124, an amplifier 126, a Nyquist filter 128 and a sample and hold circuit 130. The connectors 122 of the signal channels 112 connect to either the chest assembly port 88 or the precordial assembly port 90, depending on whether the electrode channel 112 corresponds to an electrode located on the chest assembly 12 or the precordial assembly 60. The filter 124 comprises a low pass filter, such as for removing electromagnetic interference signals. The amplifier 126 amplifies the signals from the electrodes. The Nyquist filter 128 comprises a low pass filter for removing out-of-band high frequency content of the amplified signals to avoid sampling error. The sample and hold circuit 130 enables the system to sample all nine electrode channels signals 112 at the same or relatively same time so that there is no differential error created when these signals are combined later in the ECG monitor.

The multiplexer 114 sequentially selects signals from the electrode signal channels 112 using time division multiplexing. One of ordinary skill in the art, however, recognizes that other combination functions can be used. The ADC 116 converts the combined analog signals to digital signals for transmission. Preferably the controller 118 comprises a digital signal processor (DSP) that decimates the digitized signals as to lessen the bandwidth required to transmit the signals. The DSP also performs two-sample averaging and a thirty-tap Finite Impulse Response (FIR) digital low pass filter. The radio 120 modulates the digital signals with a carrier signal for transmission. In an exemplary embodiment, the radio 120 includes a demodulator for receiving information. The controller 118 digitally transmits the ECG data to the base station 16. In addition to transmitting ECG data, the controller 118 may transmit signals pertaining to physiological and non-physiological data such as token pairing information, pacemaker information, battery level information, electrode disconnection information, and other information as required. For example, vital signs such as pulse, respiration rate, heart rate, temperature, blood pressure, EEG signals, and pulse oximeter signals may be transmitted.

The body electronics unit 14 continuously monitors the integrity of all patient electrode connections. This function may be achieved by supplying a direct current between all of the electrodes and the RL electrode and measuring the DC impedance between all of the electrodes and the RL electrode. When any electrode becomes disconnected, a lead wire becomes broken, or the impedance between any individual electrode and the RL electrode becomes very high, the voltage on that particular electrode goes out of range. The body electronics unit 14 is capable of detecting the out of range voltage condition and sending a signal to the base station which in turn causes the base station to trigger the "lead off" alarm on the ECG monitor. Additionally, the body electronics unit 14 has a self-test function that monitors the integrity of the primary functions including the microprocessor, data acquisition, internal voltage references, and radio functionality. In the event a failure is detected, the body electronics unit will capture the fault condition, stop data acquisition and transmission and indicate that fault has occurred through the lead off alarm.

The body electronics unit 14 operates to minimize undesired noise or signals. For example, components are matched such that later application to a differential amplifier in a legacy ECG monitor for determining a heart vector is accurate. ECG vectors are not formed by the ECG system 10, but rather by the legacy ECG monitor. Because the ECG system 10 is essentially "in-series" with the legacy ECG monitor, any error may produce undesirable results. One potential source of error is differential error. This differential error can be observed on the legacy ECG monitor when the ECG monitor forms the ECG lead signals by combining the individual electrode signals in the ECG monitor input stage. This input stage comprises a difference, or differential, amplifier to eliminate common mode interference from the signals produced at the electrodes 20.

An artifact will be present if there is any difference in how each of the electrode signals are processed when the legacy ECG's differential amplifier forms the ECG lead signals or ECG vectors. For example, if there is a difference in the gain of the amplifier, a difference in the phase shift associated with the anti-aliasing (Nyquist) filters, or a difference in how the respective sample and hold circuits treat the electrode signals, then this differential error creates an artifact on the legacy ECG monitor. One important technique to minimize this potential source of differential errors is to choose a Nyquist filter cutoff frequency that is very high. This is because each individual filter will have differing group delay performance. To mitigate that difference, the frequency that this group delay will affect is much higher than the frequency of the ECG signals, which are about 0.05 Hz to 150 Hz. By choosing a high cutoff frequency for the Nyquist filters, any mismatch in the Nyquist filter components will not affect the accuracy of the individual electrode ECG signals. For example, picking a filter cutoff frequency of 1,200 Hz mitigates this source of error. With this approach, the individual electrode ECG signals are over sampled at about 3,000 Hz in order to not introduce aliasing. Of course higher filter cutoff frequencies and correspondingly higher sampling rates may further reduce error. Lower cutoff frequencies and/or sampling rate may be used.

Because the electrode signals are sampled at such a high rate, these signals may be decimated to minimize the required transmission bandwidth. For example the digital samples are preferably decimated by a factor of eight in the controller of the body electronics unit 14. Greater or lesser rates of decimation can be used, such as decimation as a function of the bandwidth available for transmission, the number of electrode signals to be represented, and the Nyquist sampling rate. The base station 16 receives the transmitted signals sent from the body electronics unit 14. The signals are transmitted as radio or other signals modulated with a carrier signal. Various air-interfaces can be used for transmission, such as BLUETOOTH or IEEE 802.11b.

Figure 9A:
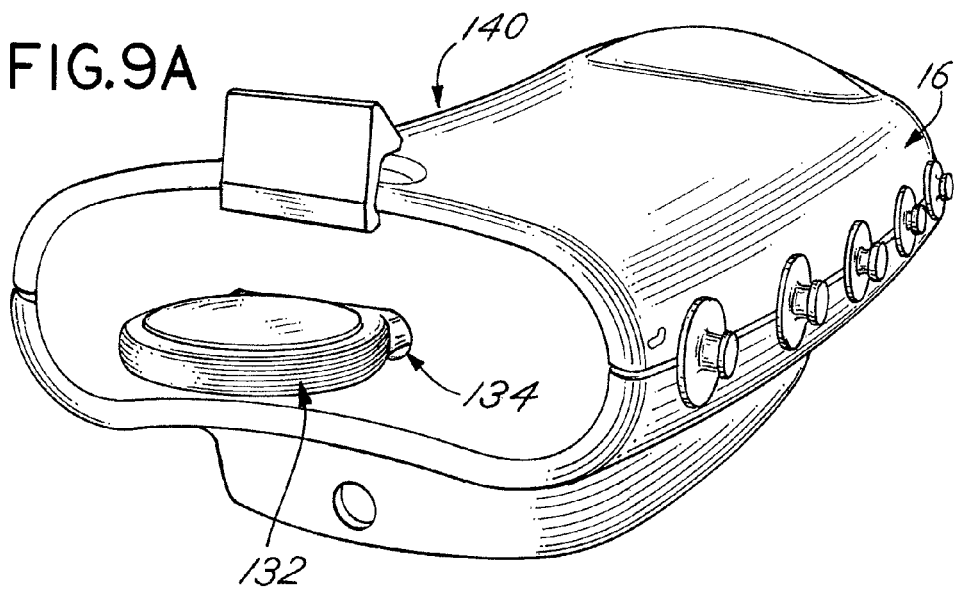
FIG. 9A is a perspective view of an exemplary embodiment of the base station used in conjunction with the token key.
Figure 9B:
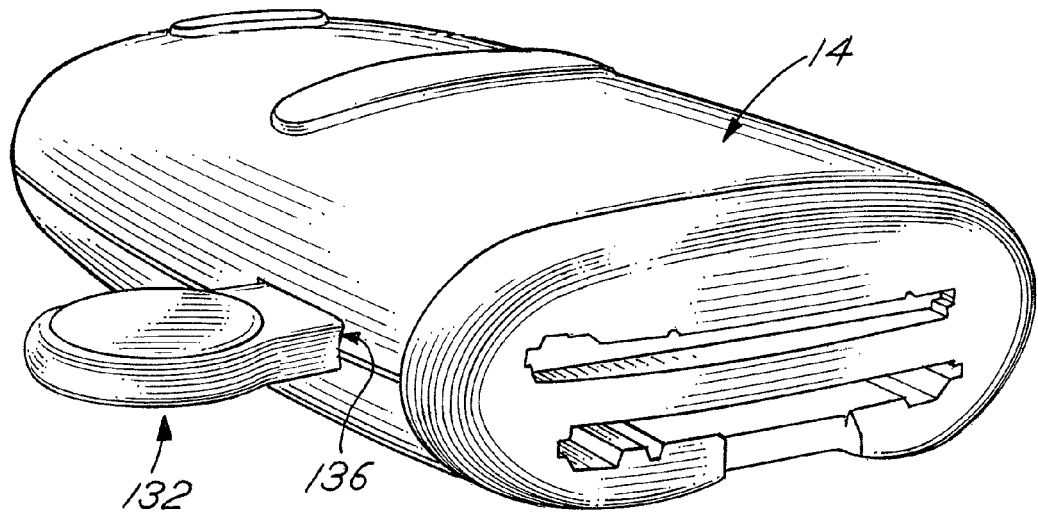
FIG. 9B depicts the body electronics unit used in conjunction with the token key.

To establish proper communication between the body electronics unit 14 and the base station 16, the base station 16 and body electronics unit 14 need to be paired such that the base station 16 and the body electronics unit 14 only recognize signals from its pair. This may be accomplished in number of ways, for example, infra-red pairing or direction connection pairing. Preferably, a token key 132 is used to pair or radio frequency link the body electronics unit 14 and the base station 16. Referring to FIGS. 9A and 9B, the token key 132 has memory chip and may optionally have a plurality of tongues or pins that fit within grooves located in a token key port 134 of the base station 16 and within grooves of a token key port 136 of the body electronics unit 14. To pair the body electronics unit 14 with the base station 16, the token key 132 is inserted into the token key port 134 of the base station and reads and records an identification number for the base station 16. The token key 132 is then removed from the token key port 134 and inserted into the token key port 136 located in the body electronics unit 14. The electronics unit 14 receives the identification number for the base station 16 from the token key 132. In turn, the token key 132 reads and records the identification number for the body electronics unit 14. The token key 132 is then removed from the body electronics unit 14 and reinserted into the token key port 134 of the base station 16 whereby the base station 16 confirms the presence of its own identification number on the token key 132 and also reads the identification number for the body electronics unit 14 from the token key 132. The body electronics unit 14 and the base station 16 are paired. Alternatively, pairing or coupling can be accomplished by first inserting the token key 132 into the body electronics unit 14, removing the token key 132 and inserting the token key 132 into the base station 16, removing the token key 132 and reinserting the token 132 into the body electronics unit 14. In other words, the order in which the token key 132 is inserted into the body electronics unit 14 and the base station 16 is not critical to the proper operation of the system. The user interface 102 may provide the user or health care provider with instructions on the correct order for pairing the body electronics unit 14 with the base station 16. The use of the token key 132 allows the pairing function to occur while the body electronics unit 14 is worn by the patient. This feature eliminates the need to disconnect and reconnect the body electronics unit 14 when a patient needs to be connected to different ECG monitors as a result of being moved around a hospital. The patient's body electronics unit 14 is just repaired with a new base station using the token key 132.

After the body electronics unit 14 and the base station 16 are paired, the body electronics unit 14 and the base station 16 will remain communicating with each other as long as the token key 132 remains in the token key port 134 of the base station 16 (or the token key port 136 of the body electronics unit 14, depending on the order of the pairing process). In other words, as soon as the token key 132 is removed from the base station 16, the electronics unit 14 and the base station 16 will discontinue or cease communication. Any specific token key 132 can be used to pair any specific base station 16 with any specific body electronics unit 14.

The ECG system can be configured such that the body electronics unit 14 simultaneously communicates with more than one base station 16. In one exemplary embodiment, a body electronics unit 14 can be configured to collect and transmit diagnostic "7-lead" ECG signals to a first base station 16 and collect and transmit diagnostic "12-lead" ECG signals to a second base station 16. More preferably, each body electronics unit 14 may be configured with a temporary transmission mode that allows the body electronics unit 14, which is already paired with and transmitting to a first base station 16, to temporarily pair with and temporarily transmit ECG data to a second base station 16. Such a configuration will allow the health care provider to take a collect a temporary 12-lead ECG signal measurement from a patient who is already on continuous 7-lead ECG signal monitoring. To take the temporary 12-lead measurement, the health care provider will be required to attach the precordial assembly 60 (the chest assembly 12 will already be attached for 7-lead monitoring) to the body electronics unit 14 and the patient. A temporary 12-lead mode switch on the body electronics unit 14 will be activated before the health care provider pairs the body electronics unit 14 with the second base station. The body electronics unit 14 and the second base station 16 will be paired in accordance with the pairing method discussed above. Once the pairing is completed, the body electronics unit 14 will begin to transmit 12-lead ECG data with the second base station 16 while simultaneously transmitting 7-lead ECG data to the first base station 16. The body electronics unit 14 can be configured to simultaneously transmit in the temporary mode for a sufficient, predetermined period of time to collect the 12-lead diagnostic ECG reading. Preferably, the body electronics unit 14 will be configured to transmit in the temporary mode for at least two minutes. After the predetermined time period for temporary transmission has ended, the body electronics unit 14 will stop transmitting to the second base station 16.

Figure 10:
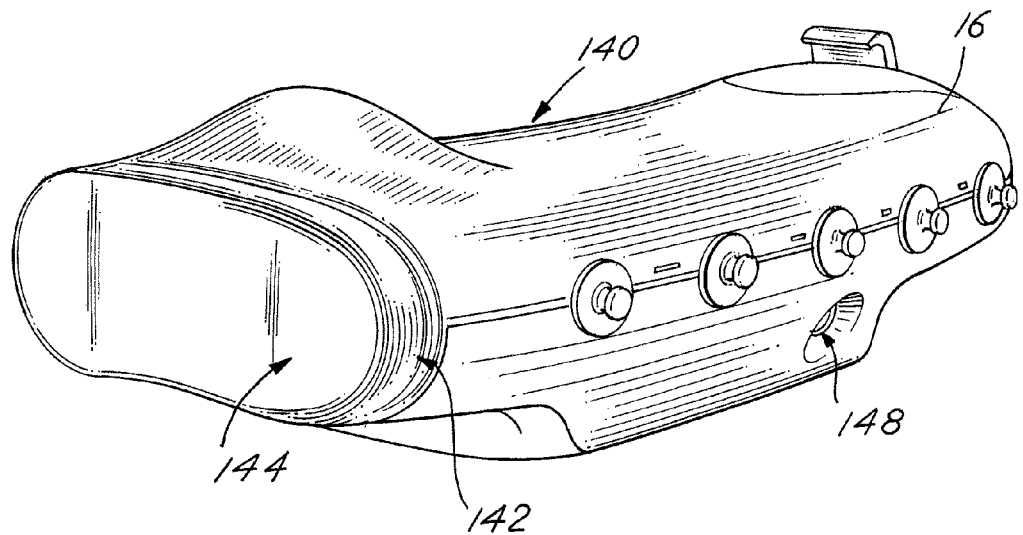
FIG. 10 is a perspective view of an exemplary embodiment of the base station.

The outside casing of the base station 16 is constructed of lightweight, molded plastic, such as acrylonitrile-butadiene-styrene CABS) or other suitable material. The shape and configuration of the base station 16 is not limited to any particular shape or configuration. The base station 16 is a portable transceiver that can be placed in any location and does not necessarily have to be placed or secured in any fixed location. Referring to FIG. 1, the base station 16 is preferably removably secured to an ECG monitor 138 via suitable mounting means, such as Velcro®, dual-lock strips, double-sided foam tape, or the like. Preferably, the base station 16 is removably mounted to a mounting plate secured near the ECG monitor 138 via suitable mounting means. Alternatively, the base station 16 can be incorporated into the monitor 138. As shown in FIG. 10, the base station 16 has a cradle 140 for storing the body electronics unit 14 when the body electronics unit 14 is not in use or otherwise off the patient. In addition, the base station 16 has a battery port 142 in which a base station battery 144 is removably inserted. The base station 16 may be constructed to have a plurality of battery ports that store and charge batteries when the batteries are not being used. When the base station 16 is not plugged into an AC wall power inlet, the base station battery 144 provides power to the base station 16. When the base station 16 is operating on AC wall power, the base station 16 charges the base station battery 144 when the base station battery 144 is in the battery port 142. The base station 16 has a power switch that activates/deactivates the power to the base station 16 and a power cord connection 148 for connecting a power cord to an AC wall power inlet. The base station battery 144 is preferably a 3.6 V Li-ion rechargeable battery. Accordingly, the base station battery 144 and the body electronics unit battery 104 are preferably identical and interchangeable, such that each battery can be used in either the body electronics unit 14 or the base station 16. The system is designed such that a discharged body electronics unit battery 104 is swapped for a charged base station battery 144. In this manner a charged battery is always readily available for the body electronics unit. In addition, the base station 16 has a lead switch that allows the health care provider to instruct the base station 16 to operate in "7 lead" mode or "12 lead" mode.

Figure 11:
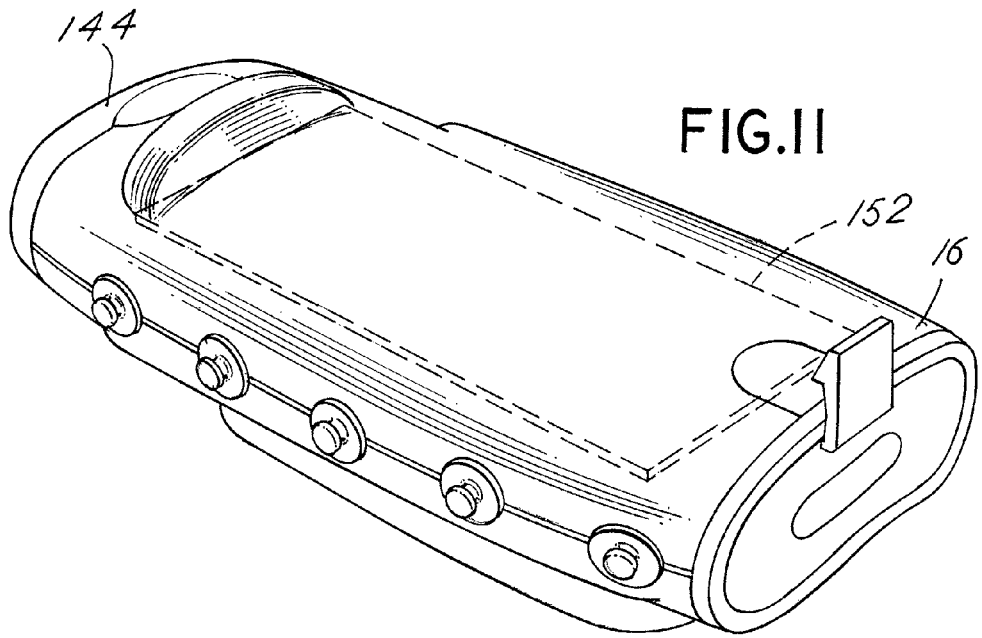
FIG. 11 is a perspective view of an exemplary embodiment of the base station.

As depicted in FIG. 11, the base station 16 has a user interface 152 that provides information to the health provider or patient pertaining to the system's operating status or functionality. For example, the user interface 152 may provide information on whether the body electronics unit 14 is communicating or transmitting normally to the base station 16, whether the base station battery 144 is charging or the battery 144 is low, whether the body electronics unit battery 104 is low, or whether the power of the base station 16 is activated, whether the base station 16 is malfunctioning or otherwise requires servicing. In addition the user interface 102 may provide instructions on the correct order or procedure for pairing or coupling the body electronics unit 14 with the base station 16. Such information may be communicated to the health care provider or patient via the user interface 152 in various ways, for example, LED's, LCD, text, audible tones, etc. An exemplary embodiment of the user interface 102 is shown in FIG. 11A.

Additionally, the base station has a self-test function that monitors the integrity of the primary functions including the microprocessor, data acquisition, internal voltage references, and radio functionality. In the event a failure is detected, the body electronics unit will capture the fault condition, stop data acquisition and transmission and indicate that fault has occurred through the lead off alarm.

A receiver located within the base station 16 receives signals sent to the base station 16 from the body electronics unit 14. As shown in FIG. 12, the receiver includes a radio 156, a controller 158, a digital-to-analog converter (DAC) 160, a de-multiplexer 162, and a plurality of electrode signal channels 166. Additionally, fewer or different components can be used. The radio 156 demodulates the received signals for identifying digital data representing the combined electrode signals. In an exemplary embodiment, the radio 156 includes a modulator for transmitting control information. The controller 158 controls operation of the various components and may further process the signals from the radio 156, such as interpolating data, converting the signals to digital information, generating control signals for the transmitter in the electronics unit 14, operating any user output or input devices, and diagnosing operation of the ECG system. Preferably, the controller 118 interpolates the electrode signals to return the effective sample rate to about 3 kHz or another frequency. This enables the reconstruction filters to have a cutoff frequency many times the bandwidth of the electrode signals, thus minimizing any differences in group delay at the frequencies of interest, i.e., less than 150 Hz. The DAC 160 converts the digital signals to analog signals. The demultiplexer 162 separates the individual regenerated electrode signals onto the separate electrode signal channels 166. The receiver may have a transceiver that operates pursuant to the BLUETOOTH air interface specification for two-way communication with the transmitter in the body electronics unit 14.

The receiver may have nine electrode signal channels 166 corresponding to the ten electrodes. For continuous monitoring with only the chest assembly 12, the V electrode signal is output to the "V/$V_1$" terminal on the receiver. For 12-lead ECG with both the chest assembly 12 and precordial assembly 60, the V electrode signal is discarded and the $V_1$ electrode signal is output to the "V/$V_1$" terminal on the receiver. The electrode signal channels 166 each comprise a sample and hold circuit 168, a filter 170, and an attenuator 172. The sample and hold circuit 168 is controlled by the controller 118 so that the converted electrode signals appear simultaneously on each electrode signal channel 166. Other embodiments may include individual DAC's that provide the signal substantially simultaneously. The filter 170 comprises a low pass reconstruction filter for removing high frequency signals associated with the DAC conversion process. The attenuator 172 comprises an amplifier for decreasing the amplitude to a level associated with signals at the electrodes, which were earlier amplified in the amplifiers of the body electronics unit 14. This results in a unity system gain so as not to introduce error between the electrodes and the conventional ECG monitor.

Figure 12A:
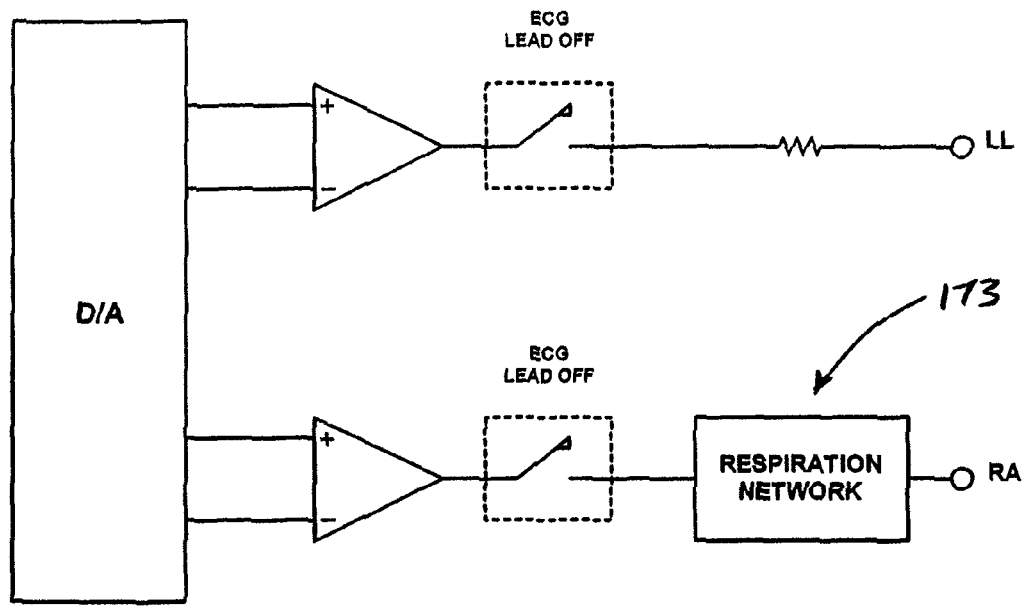
FIG. 12A is a block diagram of an exemplary embodiment of the respiration rate input circuit.
Figure 12B:
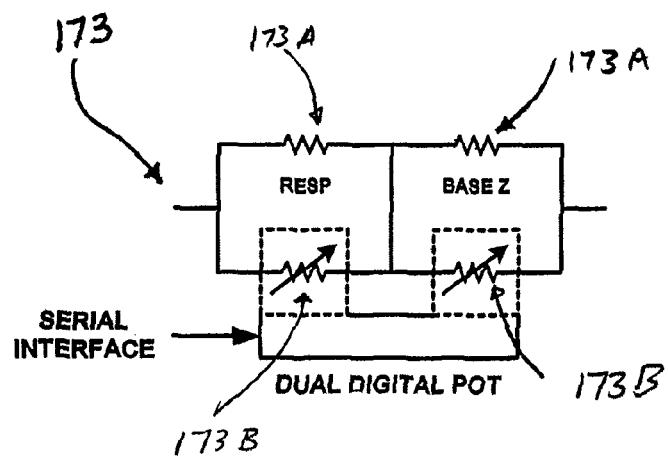
FIG. 12B is a block diagram of an exemplary embodiment of the respiration rate network.

Referring to FIG. 12A, the base station 16 may include a respiration network 173 inserted in series with the electrode signal channel 166, that corresponds to the RA electrode, to reconstruct the digitized impedance signals sent from the electronics body unit 14. As depicted in FIG. 12B, the respiration network 173 may include digitally controlled resistors 173A and dual digital potentiometers 173B, one used for the base impedance signal and one for the respiratory signal, in series with the digitally controlled resistors. The base station 16 may further include a log taper potentiometer (not shown) to reduce the linearity caused by using the digitally controlled resistors with the dual digital potentiometers.

Figure 13:
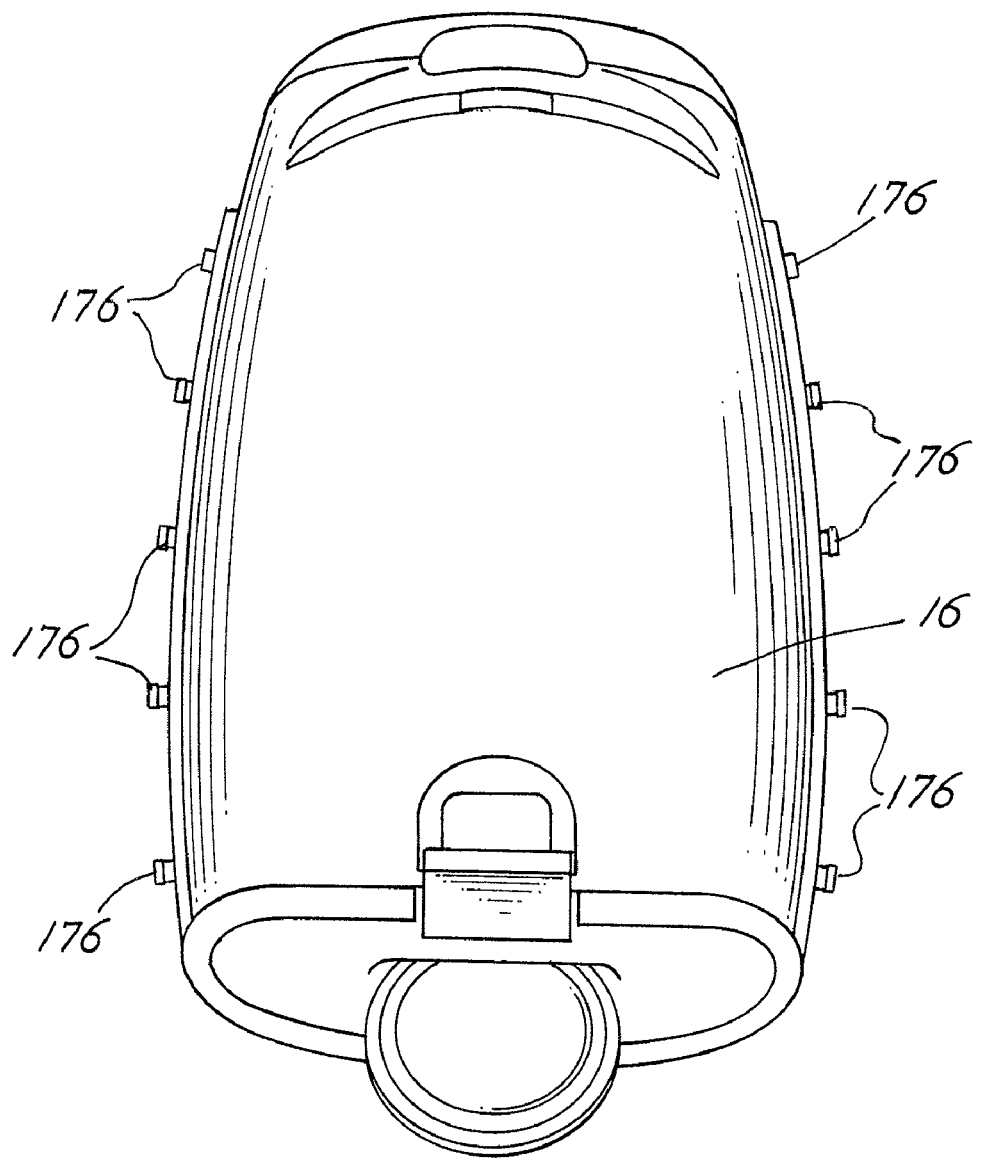
FIG. 13 is a perspective view of an exemplary embodiment of the base station.

Referring to FIG. 1, the base station 16 transmits the ECG signals and other physiological and non-physiological data to the ECG monitor 138 via pre-existing or conventional monitor cables 174. In turn, the information is displayed on the ECG monitor and reviewed by a physician. As depicted in FIG. 13, the monitor cables removably insert onto snap terminals 176 located on the base station 16. Preferably, the base station 16 has ten snap terminals 176 arranged on the left and right side of the base station 16. The snap terminals 176 and the monitor cables are preferably labeled and color-coded so that the monitor cables are properly connected to the base station 16. For instance, the five snap terminals 176 located on the left side of the base station 16 and the monitor cable may be labeled as RL, LA, LL, RA, and V/V1. In addition, the five snap terminals 176 on the right side of the base station 16 and the monitor cable may be labeled V2, V3, V4, V5, and V6. When the ECG system is operating in "7 lead" mode (i.e., only the chest assembly 12 is used) the monitor cable is plugged into the five snap terminals 176 on the left side of the base station 16. When the ECG system is operating in "12 lead" mode (i.e., both the chest assembly 12 and the precordial assembly 60 is used) both the monitor cables are plugged into the snap terminals 176—the-top four snap terminals 176 on the left side of the base station 16 will be used for chest assembly electrodes and the remaining six snap terminals 176 will be used for precordial assembly electrodes.

The ECG system of the present invention may be configured to monitor and transmit pacemaker pulse information from the body electronics unit 14 to the base station 16. As described above, the body electronics unit 14 may have a plurality of signal channels 112 that are sampled to collect physiological data from the patient. Preferably, there are ten channels. Three of the channels correspond to the LA, RA, and LL electrodes and are sampled at 16 kHz. The seven remaining channels correspond to the V and $V_1$-$V_6$ electrodes and are sampled at 4 kHz. The channels corresponding to the LA, RA, and LL electrodes are sampled at a faster rate in order. to detect fast transients (i.e., pacemaker pulses) in the data from these channels.

Figure 18:
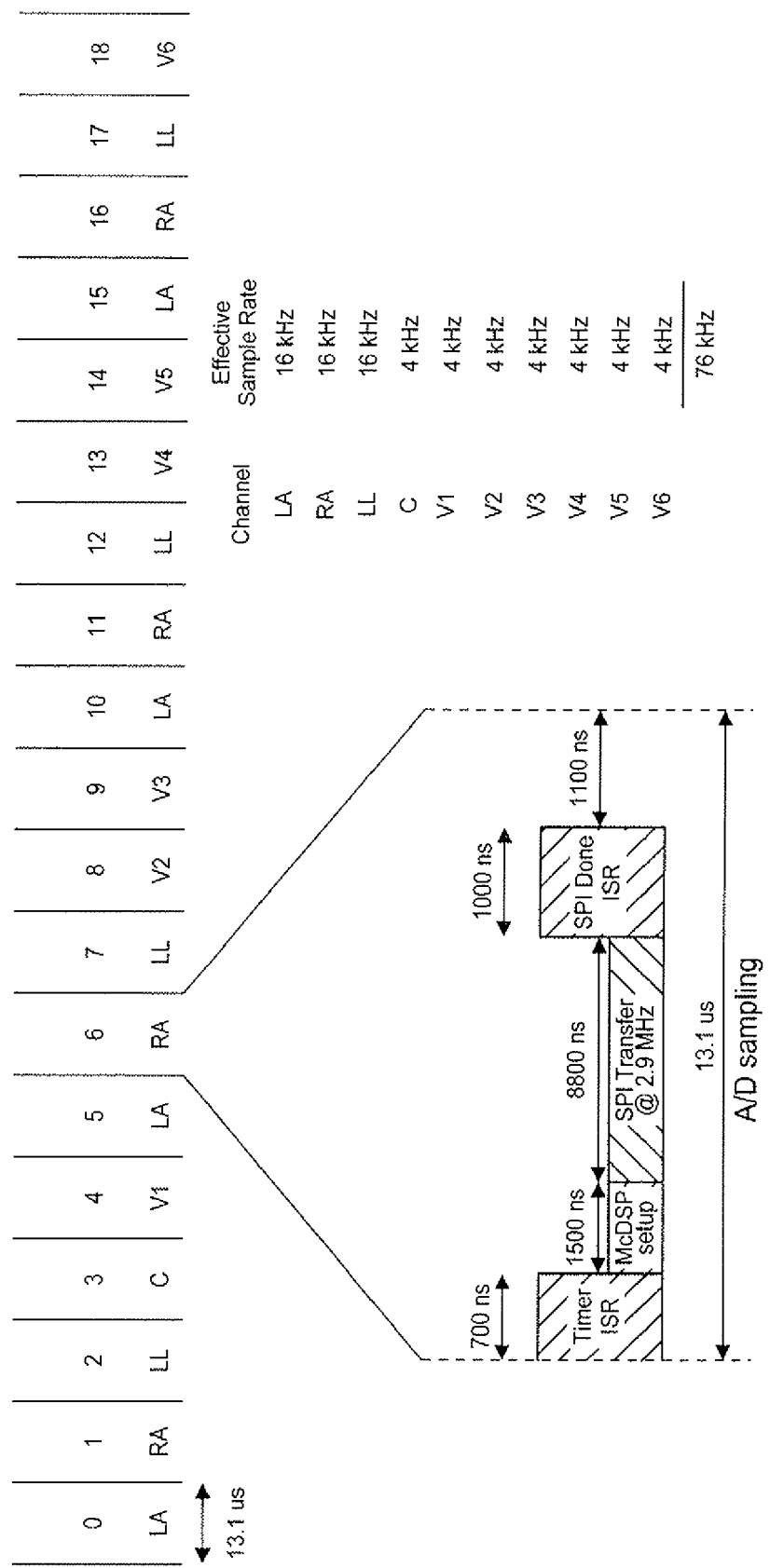
FIG. 18 depicts the order and timing in which the body electronics unit samples the signal channels.

Sampling of the plurality of signal channels 112 may be performed by a serial ADC. The ADC can be 16-bit converter. A bank or series of multiplexers select the channels for sampling. To sample the three channels corresponding to the LA, RA, and LL electrodes at 16 kHz and the remaining seven channels at 4 kHz, nineteen "virtual channels" are created. The virtual channels allow the system to perform nineteen samplings at 4 kHz, rather than three samplings at 16 kHz and seven samplings at 4 kHz. These virtual channels are four copies of each of the three channels corresponding to the LA, RA and LL electrodes and one copy of all the remaining channels corresponding to the V and $V_1$-$V_6$ electrodes. The virtual channels are $LA_i$, $LA_{ii}$, $LA_{iii}$, $LA_{iv}$, $RA_i$, $RA_{ii}$, $RA_{iii}$, $RA_{iv}$, $LL_i$, $LL_{ii}$, $LL_{iii}$, $LL_{iv}$, V, and $V_1$-$V_6$. The order of and timing of the sampling of the signal channels is depicted in FIG. 18.

Figure 19:
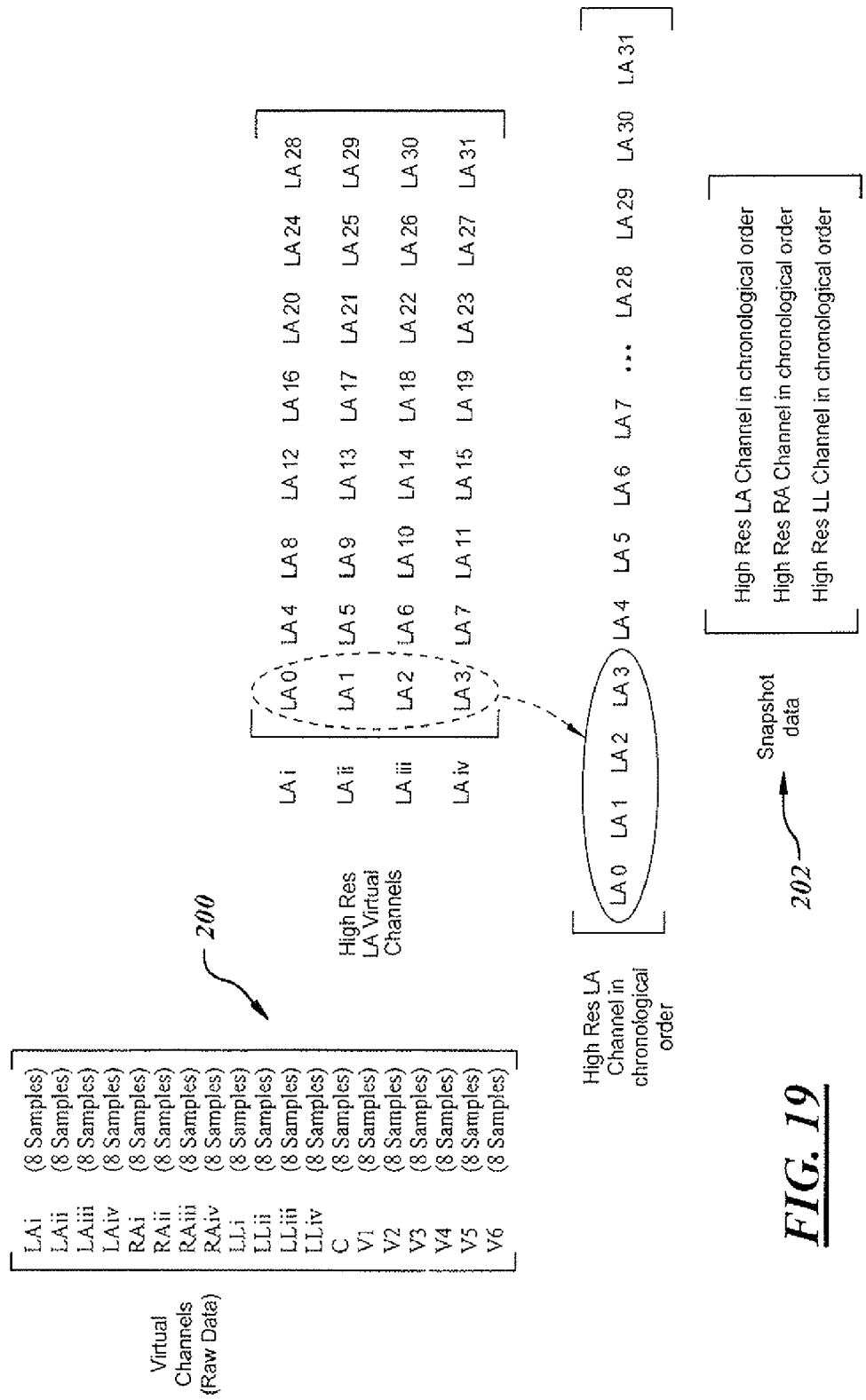
FIG. 19 depicts the formation of the raw data set and the snapshot data set after sampling the signal channels.

Referring to FIG. 19, after sampling the nineteen virtual channels eight times each, a first data set 200 is formed. The first data set 200 is referred to as the raw data set. The data from the channels corresponding to the LA, RA, LL electrodes is copied and reorganized into a second data set 202. The second data 202 set is referred to as the snapshot data set. The snapshot data set is processed to identify spikes in each lead (i.e., Lead 1=LA−RA, Lead 2=LL−RA, Lead 3=LL−LA) that may be indicative of pacemaker pulses. To detect a pacemaker pulse, the differences between samples n and n−2 is calculated for each lead. If the differences between samples n and n−2 exceed a predetermined threshold value, the previous, current, and next snapshot data set are packaged and transmitted to the base station 16. The three snapshot data sets total 6 ms of high-resolution data.

Before the raw data set can be transmitted to the base station 16, the raw data is averaged and filtered. Averaging and filtering reduces the gaussian-distributed noise inherent in the A/D conversion. In addition, averaging the raw data set provides a uniform sampling rate for all channels before the data enters a series of Finite Impulse Response (FIR) filters. The channels corresponding to the LA, RA, LL electrodes undergo an 8-to-1 averaging and the channels corresponding to the V and $V_1$-$V_6$ electrodes undergo a 2-to-1 averaging to form raw data packets.

Figure 20:
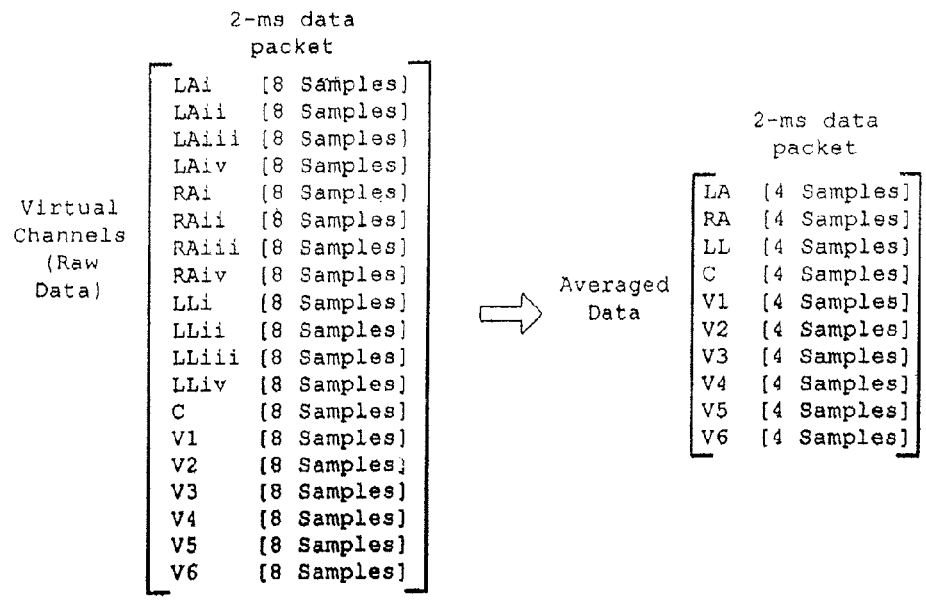
FIG. 20 depicts the averaging process for the raw data set before transmission of the data set to the base station.

The raw data set that enters the averaging and filtering process represent 2 ms worth of data packets for all of the channels. The data packets contain thirty-two samples of the channels corresponding to the LA, RA, LL electrodes and eight samples of the channels corresponding to the V and $V_1$-$V_6$ electrodes. As depicted in FIG. 20, the averaging process converts the data packets into four samples of the ten channels for an effective data rate of 2 kHz.

Figure 21:
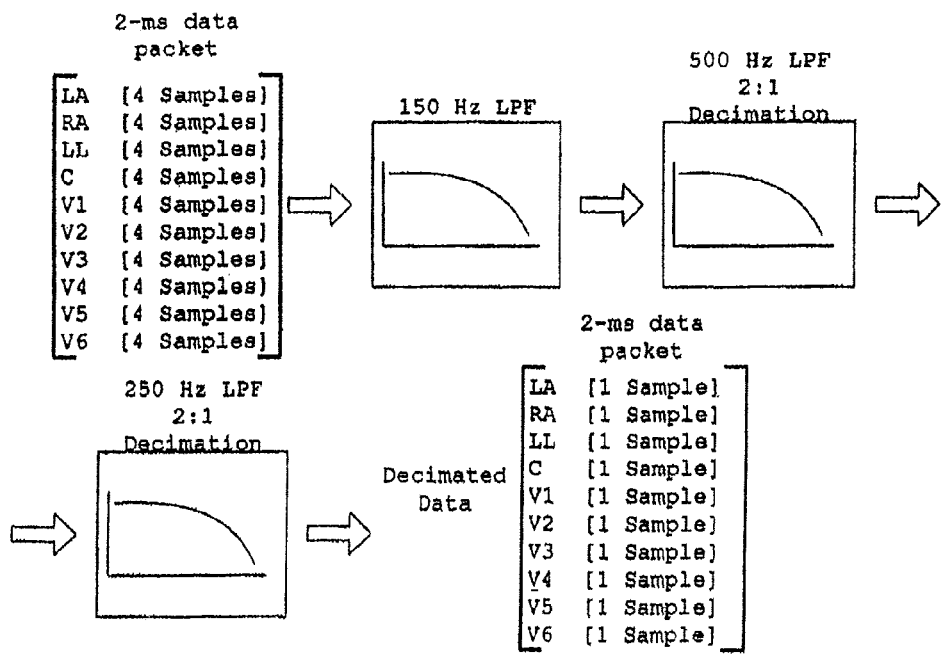
FIG. 21 depicts the filtering process for the raw data set conducted after the averaging process and before transmission of the data set to the base station.

After the data set is averaged, a unity-gain, 150-Hz low-pass filter is applied to the data set. The low-pass-filtered data set then runs through two stages of FIR half band filtering and decimation. The 2 kHz of data is converted to 500 Hz. Four samples of each channel are decimated to two samples (2 kHz to 1 kHz) and then decimated from two samples to one sample (1 kHz to 500 Hz). The 500 Hz data has a maximum unaliased frequency of 250 Hz and has been low passed filtered by 150 Hz to eliminate any possibility of aliasing. FIG. 21 depicts the filtering process.

Figure 23:
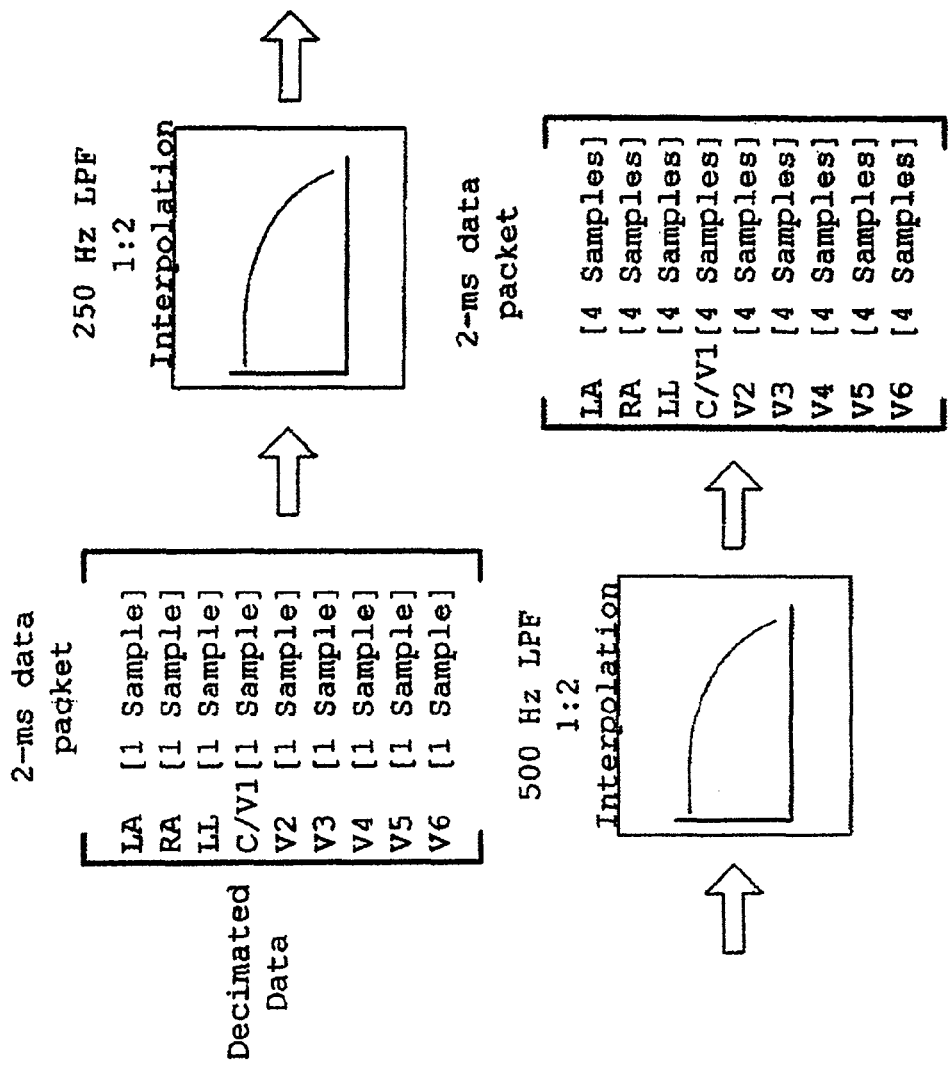
FIG. 23 depicts the FIR interpolation process for the ECG data packets.
Figure 24:
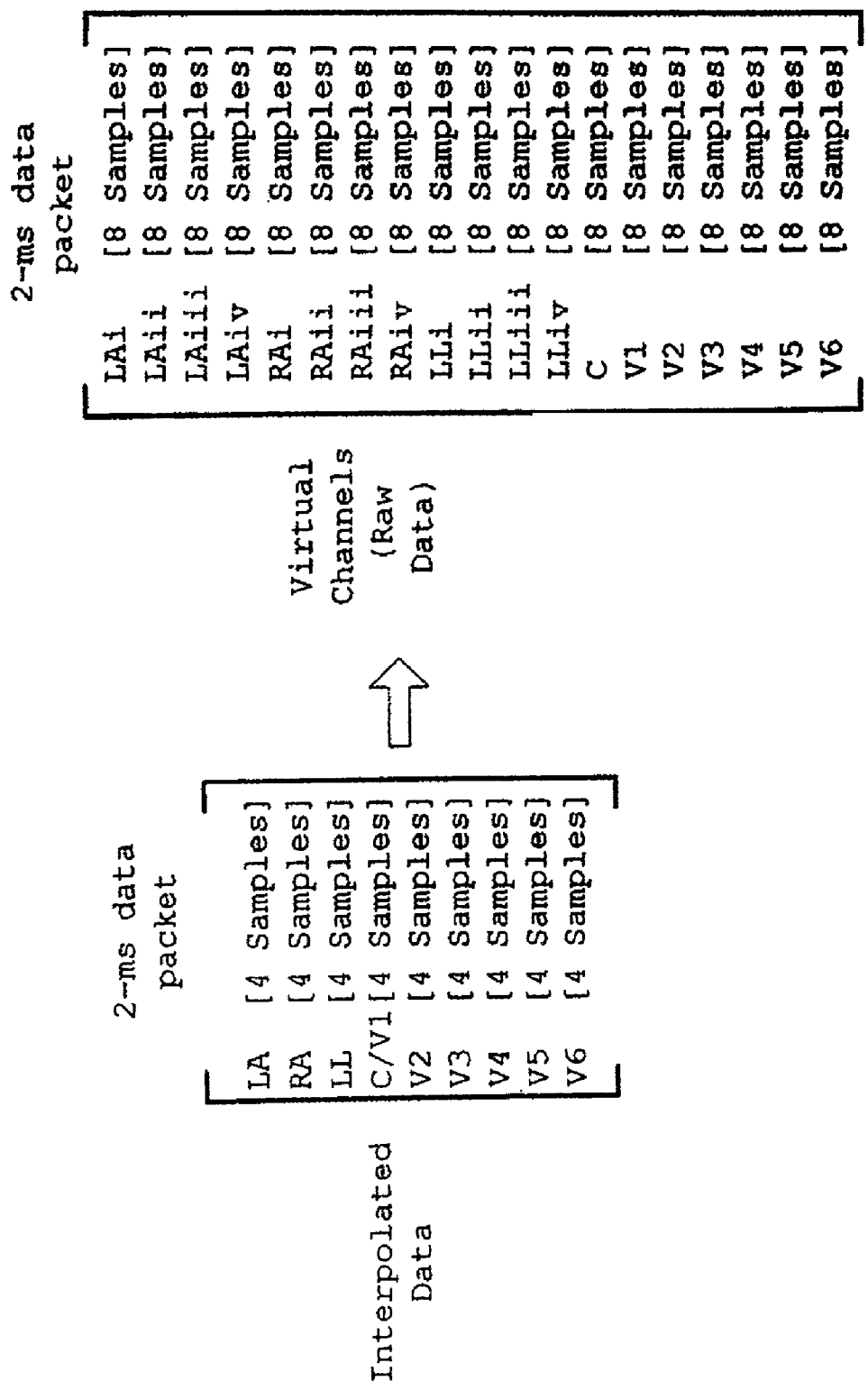
FIG. 24 depicts the duplication process conducted after the FIR interpolation process.

After decimation, the raw data set is ready for packaging and transmission via the BLUETOOTH air interface specification. Each data point represents 2 ms of data (500 Hz sampling). The maximum frequency that this data can represent is 250 Hz and the data has been filtered to reject frequencies above 150 Hz. The raw data set and the snapshot data set are packaged for transmission to the base station 16 via BLUETOOTH air interface transmission as depicted in FIG. 22. The raw data set and the snapshot data set are packaged into raw data set packets and snapshot data set packets. Each data packet has a packet ID so that the raw data set and the snapshot data set can be properly paired at the base The raw data packet transmitted from the body electronics unit 14 is interpolated and duplicated at the base station 16. Two FIR interpolated filters convert one sample of raw data into four samples. FIG. 23 depicts the FIR interpolation process. The data for each of the channels corresponding to the LA, RA, LL electrodes are duplicated eight times to create thirty-two samples (2 ms of data at 16 kHz playback rate). Data for each of the channels corresponding to the V and $V_1$-$V_6$ electrodes are duplicated two times to create eight samples (2 ms of data at 4 kHz playback rate). With regard to the data corresponding to the V/$V_1$ channel, the base station 16 receives one channel of data that represents either the data from the V electrode or data from the $V_1$ electrode. The base station 16 has a single port allocated to this data, regardless of whether the data is from the V electrode or the $V_1$ electrode. To preserve the same sequence and timing on D/A playback, two virtual channels are created from the single channel corresponding to the V/$V_1$ electrodes. The data for the V/$V_1$ channel is copied to create a V channel and $V_1$ channel. FIG. 24 depicts the duplication of the interpolated data.

Figure 25:
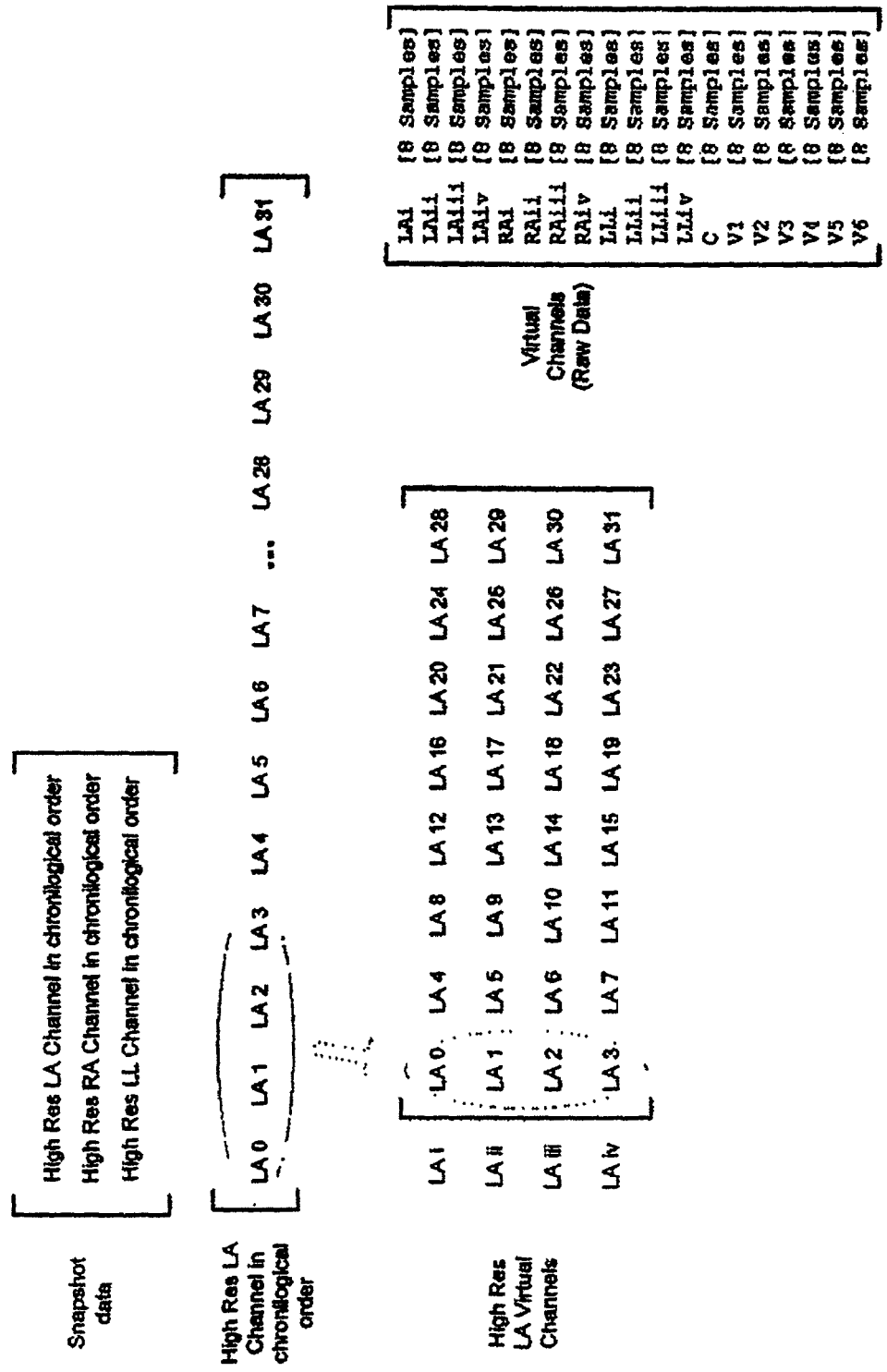
FIG. 25 depicts the restoration of the pacemaker pulse in the ECG data stream.

The snapshot data set can be placed into the interpolated raw data to form a reconstructed, high-resolution waveform. After the raw data packet is interpolated and duplicated, the ID of that raw data packet is compared with the next available snapshot data packet. If the ID from the raw data packet matches the ID from the snapshot data packet, the raw data corresponding to the LA, RA, LL electrodes is overwritten with the data contained within the snapshot data set. If the ID from the raw data packet matches the ID from the snapshot data packet does not match, the snapshot data packet is considered out of sync and rejected or erased. FIG. 25 depicts the restoration of the pacemaker pulse.

Figure 26:
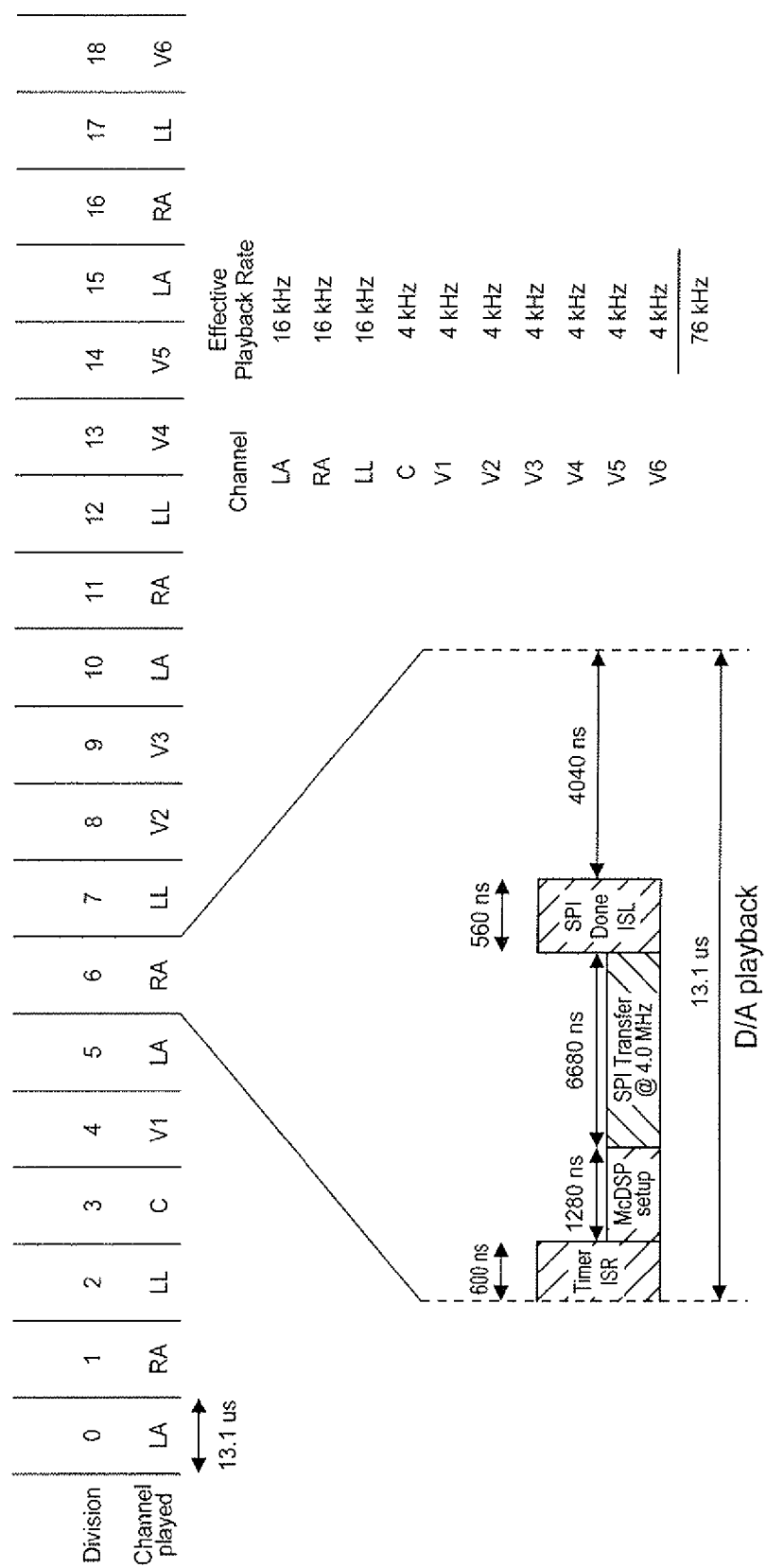
FIG. 26 depicts the order and timing in which the base station plays out the signal channels.

The channels corresponding to the LA, RA, and LL electrodes are played out on the DAC at 16 kHz and the remaining channels corresponding to the V and $V_1$-$V_6$ electrodes are played out on the DAC at 4 kHz. The playback occurs in the same way that the sampling occurred at the body electronics unit 14. FIG. 26 depicts the sequence and timing in which the nineteen virtual channels are played out.

There may be instances where a base station 16 will not be in every ward or hospital room for use with the body electronics unit 14. In such instances, an adapter assembly 178 may be used to connect the chest assembly 12 or the precordial assembly 60 to the ECG monitor 138. In one exemplary embodiment, the adaptor assembly 178 allows the chest assembly 12 or precordial assembly 60 to be plugged directly into a conventional or existing telemetry transmitter. FIG. 14 depicts the adapter assembly 178 having an assembly receptacle 180 that connects to the chest assembly 12 (not shown) or the precordial assembly 60 (not shown) and a telemetry box receptacle 182 that connects to a conventional or existing telemetry transmitter. In another exemplary embodiment, the adaptor assembly 178 allows the chest assembly 12 or precordial assembly 60 to be plugged directly into a conventional or existing ECG monitor trunk cables. FIG. 15 depicts the adaptor assembly 178 having an assembly receptacle 184 for connecting to the chest assembly 12 (not shown) or the precordial assembly 60 (not shown) and a cable assembly 185 for connecting to a conventional or existing ECG monitor trunk cable. The cable assembly 185 has a cable 186 that connects to a trunk cable adaptor 188 for connecting to an ECG monitor trunk cable. In another exemplary embodiment, the adaptor assembly 178 allows the chest assembly 12 or precordial assembly 60 to be plugged directly into standard lead wires that connect to an ECG monitor. Various configurations of the adapter 178 are possible depending on the connector configuration of the standard lead wires.

FIG. 17 depicts the method of monitoring the cardiac activity in the patient's heart using the wireless ECG system of the presentation invention. In step 198, electrodes placed on the patient's body. In step 200, the chest assembly 12 and/or precordial assembly 60 are positioned on the patient's body by connecting the electrode connectors 21, 62 to the electrodes. In step 202, the chest assembly 12 and/or the precordial assembly 60 are plugged into the body electronics unit 14. In step 204, the electronics unit 14 and the base station 16 are paired or coupled by inserting the token key 132 into the base station 16, removing the token key 132 from the base station 16, inserting the token key 132 into the body electronics unit 14, removing the token key 132 from the electronics unit 14, and reinserting the token key 132 into the base station 16. Alternatively, coupling can be accomplished by inserting the token key 132 into the body electronics unit 14, removing the token key 132 from the body electronics unit, inserting the token key 132 into the base station 16, removing the token key 132 from the base station 16 and reinserting the token key 132 into the body electronics unit 14. In step 206, electrical signals from the patient's heart are detected and transmitted to the body electronics unit 14 via chest assembly 12 and the precordial assembly 60. In step 208, the electrical signals from the heart are transformed by the body electronics unit 14 from analog signals to digital signals. In step 210, the body electronics unit 14 transmits the digital signals to the base station 16 via radio transmission. In step 212, the base station 16 transforms the digital signals into analog signals. In step 214, the base station 16 transmits the analog signals to the ECG monitor 138 via monitor cables 174. In step 216, the ECG monitor 138 processes the analog signals into meaningful information that can be displayed on the monitor 138.

Figure 27:
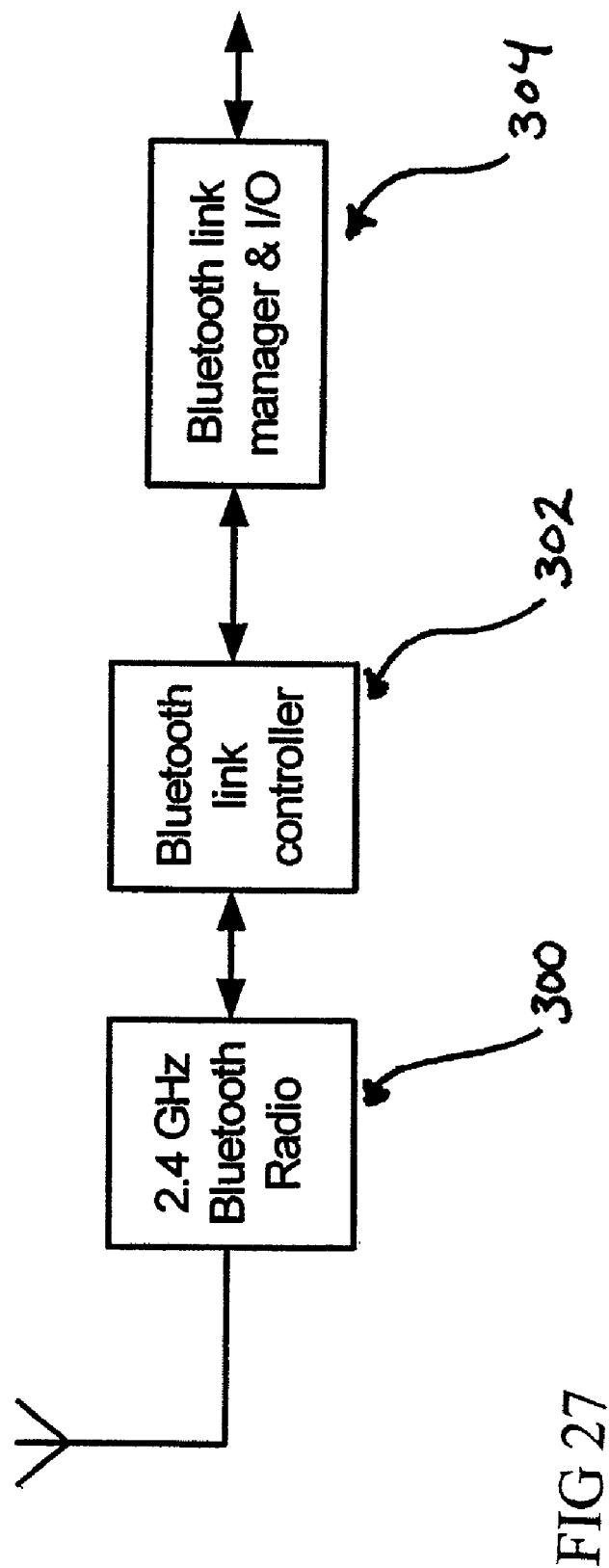
FIG. 27 is a block diagram of the BLUETOOTH air interface radio system used with the present invention.

As described above, various air-interfaces (e.g., BLUETOOTH or IEEE 802.11b) can be used for transmitting the physiological and non-physiological data from the body electronics unit 14 to the base station 16. Preferably, the technology used for the signal transmission between the body electronics unit 14 and the base station 16 is based on the BLUETOOTH air interface specification for two-way communication. The BLUETOOTH air interface radio system, depicted in FIG. 27, consists of a radio unit 300, a link control unit 302, and a support unit 304 for link management and host terminal interface functions.

The BLUETOOTH air interface system may provide a point-to-point connection (only one body electronics unit 14 and one base station 16 involved), or a point-to-multipoint connection (when multiple body electronics units 14 and base stations 16 are involved). In the point-to-multipoint connection, the transmission channel is shared among several electronics units 14 and base stations 16. When an electronics unit 14 and a base station 16 share the same channel, a "piconet" is formed. In such an embodiment, the base station 16 performs as the master of the piconet, and the electronics unit 14 performs as the slave.

Up to seven slaves can be active in a piconet. Many more slaves, however, can remain locked to the master in a so-called parked state. These parked slaves cannot be active on the channel, but remain synchronized to the master. Both for active and parked slaves, the channel access is controlled by the master. Each piconet can only have a single master. However, slaves can participate in different piconets on a time-division multiplex basis. In addition, a master in one piconet can be a slave in another piconet. The piconets shall not be time or frequency synchronized. Each piconet has its own hopping channel.

The radio 300 uses a spread spectrum, frequency hopping, full-duplex signal at up to 1600 hops/sec. The signal hops among the radio frequency channels at 1 MHz intervals to provide a high degree of interference immunity. Information is exchanged through packets. Each packet is transmitted on a different hop frequency. A packet nominally covers a single slot (e.g., 1 MHz bandwidth), but can be extended to cover up to five slots. The BLUETOOTH air interface specification can support an asynchronous data channel (e.g., one direction), up to three simultaneous synchronous voice channels, or a channel, which simultaneously supports asynchronous data and synchronous voice. The asynchronous channel can support maximal 723.2 kb/s asymmetric (and still up to 57.6 kb/s in the return direction), or 433.9 kb/s symmetric.

The channel is represented by a pseudo-random hopping sequence hopping through the radio frequency channels. The hopping sequence is unique for the piconet and is determined by the BLUETOOTH air interface device address of the master (e.g., each base station 16 has a transceiver that is allocated a unique 48-bit BLUETOOTH air interface device address). The phase in the hopping sequence is determined by the BLUETOOTH air interface clock of the master. The channel is divided into time slots where each slot corresponds to an RF hop frequency. Consecutive hops correspond to different RF hop frequencies. The nominal hop rate is 1600 hops/s. All BLUETOOTH air interface units participating in the piconet are time and hop synchronized to the channel.

Each time slot is 625 µs in length. In the time slots, the master (i.e., the base station 16) and slave (i.e., the body electronics unit 14) can transmit packets. A time division duplexing (TDD) scheme is used where a master and a slave alternatively transmit in a synchronous manner. The master shall start its transmission in even numbered time slots only, and the slave shall start its transmission in odd numbered time slots only. The packet start shall be aligned with the slot start. Packets transmitted by the master or the slave may extend over or up to five time slots. Due to packet types that cover more than a single slot, master transmission may continue in odd numbered slots and slave transmission may continue in even numbered slots.

The RF hop frequency shall remain fixed for the duration of the packet. For a single packet, the RF hop frequency to be used is derived from the current BLUETOOTH air interface clock value. For a multi-slot packet, the RF hop frequency to be used for the entire packet is derived from the BLUETOOTH air interface clock value in the first slot of the packet. The RF hop frequency in the first slot after a multi-slot packet shall use the frequency as determined by the current BLUETOOTH air interface clock value. If a packet occupies more than one time slot, the hop frequency applied shall be the hop frequency as applied in the time slot where the packet transmission was started.

The hopping sequence selection procedure consists of selecting a sequence and mapping this sequence on the hop frequencies. The type of sequence selected mostly depends on the state of the devices communicating.

Every BLUETOOTH air interface unit has an internal system clock, which determines the timing and hopping of the transceiver. The BLUETOOTH air interface clock is derived from a free running native clock, which is never adjusted and is never turned off. For synchronization with other units, only offsets are used that, added to the native clock, provide temporary BLUETOOTH air interface clocks which are mutually synchronized. It should be noted that the BLUETOOTH air interface clock has no relation to the time of day; it can therefore be initialized at any value. The BLUETOOTH air interface clock provides the heart beat of the BLUETOOTH air interface transceiver. Its resolution is at least half the transmission or reception slot length, or 312.5 µs. The clock has a cycle of about a day.

The timing and the frequency hopping on the channel of a piconet are determined by the BLUETOOTH air interface clock of the master. When the piconet is established, the master clock is communicated to the slaves. Each slave adds an offset to its native clock to be synchronized to the master clock. Since the clocks are free running, the offsets have to be updated regularly. This offset is updated each time a packet is received from the master: by comparing the exact receiver timing of the received packet with the estimated receiver timing, the slaves correct the offset for any timing misalignments.

Frequency hopping is accomplished with the use of a fast settling phase locked loop (PLL). Since BLUETOOTH air interface hops up to 1600 hops/second, the PLL remains on a channel only 625 µs, which means that the PLL lock time can be only a fraction of this, or else the system will be waiting too long for the PLL to switch frequencies and the data rate will be too slow. Therefore, typically, after a 220 µs settling delay, the voltage control oscillator (VCO) of the PLL is locked and is at the prescribed RF hop channel. The RF output of the VCO is used as a local oscillator.

The data transmitted has a symbol rate of 1 Ms/s (mega sample per second). A Gaussian-shaped, binary frequency shift keying (FSK) modulation is applied with a bandwidth bit-duration (BT) product of 0.5. A binary one is represented by a positive frequency deviation, and a binary zero is represented by a negative frequency deviation. The maximum frequency deviation shall be between 140 kHz and 175 kHz. The modulation index must be between 0.28 and 0.35.

The bit ordering when defining packets and messages follows the Little Endian format (i.e., the least significant bit (LSB) is the first bit sent over the air and in illustrations, the LSB is shown on the left side). Furthermore, data fields generated internally, such as the packet header fields and payload header length, are transmitted with the LSB first. The data on the piconet channel is conveyed in packets. Each packet consists of 3 entities: the access code, the header, and the payload. The access code and header are of fixed size: 72 bits and 54 bits respectively. The payload can range from zero to a maximum of 2745 bits. Each packet starts with an access code. If a packet header follows, the access code is 72 bits long; otherwise the access code is 68 bits long. This access code is used for synchronization, DC offset compensation, and identification. The access code identifies all packets exchanged on the channel of the piconet: all packets sent in the same piconet are preceded by the same channel access code. In the receiver of the BLUETOOTH air interface unit, a sliding correlator correlates against the access code and triggers when a threshold is exceeded. This trigger signal is used to determine the receive timing.

Before transmission, both the header and the payload are scrambled with a data whitening word in order to randomize the data from highly redundant patterns and to minimize DC bias in the packet. The scrambling is performed prior to field error control (FEC) encoding. At the receiver, the received data is descrambled using the same whitening word generated in the recipient. The descrambling is performed after FEC decoding.

After transmission, a return packet is expected N×625 µs after the start of the transmitter burst where N is an odd, positive integer. N depends on the type of the transmitted packet. To allow for some time slipping, an uncertainty window is defined around the exact receive timing. During normal operation, the window length is 20 µs, which allows the receiver burst to arrive up to 10 µs too early or 10 µs too late.

In the foregoing specification, the present invention has been described with reference to specific exemplary embodiments thereof. It will be apparent to those skilled in the art, that a person understanding this invention may conceive of changes or other embodiments or variations, which utilize the principles of this invention without departing from the broader spirit and scope of the invention. The specification and drawings are, therefore, to be regarded in an illustrative rather than restrictive sense.

Accordingly, it is not intended that the invention be limited except as may be necessary in view of the appended claims.

What is claimed is:

1. A system for transmitting data comprising:
a chest assembly comprising at least a first electrode connector and a second electrode connector configured to couple electrodes to traces that run along the chest assembly;
a discrete body electronics unit separable from the chest assembly, the chest assembly being removably connected proximate to and in electrical contact with the body electronics unit, wherein the body electronics unit acquires physiological data from the chest assembly and wirelessly transmits the physiological data;
a plurality of base stations for receiving the physiological data transmitted from the body electronics unit, each base station capable of being simultaneously paired to the body electronics unit by activation of a switch on the body electronics unit and then pairing the body electronics unit with the plurality of base stations such that each of the base stations is enabled to receive physiological data transmitted by the body electronics unit, each base station comprising a plurality of terminals for transmitting the physiological data to a monitor.

2. The system of claim 1, wherein the physiological data is transmitted from the body electronics unit to the plurality of base stations using two-way communication.

3. The system of claim 1, wherein the body electronics unit is configured to transmit non-physiological data to each base station.

4. The system of claim 3, wherein the physiological data corresponds to a patient's respiration rate and cardiac activity and the non-physiological data corresponds to pacemaker pulse data.

5. The system of claim 1, wherein each base station is configured to transmit non-physiological signals to the body electronics unit.

6. The system of claim 1, wherein the body electronics unit is configured to continuously transmit physiological data to a first base station and to simultaneously transmit physiological data to a second base station for a temporary amount of time.

7. The system of claim 1, wherein the chest assembly further comprises:
a base layer having a first side and a second side, wherein the first side contains a plurality of electrically conductive elements, the electrically conductive elements configured to be removably coupled to electrodes, the base layer positioned between a first insulating layer and a second insulating layer.

8. The system of claim 7, wherein the chest assembly further comprises a plurality of electrode housings, each electrode housing positioned over an aperture formed in the chest assembly and containing an elastomeric portion defining a female void for receiving a portion of an electrode.

9. The system of claim 8, wherein the aperture forms at least one flap for engaging an electrode positioned through the aperture.

10. The system of claim 7, wherein the chest assembly further comprises a plurality of electrode housings, each electrode housing positioned over an aperture formed in the chest assembly and containing an elastomeric portion defining a female void for receiving a conductive member configured to be coupled to an electrode.

11. The system of claim 10, wherein the aperture forms at least one flap for engaging an electrode positioned through the aperture.

12. The system of claim 7, wherein the chest assembly further comprises a plurality of electrode housings, each electrode housing positioned over an aperture formed in the chest assembly and containing a male conductive connector configured to be coupled to an electrode.

13. The system of claim 12, wherein the aperture forms at least one flap for engaging an electrode positioned through the aperture.

14. The system of claim 1, wherein the body electronics unit may be paired to any base station immediately preceding transmission of physiological data from the chest assembly to the base station.

15. The system of claim 1 further comprising at least one battery configured for use with both the body electronics unit and the base station, wherein the base station is capable of charging the battery.

16. The system of claim 15 further comprising a second battery configured to be interchangeable with the first battery, wherein the batteries can be swapped between the body electronics unit and the base station.

17. The system of claim 15, wherein the battery contains an indicator for monitoring the charge of the battery.

18. The system of claim 1, wherein the base station is contained within the monitor.

19. The system of claim 1, wherein an alarm signal is transmitted from the body electronics unit to the base station upon the detection of a fault condition in the first electrode, the second electrode, or the body electronics unit.

20. The system of claim 1, wherein an alarm signal is transmitted from the base station to the body electronics unit upon the detection of a fault condition in the base station.

* * * * *